US010995334B2

(12) United States Patent
Collard et al.

(10) Patent No.: US 10,995,334 B2
(45) Date of Patent: May 4, 2021

(54) TREATMENT OF NUCLEAR FACTOR (ERYTHROID-DERIVED 2)-LIKE 2 (NRF2) RELATED DISEASES BY INHIBITION OF NATURAL ANTISENSE TRANSCRIPT TO NRF2

(71) Applicant: CuRNA, Inc., Miami, FL (US)

(72) Inventors: Joseph Collard, Delray Beach, FL (US); Olga Khorkova Sherman, Tequesta, FL (US); Carlos Coito, West Palm Beach, FL (US)

(73) Assignee: CuRNA Inc., Miami, FL (US)

( * ) Notice: Subject to any disclaimer, the term of this patent is extended or adjusted under 35 U.S.C. 154(b) by 0 days.

(21) Appl. No.: 15/270,752

(22) Filed: Sep. 20, 2016

(65) Prior Publication Data

US 2017/0145411 A1    May 25, 2017

Related U.S. Application Data

(62) Division of application No. 13/256,720, filed as application No. PCT/US2010/027394 on Mar. 16, 2010, now Pat. No. 9,464,287.

(60) Provisional application No. 61/181,062, filed on May 26, 2009, provisional application No. 61/160,369, filed on Mar. 16, 2009.

(51) Int. Cl.
C12N 15/113 (2010.01)
C12Q 1/6876 (2018.01)
G01N 25/04 (2006.01)

(52) U.S. Cl.
CPC .......... *C12N 15/113* (2013.01); *C12Q 1/6876* (2013.01); *G01N 25/04* (2013.01); *C12N 2310/113* (2013.01); *C12N 2310/14* (2013.01); *C12N 2310/312* (2013.01); *C12N 2310/313* (2013.01); *C12N 2310/315* (2013.01); *C12N 2310/321* (2013.01); *C12N 2310/322* (2013.01); *C12N 2310/3231* (2013.01); *C12Q 2600/136* (2013.01); *C12Q 2600/178* (2013.01)

(58) Field of Classification Search
CPC .............. A61K 31/713; C12N 15/1136; C12N 2310/111; C12N 2310/113
USPC .... 435/6.1, 91.1, 91.31, 455, 458; 535/23.1, 535/24.5
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |

(Continued)

FOREIGN PATENT DOCUMENTS

CA    2686933        4/2008
EP    335451 A3     3/1988

(Continued)

OTHER PUBLICATIONS

Ausubel, Current Protocols in Molecular Biology vol. 1, 1994, 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).
Baum, "Solid-phase synthesis of benzodiazepines," C&EN News, Jan. 18, p. 33-34 (1993).

(Continued)

Primary Examiner — Jane J Zara
(74) Attorney, Agent, or Firm — CuRNA, Inc.; Monte R. Browder

(57) ABSTRACT

The present invention relates to antisense oligonucleotides that modulate the expression of and/or function of Nuclear factor (erythroid-derived 2)-like 2 (NRF2), in particular, by targeting natural antisense polynucleotides of Nuclear factor (erythroid-derived 2)-like 2 (NRF2). The invention also relates to the identification of these antisense oligonucleotides and their use in treating diseases and disorders associated with the expression of NRF2.

10 Claims, 14 Drawing Sheets

Specification includes a Sequence Listing.

(56) References Cited

U.S. PATENT DOCUMENTS

| | | |
|---|---|---|
| 6,013,786 A | 1/2000 | Chen et al. |
| 6,034,233 A | 3/2000 | Ecker et al. |
| 6,100,090 A | 8/2000 | Monia et al. |
| 6,140,492 A | 10/2000 | Morelli et al. |
| 6,147,200 A | 11/2000 | Manoharan et al. |
| 6,165,712 A | 12/2000 | Foulkes et al. |
| 6,165,990 A | 12/2000 | Singh et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramassamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Hong et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tauguay et al. |
| 7,235,653 B2 | 6/2007 | Bennett et al. |
| 7,238,858 B2 | 7/2007 | Marraccini et al. |
| 7,250,496 B2 * | 7/2007 | Bentwich ............... G16B 20/00 536/23.1 |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Seth et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bamcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Seth et al. |
| 7,745,609 B2 | 6/2010 | Bennett et al. |
| 7,749,978 B2 | 7/2010 | Sah et al. |
| 8,921,334 B2 | 12/2014 | Collard et al. |
| 9,464,287 B2 | 10/2016 | Collard et al. |
| 2003/0139359 A1 | 7/2003 | Dobie |
| 2003/0186920 A1 | 10/2003 | Sirois |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0137423 A1 | 7/2004 | Hayden et al. |
| 2004/0138155 A1 | 7/2004 | Baird et al. |
| 2004/0175803 A1 | 9/2004 | Meritet et al. |
| 2004/0180336 A1 | 9/2004 | Gilad et al. |
| 2004/0254137 A1 | 12/2004 | Ackermann et al. |
| 2005/0009771 A1 | 1/2005 | Levanon et al. |
| 2005/0026160 A1 | 2/2005 | Allerson et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0215504 A1 | 9/2005 | Bennett et al. |
| 2005/0222029 A1 | 10/2005 | Bartel et al. |
| 2005/0277608 A1 * | 12/2005 | Guerciolini ......... C12N 15/1138 514/44 A |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0031844 A1 * | 2/2007 | Khvorova ............ A61K 31/713 435/6.11 |
| 2007/0082848 A1 | 4/2007 | Alitalo et al. |
| 2007/0197459 A1 | 8/2007 | Milner |
| 2007/0213274 A1 | 9/2007 | Salonen |
| 2007/0213292 A1 | 9/2007 | Stoffel et al. |
| 2007/0231816 A1 | 10/2007 | Chaussabel et al. |

(56) References Cited

U.S. PATENT DOCUMENTS

| | | |
|---|---|---|
| 2007/0248590 A1 | 10/2007 | Milne et al. |
| 2008/0146788 A1 | 6/2008 | Bhat et al. |
| 2008/0221051 A1 | 9/2008 | Becker et al. |
| 2008/0293142 A1 | 11/2008 | Liu et al. |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0258925 A1 | 10/2009 | Wahlestedt |
| 2009/0306357 A1* | 12/2009 | Bhanot ............... A61P 3/10 536/24.5 |
| 2009/0318536 A1 | 12/2009 | Freier et al. |
| 2009/0326041 A1 | 12/2009 | Bhanot et al. |
| 2010/0105760 A1 | 4/2010 | Collard et al. |
| 2012/0004184 A1 | 1/2012 | Collard et al. |

FOREIGN PATENT DOCUMENTS

| | | | |
|---|---|---|---|
| EP | 335451 A2 | 10/1989 | |
| WO | WO-1984/03564 | 9/1984 | |
| WO | WO-1991/19735 | 12/1991 | |
| WO | WO-1992/00091 | 1/1992 | |
| WO | WO-1992/08796 | 5/1992 | |
| WO | WO-1993/20242 | 10/1993 | |
| WO | WO-1994-026887 A1 | 11/1994 | |
| WO | WO-1994/28143 | 12/1994 | |
| WO | WO-1995-015373 A2 | 6/1995 | |
| WO | WO-1995/22618 | 8/1995 | |
| WO | WO-1995/25116 | 10/1995 | |
| WO | WO-1995/35505 | 12/1995 | |
| WO | WO-1996-027663 A2 | 9/1996 | |
| WO | WO-1997-039120 A1 | 10/1997 | |
| WO | WO-1999-014226 A1 | 3/1999 | |
| WO | WO-1999-039352 A1 | 8/1999 | |
| WO | WO-2000-057837 A1 | 10/2000 | |
| WO | WO-2000-061770 A2 | 10/2000 | |
| WO | WO-2001-000669 A2 | 1/2001 | |
| WO | WO-2001-21631 A2 | 3/2001 | |
| WO | WO-2001-025488 A2 | 4/2001 | |
| WO | WO-2001-051630 A1 | 7/2001 | |
| WO | WO-2002-062840 A1 | 8/2002 | |
| WO | WO-2002-068688 A1 | 9/2002 | |
| WO | WO-03025176 A2 * | 3/2003 | ......... C07K 14/4747 |
| WO | WO-2004-016255 A1 | 2/2004 | |
| WO | WO-2004-024079 A2 | 3/2004 | |
| WO | WO-2004-030750 A1 | 4/2004 | |
| WO | WO-2004-041838 A1 | 5/2004 | |
| WO | WO-2004-104161 A2 | 12/2004 | |
| WO | WO-2005-045034 A2 | 5/2005 | |
| WO | WO-2005-070136 A2 | 8/2005 | |
| WO | WO-2005-079862 A1 | 9/2005 | |
| WO | WO-2007-028065 A2 | 3/2007 | |
| WO | 2007054520 A2 | 5/2007 | |
| WO | WO-2007054520 A2 * | 5/2007 | ........... C12N 15/111 |
| WO | WO-2007-071182 A1 | 6/2007 | |
| WO | 2007087113 A2 | 8/2007 | |
| WO | WO-2007-087113 A2 | 8/2007 | |
| WO | WO-2007-138023 A1 | 12/2007 | |
| WO | WO-2008-057556 A2 | 5/2008 | |
| WO | WO-2008-066672 A2 | 6/2008 | |
| WO | WO-2008-087561 A2 | 7/2008 | |
| WO | 2008115387 A2 | 9/2008 | |
| WO | 2008124660 A2 | 10/2008 | |
| WO | WO-2010-002984 A1 | 1/2010 | |
| WO | WO-2010-040571 A2 | 4/2010 | |
| WO | WO-2010-054364 A1 | 5/2010 | |
| WO | WO-2010-058227 A2 | 5/2010 | |

OTHER PUBLICATIONS

Bernstein, E., et al., "Role for a Bidentate Ribonuclease in the Initiation Step of RNA Interference," Nature 409:363-366 (2001).
Boutla, A., et al., "Short 5'-phosphorylated double-stranded RNAs induce RNA interference in *Drosophila*," Curr. Biol. 11:1776-1780 (2001).
Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).
Brazma & Vilo, "Gene expression data analysis," FEBS Lett., 480:17-24 (2000).
Bright, et al., "Chapter 6. Fluorescence Ratio Imaging Microscopy," Methods in Cell Biology vol. 30, Taylor and Wang (eds) p. 157-192 (1989).
Bright, et al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1987).
Budni, J., et al., "The Involvement of BDNF, NGF and GDNF in Aging and Alzheimer's Disease," Aging and Disease, vol. 6, No. 5, pp. 331-341, (2016).
Campbell, et al., "Phosphonmate Ester Synthesis Using a Modified Mitsunobu Condensation," J. Org. Chem. 59:658-660 (1994).
Caplen, N. J., et al., "Specific inhibition of gene expression by small double-stranded RNAs in invertebrate and vertebrate systems," PNAS Sci. USA 98:9742-9747 (2001).
Carninci, et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Celis, et al., "Gene expression profiling: monitoring transcription and translation products using DNA microarrays and proteomics," FEBS Lett., 480:2-16 (2000).
Chabala, J.C., "Solid-phase combinatorial chemistry and novel tagging methods for identifying leads," Curr Opin Biotechnol. 6:632-639 (1995).
Cech, J., "Ribozymes and Their Medical Implications," American. Med Assoc. 260:3030-3035 (1988).
Chen, et al., "Expression of ssDNA in Mammalian Cells," BioTechniques 34:167-171 (2003).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleotide resolution," Science 308:5725:1149-1154 (2005).
Cho, et al., "An Unnatural Biopolymer," Science 261:1303-1305 (1993).
Christiensen, N. K. et al., "A Novel Class of Oligonucleotide Analogues Containing 2'-O,3'-C-Linked [3.2. 0]Bicycloarabinonucleoside Monomers: Synthesis, Thermal Affinity Studies, and Molecular Modeling," J. Am. Chem. Soc., 120:5458-5463 (1998).
Cubitt, et al., "Understanding, improving and using green fluorescent proteins," Trends in Biochemical Science 20:448-455 (1995).
Curiel, D. T. et al., "Adenovirus enhancement of transferrin-polylysine-mediated gene delivery," PNAS 88:8850-8854 (1991).
Dai et al., "SIRT1 Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).

(56) References Cited

OTHER PUBLICATIONS

Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA," Annu Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).

Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigen RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).

(56) References Cited

OTHER PUBLICATIONS

Manoharan, et al., "Chemical Modifications to Improve Uptake and Bioavailability of Antisense Oligonucleotides," Ann. N. Y. Acad. Scie 660:306-309 (1992).

Manoharan, et al., "Introduction of a Lipophilic Thioether in teh Minor Groove of Nucleic Acids for Antisense Applications," Bioorg. Med. Chem. Let 3:2765-2770 (1993).

Manoharan, et al., "Cholic Acid-Oligonucleotide Conjugates for Antisense Applications," Bioorg. Med. Chem. Let 4;1053 (1994).

Manoharan, et al., "Oligonucleotide Conjugates: Alteration of the Pharmacokinetic Properties of Antisense Agents," Nucleosides & Nucleotides 14:969-973 (1995).

Manoharan, M., "2'-Carbohydrate modifications in antisense oligonucleotide therapy: importance of conformation, configurationj and conjugation," Biochemica et Biophysica Acta 1489:117-139 (1999).

Mattick, J. S. "RNA regulation: a new genetics?" Nat. Rev. Genet 5:4:316-323 (2004).

Maurer, R.A., "Cationic Liposome-Mediated Transfection of Primary Cultures of Rat Pituitary Cells," Bethesda Res. Lab. Focus 11:2:25 (1989).

McNeil in Methods in Cell Biology vol. 29, Taylor and Wang (eds.) p. 153-173 (1989).

Morelli et al., "The antisense bcl-2-IgH transcript is an optimal target for synthetic oligonucleotides," PNAS USA 94:8150-8155 (1997).

Nielsen, et al., "Sequence-Selective Recognition of DNA by Strand Displacement with a Thymine-Substituted Polyamide," Science 254:1497-1500 (1991).

Oberhauser, et al., "Effective incorporation of 2'-O-methyl-oligoribonucleotides into liposomes and enhanced cell association through modification with thiocholesterol," Nucl. Acids Res. 20:533-538 (1992).

Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).

Prasanth, et al., "Regulating Gene Expression through RNA Nuclear Retention," Cell 123, 249-263 (2005).

Prashar & Weissman, "READS: A Method for Display of 3' -End Fragments of Restriction Enzyme-Digested cDNAs for Analysis of Differential Gene Expression," Methods Enzymol., 303:258-272 (1999).

Quantin, et al., "Adenovirus as an expression vector in muscle cells in vivo," PNAS 89:2581-2584 (1992).

Rosenfeld, et al., "In Vivo Transfer of the Human Cystic Fibrosis Transmembrane Conductance Regulator Gene to the Airway Epithelium," Cell, 68:143-155 (1992).

Rosok and Sioud, "Systematic identification of sense-antisense transcripts in mammalian cells," Nature Biotech. 22(1):104-108 (2004).

Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).

Sanghvi, Y.S., in Crooke, S.T. and Lebleu, B., eds., Antisense Research and Applications, CRC Press, Boca Raton, 1993, p. 276-278.

Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).

Schena, et al., "Parallel human genome analysis: Microarray-based expression monitoring of 1000 genes," PNAS 93:10614-10619(1996).

Shea, et al., "Synthesis, hybridization properties and antiviral activity of lipid-oligodeoxynucleotide conjugates," Nucl. Acids Res 18:3777-3783 (1990).

Shen, T., et al., "Modification of Globin Gene Expression by RNA Targeting Strategies," Experimental Hematology, vol. 35, No. 8, pp. 1209-1218, (2007).

Shimomura, et al., "Semi-synthetic aequorin," J. of Biochemistry (Tokyo) 251:405-410 (1988).

Singer, et al., "Targeting BACE1 with siRNAs ameliorates Alzheimer disease neuropathology in a transgenic model," Nat Neurosci 8:1343-1349 (2005).

Southwick, et al., "Cyanine Dye Labeling Reagents-Carboxymethylindocyanine Succinimidyl Esters," Cytometry 11:418-430 (1990).

Stratford-Perricadet, et al., "Widespread Long-term Gene Transfer to Mouse Skeletal Muscles and Heart," J. Clin. Invest., 90:626-630 (1992).

Sullenger, et al., "Overexpression of TAR sequences Renders Cells Resistant to Human Immunodeficiency Virus Replication," Cell63:601-608 (1990).

Sun, et al., "Downregulation of Sirt1 by antisense oligonucleotides induces apoptosis and enhances radiations sensitization in A549 lung cancer cells," Lung Cancer 58(1):21-29 (2007).

Sutcliffe, et al., "TOGA: An automated parsing technology for analyzing expression of nearly all genes," PNAS, 97:1976-1981 (2000).

Sutton, et al., "TIGR Assembler: A New Tool for Assembling Large Shotgun Sequencing Projects," Genome Science & Tech., 1:9-19 (1995).

Svinarchuk, et al "Inhibition of HIV proliferation in MT-4 cells by antisense oligonucleotide conjugated to lipophilic groups," Biochimie 75:49-54 (1993).

Tamagno, et al., "The various aggregation states of β-amyloid 1-42 mediate different effects on oxidative stress, neurodegeneration, and BACE-1 expression," Free Radic Biol Med 41:202-212 (2006).

Thakker, D.R., et al., "siRNA-mediated knockdown of the serotonin transporter in the adult mouse brain," Mol Psychiatry 10:782-789 (2005).

Thakker, et al., "Neurochemical and behavioral consequences of widespread gene knockdown in the adult mouse brain by using nonviral RNA interference," PNAS 101:17270-17275 (2004).

Thomas et al., "Intracellular pH Measurements in Ehrlich Ascites Tumor Cells Utilizing Spectroscopic Probes Generated in Situ," Biochemistry 18:2210-2218 (1979).

Thompson, et al., "Synthesis and Applications of Small Molecule Libraries" Chem Rev 96:555-600 (1996).

To, KY, "Identification of Differential Gene Expressionm by High Throughput Analysis," Comb. Chem. High Throughput Screen 3:235-241 (2000).

Tong, et al., "Oxidative stress potentiates BACE1 gene expression," Neural Transm 112, 455-469 (2005).

Toulme, J.J., "New candidates for true antisense," Nature Biotechnology 19:17-18 (2001).

Tsien in Methods in Cell Biology vol. 30 Taylor and Wang (eds) p. 127-156 (1989).

Ulhman, E., "Recent advances in the medical chemistry of antisense oligonucleotide," Current Opinions in Drug Discovery & Development 3:203-213 (2000).

Van Den Eynde Bj, "T cell defined tumor antigens," Curr Opin Immunol 9:684-693 (1997).

Van Der Bruggen, et al., "Tumor-specific shared antigenic peptides recognized by human T cells," Immunol Rev188:51-64 (2002).

Vanhee-Brossolet and Vaquero, "Do natural antisense transcripts make sense in eukaryotes?" Gene 211:1-9 (1998).

Vaughn, et al., "Human Antibodies with Sub-nanomolar Affinities Isolated from a Large Non-immunized Phage Display Library," Nature Biotechnology, 14:3:309-314 (1996).

Velculescu, et al., "Serial Analysis of Gene Expression," Science 270:484-487 (1995).

Wahlesiedt, "Natural antisense and noncoding RNA transcripts as potential drug targets," Drug Discovery Today 11 (11/12):503-508 (2006).

Wahlesiedt, C., "Antisense oligonucleotide strategies in neuropharmacology," Trends Pharmacol Sci 15:2:42-46 (1994).

Walsh, et al., The role of cell-derived oligomers of Aβ in Alzheimer's disease and avenues for therapeutic intervention, Biochem Soc Trans 33: 1087-1090 (2005).

(56) References Cited

OTHER PUBLICATIONS

Wang, B.B. et al., "Identification of a nuclear-specific cyclophilin which interacts with the proteinase inhibitor eglin c," Biochem J. 314 (Pt 1) 313-319 (1996).

Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).

Xue, et al., "Hypoxia and reoxygenation increased BACE1 mRNA and protein levels in human neuroblastoma SH-SY5Y cells," Neurosci Lett 405,231-235 (2006).

Yamada, et at, "Endothelial Nitric-Oxide Synthase Antisense (NOS3AS) Gene Encodes an Autophagy-Related Protein (APG9-like2) Highly Expressed in Trophoblast" (2005).

Yang, et al., "Cellular and Humoral Immune Responses to Viral Antigens Create Barriers to Lung-Directed Gene Therapy with Recombinant Adenoviruses," J. Virol. 69:2004-2015 (1995).

Yoshigai, et al., "Characterization of Natural Antisense Transcripts Expressed from Interleukin 1β-inducible Genes in Rat Hepatocytes," HOAJ Biology; 1-10 (2012).

EP Application No. 06850393.7 Examination Report dated Oct. 18, 2011.

International Search Report and Written Opinion for PCT Application No. PCT/US2010/033078 dated Jun. 29, 2011.

PCT/US2010/026119 Search Report and Written Opinion dated Feb. 7, 2011.

PCT/US2010/024079 Search Report and Written Opinion dated Jan. 31, 2011.

PCT/US2010/027394 Search Report and Written Opinion dated Nov. 5, 2010.

PCT/US96/10287 (WO97/000271) The Regents of the University of California Jan. 3, 1997.

Chen, P., et al., "Nrf2-Mediated Neuroprotection in the MPTP Mouse Model of Parkinson's Disease: Critical Role for the Astrocyte", Proceedings of the National Academy of Sciences of the United States of America, vol. 106, No, 8, pp. 2933-2938, (2009).

Joshi, G., et al., "The Nrf2-ARE Pathway: A Valuable Therapeutic Target for the Treatment of Neurodegenerative Diseases", Recent Patents on CNS Drug Discovery, vol. 7, No. 3, pp. 218-229, (2012).

Yang, X., et al., "Inhibition of NRF2 Expression by RNAi in Caco-2 Cells", Basic Medical Sciences and Clinics, vol. 26, No. 10, pp. 1072-1077, (2006), Abstract.

Yin, Y., et al., "antiCODE: A Natural Sense-Antisense Transcripts Database", BMC Bioinformatics, vol. 8, No. 319, pp. 1-5, (2007).

Zhang, Y., et al., "NATsDB: Natural Antisense Transcripts Database", Nucleic Acids Research, vol. 35, pp. D156-D161, (2007).

* cited by examiner

FIG. 2

(SEQ ID NO: 1)

>gi| 166295208|ref| NM_006164| Homo sapiens nuclear factor (erythroid-derived 2)-like 2 (NFE2L2), transcript variant 1, mRNA.

AAATCAGGGAGGCGCAGCTCCTACACCAACGCCTTTCCGGGGCTCCGGGTGTGTTTGTTCCAACTGTTTAAACTGTT
TCAAAGCGTCCGAACTCCAGCGACCTTCGCAAACAACTCTTTATCTCGCGGGCGAGAGCGCTGCCCTTATTTGCGGG
GGAGGGCAAACTGAACGCCGGCACCGGGGAGCTAACGGAGACCTCCTCTAGGTCCCCCGCCTGCTGGGACCCCAGCT
GGCAGTCCCTTCCCGCCCCCGGACCGCGAGCTTCTTGCGTCAGCCCCGGCGCGGGTGGGGGATTTTCGGAAGCTCAG
CCCGCGCGGCCGGCGGGGAAGGAAGGGCCCGGACTCTTGCCCCGCCCTTGTGGGGCGGGAGGCGGAGCGGGGCAGG
GGCCCGCCGGCGTGTAGCCGATTACCGAGTGCCGGGGAGCCCGGAGGAGCCGCCGACGCAGCCGCCACCGCCGCCGC
CGCCGCCACCAGAGCCGCCCTGTCCGCGCCGCGCCTCGGCAGCCGGAACAGGGCCGCCGTCGGGGAGCCCCAACACA
CGGTCCACAGCTCATCATGATGGACTTGGAGCTGCCGCCGCCGGGACTCCCGTCCCAGCAGGACATGGATTTGATTG
ACATACTTTGGAGGCAAGATATAGATCTTGGAGTAAGTCGAGAAGTATTTGACTTCAGTCAGCGACGGAAAGAGTAT
GAGCTGGAAAAACAGAAAAAACTTGAAAAGGAAAGACAAGAACAACTCCAAAAGGAGCAAGAGAAAGCCTTTTTCGC
TCAGTTACAACTAGATGAAGAGACAGGTGAATTTCTCCCAATTCAGCCAGCCCAGCACATCCAGTCAGAAACCAGTG
GATCTGCCAACTACTCCCAGGTTGCCCACATTCCCAAATCAGATGCTTTGTACTTTGATGACTGCATGCAGCTTTTG
GCGCAGACATTCCCGTTTGTAGATGACAATGAGGTTTCTTCGGCTACGTTTCAGTCACTTGTTCCTGATATTCCCGG
TCACATCGAGAGCCCAGTCTTCATTGCTACTAATCAGGCTCAGTCACCTGAAACTTCTGTTGCTCAGGTAGCCCCTG
TTGATTTAGACGGTATGCAACAGGACATTGAGCAAGTTTGGGAGGAGCTATTATCCATTCCTGAGTTACAGTGTCTT
AATATTGAAAATGACAAGCTGGTTGAGACTACCATGGTTCCAAGTCCAGAAGCCAAACTGACAGAAGTTGACAATTA
TCATTTTTACTCATCTATACCCTCAATGGAAAAAGAAGTAGGTAACTGTAGTCCACATTTTCTTAATGCTTTTGAGG
ATTCCTTCAGCAGCATCCTCTCCACAGAAGACCCCAACCAGTTGACAGTGAACTCATTAAATTCAGATGCCACAGTC
AACACAGATTTTGGTGATGAATTTTATTCTGCTTTCATAGCTGAGCCCAGTATCAGCAACAGCATGCCCTCACCTGC
TACTTTAAGCCATTCACTCTCTGAACTTCTAAATGGGCCCATTGATGTTTCTGATCTATCACTTTGCAAAGCTTTCA
ACCAAAACCACCCTGAAAGCACAGCAGAATTCAATGATTCTGACTCCGGCATTTCACTAAACACAAGTCCCAGTGTG
GCATCACCAGAACACTCAGTGGAATCTTCCAGCTATGAGACACACTACTTGGCCTCAGTGATTCTGAAGTGGAAGA
GCTAGATAGTGCCCCTGGAAGTGTCAAACAGAATGGTCCTAAAACACCAGTACATTCTTCTGGGGATATGGTACAAC
CCTTGTCACCATCTCAGGGGCAGAGCACTCACGTGCATGATGCCCAATGTGAGAACACACCAGAGAAAGAATTGCCT
GTAAGTCCTGGTCATCGGAAAACCCCATTCACAAAAGACAAACATTCAAGCCGCTTGGAGGCTCATCTCACAAGAGA
TGAACTTAGGGCAAAAGCTCTCCATATCCCATTCCCTGTAGAAAAAATCATTAACCTCCCTGTTGTTGACTTCAACG
AAATGATGTCCAAAGAGCAGTTCAATGAAGCTCAACTTGCATTAATTCGGGATATACGTAGGAGGGGTAAGAATAAA
GTGGCTGCTCAGAATTGCAGAAAAAGAAAACTGGAAAATATAGTAGAACTAGAGCAAGATTTAGATCATTTGAAAGA
TGAAAAAGAAAAATTGCTCAAAGAAAAAGGAGAAAATGACAAAAGCCTTCACCTACTGAAAAAACAACTCAGCACCT
TATATCTCGAAGTTTTCAGCATGCTACGTGATGAAGATGGAAAACCTTATTCTCCTAGTGAATACTCCCTGCAGCAA
ACAAGAGATGGCAATGTTTTCCTTGTTCCCAAAAGTAAGAAGCCAGATGTTAAGAAAACTAGATTTAGGAGGATTT
GACCTTTTCTGAGCTAGTTTTTTTGTACTATTATACTAAAAGCTCCTACTGTGATGTGAAATGCTCATACTTTATAA
GTAATTCTATGCAAAATCATAGCCAAAACTAGTATAGAAAATAATACGAAACTTTAAAAAGCATTGGAGTGTCAGTA
TGTTGAATCAGTAGTTTCACTTTAACTGTAAACAATTTCTTAGGACACCATTTGGGCTAGTTTCTGTGTAAGTGTAA
ATACTACAAAAACTTATTTATACTGTTCTTATGTCATTTGTTATATTCATAGATTTATATGATGATATGACATCTGG
CTAAAAAGAAATTATTGCAAAACTAACCACTATGTACTTTTTTATAAATACTGTATGGACAAAAAATGGCATTTTTT
ATATTAAATTGTTTAGCTCTGGCAAAAAAAAAAAATTTTAAGAGCTGGTACTAATAAAGGATTATTATGACTGTTAA
ATTAAAAAAAAAAAAAAAAAAAAAAAAAAAAAAA

(SEQ ID NO: 2)

>hg18_knownGene_uc010fra.1 range=chr2:177805251-177836511 5'pad=0 3'pad=0 strand=- repeatMasking=none AAGGGACAGGTTGGAGCTGTTGATCTGTTGCGCAATTGCTATTTTCCCCAGAGCGGCTTTGTCTTTGGATTTAGCGT
TTCAGAATTGCAATTCCAAAATGTGTAAGACGGGATATTCTCTTCTGTGCTGTCAAGGgtaagagttgcgagtgtag
attagaatttctgttgcttttagtctgttagtaattttttgctttcagctattatttctcccctgagtactttatat

FIG. 2 (Continued)

```
atgtttccttttcagttgagaatttgcctcaatttcttaacatgttcccctcttctgcaggggcagagagtggaac
gcttgcgtttcaaaacacttgctaatttctgtgaattgttataaaagtgaaaagaagtttctgctcatcctttgtag
aaactttaaaagtagatatttatatttctaacttcttttgtaaatgaattttaggaaaaaaattggaattcaaggaa
atgtgtacttgatgtacagtaaatacgtttatgctgttaaatgtaaagttttcggttaattccaaagatctattgta
aagttttaagttatggacaatgtattaattgtgcttttttccccctttaaagttgtttgtcttgaacttttccccag
tcttcattgggattgtattcttctggttccaactagtgaagaattaaattgtaccttccgatttatttaatagctgc
tgttcaagagttatctataggaatgcttgtttgactgaaggatatatgataaaaatgaactttagtttttctgattt
ccggaattgtctacagccctctattattttttgaattttctttctttgctgtgtaatataacattccttatacaaaa
atgcgtgaaacatatgtaccgcattaagtgtgtattttccaattacgtttgataaaaataactgcttttctacctttt
gtaatcagacatcgatttgcatatttgaaaacagaaaagaacaagaaaatttagaattgattttgtttatgattca
tattagattgttgtcatccataaagatttgaacagagtcaaacattttcttgacctttttgtcaaaaaaactctcca
ggtgtgaagtggtagtaggatatagttttcaccttctgtgcagaggatgtgttgataaacagggcagtaaggagag
ccttagattcagtatctccattaggtggaaggaaccatccattactcttttcaaggggtgtcttggagagataaagca
cttttcctagatgagggatgaagttgatattgaaatagaccgatgagattattttaagtcaaacaaagaaaatag
gacaggcctctcatctcctgaatgaatgttaagcaaagaacaacttgacttttttagatatgtgaaaaatctcttgag
aggttgtggaagcagcatgtaggaggataaatgcataactcacatcagtcttttacgcattaaaaataacttgggcc
atttttgaaatctttctttcttgccctgggttcttataagcaatgttggggggaaaactgactctgtctttaggatta
ccaggaaaagttgaaagccaaatgcatcattttttcttaatatttgttttttattgaggataaatcatgtttaacaaag
ctgcatgaaaaaaaggaacccaacaagtacattttttttttctgggaatttcctctgtcctgactgaagacatttaaa
ggggttttgtgtcaatatttcctccttaactgttcctcaagcctgggttaacttttcagtatgcaggaagaatttg
gcactaagataataatagataagttactgggcacgtccctgggtgccagacataattgcttcacatgcataattta
cagtaacctcacgggaaatattattatccctggtttccaggttgggaaaaccaggcataatagttagatcaggcatt
aggttaggaaaggttaggagagaggcatagagaaaggccaggacctgctaaggtgaccatactattgagtggccaag
gtagcattcaaacaggtttgactcctggggcttctaatcaccacttccagactgtaccaaaactccttaaactcta
aataggaagaaaagctcacactttaaaaagtgggtaagttgagatttgccattctgggggaaggagaggccggaat
ataaaagattaatgtctgcagcttttccatttagcaagacatttaatcactgtatgtgacgtggggaggtggacctt
gttaaatacagggagagtgaatacaatccatcaatggtacccactgtggtcctttaaggaagacacagaggcctcg
gtggattcaatttagaaaggcaggactgttttttgttttttgtttttttttttttttgagatgaagtcttgttctgt
tgcccaggctggaatgcagtggcctgatcttggctcactgcagcctctacttcccgggttcaagtgattctcctgct
tcagcctcccgagtagctggattataggcacccactgcccggctaattttgtattttagtagagatggggtttt
accatgttggccaggctggctggtctcgaactcctgacctcaggtgatccaccccgcctcggcctcccaaagtgttg
ggattacaggtgtgagccactgcgccagtctgtttcttaatataataatagtttttaaaaatttctgatgtttggcaa
tgtccaagattctgcctcacatttttcagaaactgccttttttcttaattaaatctcttagctactggagtctttgc
ctttgtttgccttgctacttggtacatttcttctgttccattggctcttttttgttttgaagtagtgctcaaaaataa
gtttggtagtaagaatatggtgaagagtgtgacagacagggttaaaccaggctgaaggaaagagagcagaatgggga
aaatttgagttgaaaacagctagcagaaagctgatggcgcaaattcaaccctaatctcatgttttggcacttctgaa
ctatagcaagcataagggctcaactcttatctagttgaagcttacttgggtctttgagaatagtacatctcaaaatt
aaacactttcttagtccttattgttaagttgttttttggaattattgtcttatttgtctgaattaagtgtgctgcagg
acttataggatctgatggatgatttgcctaaaagttggtccaggtcaacctcagggcatttaaatgcttggtccagc
cactttctgaaagttgactgaaatatgttgcacagcagggtagaggaggacaagtttactagatgtcattttaacc
tgcttgtcttcatctctgactgtagaaatgtatattcattataagtttgccacaaatagagaatagagtttattctt
tgatcatctaatttctaggagctattgaaatttcactgctacctgcttttaaataagcgccaacaaacatttattaa
aagggctttaaggtataggccaagatttattcaattgctaatggtatgttttctgtaaatgaaagcaaaatatgtt
caagtgtataatattaaatattaacattcagaaacttggagaaatacagatggctttttttttgagacgcagtctt
gctctgtcgcccaggctggagtgcagtggcatgatctccgctcactgcaagctccacctcccgggttcacgccattc
tcctgccccagcctcccgagtagctggtactacaggcacccgccaccacgcctggctaattttttgtattttagta
gagatggggtttcactgtgttagccaggatgatctcgatctcctgacctcatgatccgcctgcctcagcctcccaaa
```

FIG. 2 (Continued)

```
gtgctgggattacaagcttaagccaccgcgcctggcctagatggatttcttgtaccagactatacoctagacatgaa
aacaagactgttaaacaaaatcctgtgctacctaaagtttgagccttctgtgtgtcagtttctgccataataaataa
ctcttaactatgattattaagtatattaagaactttgagtaggggaggcacgtttaatcattcgttttttacggcata
tgtactataatacctgtgtgttgcaaatcctggtatttaaaagtcttttttgtgtatttgagcatgtaagtttatttg
gtccaaactgctggtactagtaaagacaagtccagggcataagtaggacttacagcaccaagttcgtcttttttttt
tgagacagagtctcagtcggtcacccaggctggagtgcattggtacagtctgggctcactgcaccctccacctcccg
agttcaagcgattctcctgcctcagcctcccaagtagctgggattacaagtgtgtgccgccacgcccggttaatttt
tgtattttagtagagatggagtttcactatgttggccaggctgatcccgacctcaggtgatgtgcccaccttggtc
tccgaaagtgctgggattataggcgtgagccactgcgcctgacctccaagtccatctttcaaaggctctgttgataa
ttgactcttgagagtcattacagtccatcaacagcctgtattctgaatatttgttttaattctaagacaatgctaa
atagccattccaaataaggtgagaactgagactttagggcctgtattatcagctgtacactgacaagctctgaactc
tattgctttttcaaatcagagaagaaaaatgagtaagaaaagaaaaatatggatcacttaggctttgatgcctcctc
tgagtttatagtgtttaccttctgtattacttaggtgatcctctctaatggcattttaaatctctgttgatacttgt
cttacttatgtatctgttttttttcctctatagtagatagaatttatagatatatgtattttaaagtaagatac
aatttacgtaccttacaatttacccatttaatctaattcagggttatgcaaccctatgaatttagtagtttattcat
agagttatgcaaccatcactgtaatcaattttcaacaccctcaaaagaaaccccatatccattagcagtcacttccc
atttcccctcaactctcctggccctggtaactactcagttatttctgtacctatggatttgcctattctggacat
atcatgtaaatggaatagcatgtaaatggaatcatacagtatttatccttctgttgctggcttctttcacagcaata
tgttttcaaggtttaaaaatgttgcaacgtatatcaatagcgtcattccttttatggctgcatactattccattgt
atggctataccacattttatttatccagttgatgatcatttgagttgtttccacttttatgtttctgtttgtttct
tacagcagtggttctcaaactgttgtatattagactcaccatcagtatttaaaaaactaatgcccaggccatatccc
tcatgaaatcaaaatctctgggggtggggcccaggcatcactattttttaaagattctgagggattctaacgagca
gtcaggtttgagagccagtgccctagggcagcagtccacaacctttttagcaccagggactagttttgtggaagaca
gtttttccatagaaggaggtagaggatggtttcaggatgaaactgttccacctcagatcatcaggcattagattgtc
ctaaggagctggcaacctacatcccttgcatactcagtttacaacagggttccggcttctctgataaactaatgctg
ctgctaatctgacaggaggtggagctcaggcgggaatgctcgcctactgctcacctcctgctgtgcggcctggttcc
taatgggccactgaccctccgcagccagcaggtggggacccctgcctaggggacccacctcagtgcttggtatcc
attgaagtatatagtgatttagaaaatctggttaggatgtcttatttaaatcatgaaagcaagtgcttttgtctttg
atcattgcccttcacagccttacagttaacacctacattcaggaactgtgtttcaaagtgcctggcgagtgtttgaa
actcactaaatatatataacctgggctcattaaaccctccagaagatttgggtaactttgttatgaaagggcttcc
ctgaagtgggtcagcaggattgctctgtgttttttcaggaatgtggcctgtgataacttgcaatctagattatttgg
aaatagcactgagagaagccagtgaggacagaatgctcagaagcttgggataggtgttgaacatcctggaggccagg
acggaacactgtcttactctaggaagctgtgttcctgggcctcattatcttcctccgttaaaaacaaaagacttaaa
tctccacagcagctttcagcaacttcatttttggttctctgtatctgcctgataaagtcccactttgtagtggctc
ccacttatatttacctgaatggcttttgggttgacatatttggaaactggggctaacttccaaactgttggcaactt
gtgtgtgggtgtgcgtgccacagcacagcagtcccacttgagagacttgatggtgtggtggtggttgggggcttct
gaagctggcttagccccagccctatacacccaccccacagatggtgggaacaagcccagaagagagtgggtaactct
gtccactgtggcctccacagccaaggttgccaggcagagctcgcaaggcccaattccagtcttgtctttgaccgttg
ccccttttgtgttgggggggtgtatttagtcaccttctggaagcatgcttttctaattctagtcatcagtagtttgt
tgctttaagattttgaaaatggtatcctgttattttacttaggagtttcgtattgaatggtgtacataatgtgattc
aagtacctcaaaacagaaggacttcagttaagatttaggctctatgcaacatacacttcttgcattttctcattcaa
tgtcctttccttttttttttttttttttgcaagaatgtagctgacattcagagtagattagtaccttcaatgtc
tgtgtgaaagaaatgaccttaatatgaggacaatattgactgtgtatttagggggcccactgttaaggcatatagaa
ttttgctttatttcagacctgacaatctcttgtctgctctgcttccgcataaaattataatactgcacatggatgta
aaacccaacctattccctgcctgagggactagaatagagggaagaatgactatagttctttgttgcctttgtgaag
gtaacaggcacagaggtatgatgcatgatggaattatatacctcttcttgaggtgtttgagggctgactaaggacct
gtacttttttttttggtttgttttgcagtactggggccagggagccttgctgttgtgtctagagagtgttgaagaacc
```

FIG. 2 (Continued)

```
atgaatatttcgcaaaagaaaataatttttttaaccattaaaattcctggtagtgacttcctctggcaagtaaaaa
actctcattttccttaaaaaatgagagttttttacttgcaataggaaaacttgccaattttttcaagttattttatt
cttgatgattctcaatgagacataattaaaatacacatagaaaaaacaaccgtaggccaggtgcagtggctcacacc
agtaatcccaacactttgggaagtcaaggtgggaggatcactagagaccaggagtttgagatgagcctgggcaacat
attgagacactgtctcctcaaaaaattaaaaaaattagctggatccagtggtgcacacctgcaattgtagctatttg
ggaggctaaggtggaagaatagcttgagcccaggagtttgaaggtgcagtgagccataatcatgccactgtactcca
gcccaggcaacagagtaagatcatgtctcaatgaaaaaagaaaaatcaaccctagtggactggaacagggctggtt
tactttgtgtcagctgcagtgccccactcgccaacccacatgttcttctcctgctggttcccaagcagagaccaga
accaagaatgagaatcatcctgtgggtgcaggttgtatcttatcctccagagacagcacttcaccctctgttagaaa
cttctttaccacactgcctgtttggtgaaatccttagggcagtgacttccaaactgtgatccagggccacccttgg
tgggaggatcaggaaggaggggggaatgtatcttaagaaaagttgggggaagctcatatctcttctcgttgatccga
gaagtaaagtctttcctcctcagagagatgcgggtagacatgactcgcctagatagaagctcattcatctccctccc
ttctgcctctgcaggactcttggaagtctgggtccccggagtatgcggctcttgctctgtgctacaggtttccaaa
gttcacttgataacagtacaattgtgctgtaaattgtgcagtaatggagactgaggaaacaattagtctttcatctt
cattcatgttaccagctcacttcctatggtgtgaaaagagccagactttggagttaggagacatctgaatacagaca
gaactggcaagattatggggaagaaaagggaaaagtaatgaatattttcaaagaggttaagccatttggccaggaca
acactgcttgcaggtagcagaactgggattttgactgtccataatccctattctctgcttgttttactccttccctc
tcttctttctttttttcattgtctaatgacctacagacattctgtcagctgctaaagaatgagggactccttataaa
gattgataggacagtgtcgctacttaaggagttccttccatgtggaccagtggggcgctgttgacgcatgggctg
gacttctctttggagcagagtcctgttccacggatcgctgtgacaagcagaaagtgccccaccccacctccatacaa
ttcctaatgctcctgggtgatacaaccgccccagtggaagcacggtggtgcatggacttctagagaccatttgaagc
caggacattgctgcttgttcttaggaaatggcagaatattactttcttgttttttgtagggaagcctgccatctcac
caggtggcagcttgtttataccttttatcctaacctgaagcaggtgatgggacagaggtcatcgaatataatgaaag
tgccacaaaggtagagtctgggtatattttatttatgcaggtagagtgacttgtccagatcccttcacacagagcaa
catttaatatggtaattgttactgctgaagttggccatttctcggacctacagctgcaaggaattggtaacaaaagg
ataaactaaacattgttactattttaattttcaaggagatgaagttaaaatcatatatgtcatatctctctgggct
tagccaccttttctgctgggcacttttgaagaagtctgaatactgagataggagagtaaaggggggaaagtaagtt
tgcccacttctcatccttttctgaccatcagcctgagggaagtaactagaatccgctaagaaaattcacttaatca
gcagttgattgattgttatattgtccacattgcaaaattctttaaaggatatttgaagatattatcacatttgttct
cttacaatctattgtattgtttatttgaaggggtgagtgttaatagttcttaagatatcgtactttatttccggtag
catatccaagaaataatttagaagtattgttaatgggaatgatgttaaataattttctatgactagtagttgggac
atatatgatataaaacatggtatctttgttacttaagtaatttgaactctaaccccatatatcttaggtagacaatg
aaaatactgaattgttagtctaaataatatacacgtactcattccgcaaatatttattaggtatctacacaccctag
gaatctttcagggcatgaagctgttttaatcttccaagataatgcagcacgtatccccttgagggacatttgtttt
tcaaattgctcctctgtgtctcctctgcttaggatatgagttcctctaagactgtattttaatcttttgtgtaattc
tgatgtctagcgccatgcctggtgcttacgtaatagttgctcagtcagtttgagggtgagtccattaactgccctct
aggagcttgatatttaatataaactagtctgtgatacatgacaatgctgtgacagtgcagatgagaaatgtgactt
ctaactggggtgctcagagaggatatcctggaggaactgccattttaactagacttttcttttaagcaggtagattt
tgtttggttcaggcttcagctggaagcccaagcaatggtgcagatatgagctggactatgacagactattgggccag
tggggctgacaaggttaacttgggggttgccatagagggccttcagtgctcatgtgcactgtttcaagtttgtacag
ggcatctggaaaccatggaagaagattctggaaagggcagggcaggtaaactggatgtggataggaagttactgtgg
caggtgaattggaagatggacaggttggaggcagggagatggtgagcgggctcctgccaaggtgtaggtctgagcat
tgttgtgacggcttagttggtttgacatcagcacacagattgaggatctgtcattgtaactctaaattgtatccttg
ttagacatgtaaaataacttttagagcctccgttttaaggagggaagtggattgtgctcaagcttgcatgctcc
gctgttcctgtgctttaaaaatactcatccaccagtgtggtcactgatgaaaggggaggaaaaactagccagaagtt
gccattttgcttaaagaatggattcatttcttcctcaaggtggcacagagagagtttctctcttttttgcccctctct
tagattgatttactattttttagtaaattctaacagtctgatccttgcttccaattacaatgattagcaatatttgcc
```

FIG. 2 (Continued)

```
caagacaagaaaaaacaatttcctctcttttctctcctatgagcttttcctgtgagccccaagcagacagatgtgga
catctagcaatgctgttaacaacagctgcagtccgttggactctctgcaacactgggcacggtacaaagtgctctga
caaactcttctgcccttttgcaatccttactacgccctgtgaggtgaggagtattcttcctgttttgtaggtgaagaa
ctgaggcaaagagaggttatgtcattagatttcacaatagggtgtgtttccgtttcatcatctttagattgatgtta
ctgtgacatcatcttcctagaattaacaaagtgaactgggcacaggaaatagcacatggcacaccttcagcaaatgg
tggttgtgatcattttcatcattccatttcttcttgaaaaaaatccctttttttttttttttttgagacagagtctc
actctgtcgcccaggctggactggtgtgatctcggctcactgcaagctccgcctcccggttcacgccattcttctg
cctcagcctcctgagtagctgggactacaggcacgggccaccacgcctggctaattttttgtattttagtagaga
cggagtttcaccgtgttagccaggatggtctcgaactcctgacctcgtgatccgcccacctcggcctcccaaagtgc
tgggattacaggcatgagccaccacgcctggcaaaatccctcgagttccagtgtaaacactcacgccctttttgc
tgtttgctataaacctctcattctccttggtcttcttgtccttgtgtgaggtcctggttgttgtggagactgaggtc
ttctgagacagaaaaccaaccccatagcaggcctggtgtgtgccctagaatggcagaggccccacacgttgccccgg
ctcctctggaagaccctccagcctgtctgctggattccttgtacttatgaggattgttaaaccatctcataggattc
ctttccagactcagcccttcacttgtggcagcatttcttactctgaggttctgggcctagaaacccagtgtccatag
gcaaggtctagggacagagagagtttgtagaaagtgggaatgcatcagtggaaggctaaatccaaacaggaactgag
ctggcctgggtggctttgtccttttgccatcttcgtaaccctttaaaggctttaagacacttcttttgtaataacta
ccccaactaaatttggccagagctgtgaagggaaagaaaatctaagacccttgagggagatgacagccgaacgtttt
acattttaccacctttgttgttgccatgcacagctgatacataaacaagtaatggcctcatcttctattctttat
ttactggttagacccagaaccctaaaaggtagatgcttctcatggtcatttggcatttgcaacaggagctgaattta
ttaatagtactaatacctcatccttggacatccttgggttgtccgatatttttaaggggcatttacatcctttgttt
ttcatatggaaaacttttccgtaagggctggtatcatcttggccttccattgcaggaacagcacagggaggttcggt
ggctaggccacagttacccacgcagctaggtagcagcagaggccccacctggcacccctggcttcctaagcacatc
gcactgtgcagcctccctgaggaagcctcgagtggataggaactctggttctttaagataaacctgagttggatctc
actgtcaccatttatcagatggggcgatgtcttcaggcaaaagtacttaacctctctgttttttgtttccttactcca
aaatggtaatgatcatactactacccacctgggtggattggtgtgcatatgaaggaggtcatggggacaagtggttg
gaagagtgttgagcacatagaaagtacaagataaatggtggccattatgttactacttagactatatcatacttgtc
tttatctgggcttagaatcttgacactgagatctttcattctcagatcttaatatgaaagcttaccaggtaaacact
accccaacataattatttagtgggttcatacatgtgaaagcagttgaaatacaatttctgaactccgggttaattta
tatccttagttggaacaggtagtaccctcccagcacctaaggcctctcacttctatccattcttcagatgaccttttg
caataatcatggtaattgaatagcatctgcaccataacattgttgaataacatcaaaatgatccatttagccatcat
gagccttcctagtaattcagactcacaccagttctttcaggttattgagtagcttttacaaataattgctaacagta
caaatactgtctcaggtattttggaagggtgaattttcccattgatttcagtgtatctttaggaggtaatttgcaaa
accgaagagtttggttccgtcaaagtcacccctaaggagtgtggaggaccacattgtaggtttatactgcactgtcc
ctcatgcttgaaatttggctcatgcaaccaaggaactgaatttttaatttcgttaaattttgatttaaattttaaaa
cagaaatagtataaaatatttttctgttaaatataccttgtagtgttggcaagactacatttcgtgttaccatgctg
ggtaagatttcttgtagtgtgtattgtgttttgtcacctcgttaataattttcttattttggttgcatgttaaaata
attttggatatattgggttaaataaatatattgttaaaattaaattcacttgtttattttttttgttggtgaggctag
gctactaaaaaatttaaaattacccatgtggattgcattatatttctattagtgctgctttagctgcaagtagccta
tttaaaaaaaatcattattttcagacttatggacttcatagaatcagaggtatttagaggaaggatcttgggggtc
acctaatccagctccaacattttgcaagtgataagaccaaggccagaggctacaataaaatgactgacctcctccca
gatggggactggatcccagtggctttatagcctttgccttggatcctggttttacttggaaacatagcagacatcag
agctgcagagaacttctaccagatccggagtgaagaaatgccttatttatttatttatttatttatttatttatgg
agaccgggtattgctgtggcctaggctgtagtatagtggcagaaacatggttcactgcagcctcaacctcctgggct
ccaggatcctcatgcctcaaccttctgagtagccggggccacaggtacgcgccaccacgcctggctatttttttttt
tctcttttgtagagactgcgtcttccatgttggccaggctgatatcaaaactcctgggctcaagtggtcctcctacc
ttggtcccccaaagtgctgggataacaggtgtgagccatcatgcctgttttggcagtttttaggggcccacgctaat
tttgagccaggtttgcgcttgataatgtaatgctggaggctgggcaggggacatgatctgcctgaaagggctgagaa
```

FIG. 2 (Continued)

```
ctgggaggctcttattcctatagtattgagagcaaaggcacagtcttacagaaccacacaatattcagagcttgtgg
gttggagaaggaaagtcctctgaaaaataaaaaaaagagtacagaggccagaggcggtggctcatgcctgtaatgcc
agcactttgggagcccaggcaggcggatcacctaaggtgaggagatcgagaccagcctgaccaacatggagaaacc
ctgtctctactaaaaatgcaaaattggccaggcatggtggcgcatgcctgtaatccaagctacttgggaggctgagg
caagagaatcgcttgaacccgggaggcggcggttgcggtgagctgagatcacgccattgcactccagcctgggcaac
aagagtgaaactctgtctcaaaaaaaaagaaacagagtacaggtcagacattgggcaattttctcataacaatttc
ataggccattaatttggttacagacttgaatagcacacaacagttctctaagggtcagtttccaaagtaattcctaa
tatttaatgaattttttaagtgatagaaattgcagtaggaaagtctagcttgaaatctaatttgtgttaggttgacca
ggtgacaaccacccaccccctggattctgctcagttaggtcagacctggggccagttgcccatttagcatctcaggcc
tcaggatcctcatttataaacctggggttttgaactgcggtctccacgatcactgtcagctctccttagtcagttggt
tgttctaaatgtagtttagtggccagtaaacacctgttcctgagtgatacatctttaaggagccggtagatgggtca
acctggctggacttgcttttcaagtctgccttgtctattagaaaggctgagcttactgattttgcctgtcacgttt
gagtgttcctgagactttgcccagcctcggtcttatctgcgggtacccagcctctgcattccttgccctacaaaa
tgtgctgccagttccaaaggcacaaatgaaaattagcttggctggagcatggctaggcacacaccagtggttaaaga
aatgctgtttgctggctgacacttctggagtggaagtttattcttttttcttttttttttttttttttgcggggtgg
ggcagagttttgctcttgttgcccaggttggagtgcaatggcacgatctcggcttggagcgatcttgggtcaccata
acctccgcctcctgggttcaagcgattctcttgcctcagcctctggagtagctgagattataggctcccgctaccac
gcccggctaatttttgtatttttagtagagacagggtttcaccatgttggccaggctggtcttgaactcctgacct
tacgatccacctgcctcggcctcccaaagtgctgggattacaggcttgagccacggcgcccggcctttattccttc
tttggcctcaatttattgttaagagatagtgggaagggcccaattttgaaatgatcctggaattaatgtaggaggc
cttgtataagcagttaatgtgtatttattgagtgggtacctgtgccaatatgatacaaggtgtgaaggacacatga
gttgggaaaggcatgggaaatgcacgctcacactgctggtgcgagtgtaaaaggtacagtctctatgtagggctat
ttggcagtatatactctttgacccagcaactccacttttaagtatttatcttagggatacctcacacatttatgaa
atgatttatatacaaggatattcattatagcaatatttgtaatgcaaaaagaaacaaaagtcagatgggggactga
ttaaataattatgttattaagtaatactgtttcagtacatctgtgtaatgaaataatgtccagtcattaaaaatagt
gaggcaaagtctgggtgcagtggctcacgcctgtaatcccagcaccttgggaggctgaagccggaggattgcttgag
accagcctgggcaacatagtgagaccctgtctgtacaaaaaaaaaaaaaaaaaagtaaaatattagccaggcatagt
ggcacatgcctgtaatctcagctattcaggaggctgaggtgggaagattgcttgagcccaggaggttgaggctgcag
tgagctgtgattctgccactgcactccagcctgggcaacagaacaagacctatcttagaaaaaagaaaaaaaaga
aaaaggacaacttacaactctgtgccctgatgtagaaccatctccaaaatatattaaatgagtgtgggatactatg
cttatatgcgattgtgtgtatttaatggcttcctaagaaaacaaaaaaaacctgatactagtgattgccttggagg
agggtaactgggaaattacttttgcaacttttaaatcttataccatgtacacctggtatctatttttaaaagccat
tttcatgccctaaatgagtttagtcagaccatagtaagaaaatcctgtaagacatacaaagtatggggtaattactg
gctttatgggaagactgatttcaatgcaaaactctccctatgcaagggagttgtcctgatttcaatgctaagctctc
tttaggcaagttacgttggcctgatttgcctgttaagtcgtatggggcaggcaagtctgagtgtccagagggcagac
cttaactcttagtttcctgccttgggagaaggcacagggctaaagtggtttccagaacgtgtctgttgtggtgtga
acaccaaggagcagtggacaagcttcccaggctcaaggtcagaaggtctggactggagtcctgcctctgctacttgg
tgaatatgtgatttggggcaggttgcttaatccccgaagcctcaacgtgttcatctagaaatgaagattacaggctg
gacgcagtggctcatgcctgtaatcccagcactttgggaggctgaggcaggcagatcatctgaggtcaggagttcga
gaccagcttggccaacatggcaaaaccccatccctactaaaaatacaaaaattagctgggcatggtggcaggtgcct
gtaatcccaactactcgggaggctgaggcaggagaatcacttcaacccaggaggtggaggttgcagtgagctgagat
tgtgccactgcactccagcctaggcaacagagtgagactctgtctcaaaaaaaaaagactacaatacctggccca
actccctcatgctactgtagtgaggctcaaatgagatagcacccatgaacactcctgtaaaccatgaagtatgcaaa
caccaggtgtaatagaagctgttaggtacctgtgaggccagcagacaagagcaagagatgctaatttaaaagaatt
aagtgaagcaaagatcttttccctctgccaaataacttggcaagagttgtaaaattagaaagtagacccttagta
gtttgataatcctttgacctctgaccctgcacaaatgatctcacccttagacctgttcccttatttgcaaaacaag
aggggctgtctgggtgattcctgtggtcccttccagttgtagcgttccgtgacagtgtggcattaacagtaattccc
```

FIG. 2 (Continued)

```
atcttggctgagatggatgagtcatactaactgaaaagtcaaaatacgaggaagaagtctctttatgtatgagaatt
ttccttgagctagagactcagagcctcttggggaggagatgagggaaaacattgccaccaccaagaagggagacgaa
ggatgtataaagagaatggagatgtatttactttttttttttttttttttttttgagacagagtctcactctgtcc
ttctggctggagtgcagtggcacgatcttgggttactgcaatctccacctcccaggttcacgccattctcctgcctc
agcctcccaagtagctgggacacaggcgcccaccaccacgcccagctaattttttgtgtttttagtagagatggggt
ttcaccgttagccaggatggtctccatctcctgacctcgtgatccgcccgcctcggcctcccaaagtgctggatta
caggcgtgtgccaccgcacccagccgagattatttacttcttgtgtgttcttgccatctccatagcctcctttgctt
tcaaatgcccacttgggctgggcctttggaaaatagatttaacccttgtttattggaaggatattcacacagtaggc
cagttatacactttgtggcagtcgttacctcttctgtgaggtctttctgtgcagatttagtggcacctcctccatgc
tgcctgggcttctacttgcttctcatcactttgtctcataactcagatcagagactgtgtcttactcatctttgtat
ccctggcatctgaggggtggtatctgatgggtagatggattagtgatccacttagggtatttacactaatcttgtt
gatcttgactactacctttataaccaccaccattctacaagttttaactttttttttttttgagacagagttttgc
tcttgtcacccaggctggagtgcaatggcgcgatcttggctcactgcaacctctgcctccccgggttcaagcgattc
tcctgcctcagcctcccgagtagctgggactacaggcacccgccaccatgcctggctaatttttttgtatttttagt
agagacggggtttcaccgtgttagccaggatggtctcaatctcctgatcctgtgatccacctacctcagcctcctaa
agtgctgggattacaggcgtgagccaccgcacccagcaaggatctttttttttttttttaaagctaagtgttttata
catataataatattgttaataaaatgtatctaaaattcataccaccagcacacaaggtctccggctagcagcagtaa
atggcatttagtacttacttagcccccaagcctggatgactgactatactgacttattattacttttagctatttgt
aggtagttacatctgaaaattgaccaggcacagtggttcatgcctgtaatctcagcactttgggagaccaaggcagg
aggatcagttgggccaagaatttgagaccagcatgagtaacatagcaagaaccatctctacaaaaaataaaaatta
accaggcatggtgatgcatgctacttgggaggccaaggtgggaggatcacttgagcctgggaattagaagctgcagt
gagctaggaaggtgccactgcactccagcctgggcaacagagcaagactcttaatctcttttaaaaaaaaatctga
aaaggaccccaaggattgaactttatctttacatttatctttacaaatccaggatcaaaagagagggtaaaggatca
cttggggagtttagaagtggcagaagtatctgtagaagccttacggtgtgaatgtgctggattgtgtgtgcccaccc
tcatggggacttccttggaggatgagggtacaccagcatgggcagcaaagctgtttgacctcaaggtggagatctg
agccacctggtcagtccatgcccagttaatttctatggaggtttggtaaagtaggttagggagttggatccaatgtt
cctgaagtttctgttggtaatatggcagggtcgggtcggtgtgggagggttggatcattctaagggcagtacaa
gacctaatcccaaaggtgagaagttcctctctgtggaggacagcatttagaactcaatacatacatggcttgttcaa
aaatggggaagagattagaaaaatttatcctaatgtttgcttgtcaaaccaagccattctctcagcaaagtagtgaa
acccttacataagtcctttgaagcctagcagcagtatcctactcaaacacaaaccaccaaaaaaaaaacaaaaaaaa
aacaaaacctccttggggactcagatgtgaacctctcatggaaaattcagtaccatgtgctttttgtagcaggtagg
atcacctgctgtttggaaattaactttttttctgacatctttttgaccgaactctgcatgtgcctcttgagaaaat
aatccaaattcttgctttcttcacttccagttttgctttatctttgcatcatgctctgcagtttacagacaagcat
aatgggtgagagttccagtaaattggctggatcatatttcttagattgagtcatgactgaggaacttgtttgggaac
aggaagcagcccatgaaaatggctgcacatagtaacctgccagattgaagaaaccggaccactttctagtggaaaga
taaaagggcagaaaaatggttctataactcagggaatggtaaatttgtgaactagggttttaacttgttgaataata
cgtctttgtgtgtatttgggcttttttatgctgttaaaagtctctagttattcaagataagggaaaggaaaacttgg
attcgtggtaactgttgctacctcttaaatgtctctgctgatgtatacaacatgttgctaggccagttatttttttt
aaggcactgtagttacatagaaataaacctggcaacatttacacttggcctcgataggctgtaaggccccttttgtc
tccagtattctgtgtttctgtattttaatcacctactttacacttactgtagcaacacaatcaagatagcaaatcag
tctaataaaccaaaagtactggaatgtgggaatagaaagaatgacctagaattcttgctgagaaaacaattggta
ttgctatattcttgtaatgcagtgtgagagaagccagagaagtaaataggcagatacatatctatgaaatgtaatta
gtcatcagcaagatgtattttaaaaacacatctgcttggtgtcattttgctttatctaataaggattacgactgcaa
ggcagagatttgtaaatgaaggagatctctgttgttttgttttgttttgcttttgttttgtttaagacagggct
ggagggcagtacatgatcatggctcactgcaaccttcatctcctgggctcaagtgatcctcccacatcagtttccca
agtagctgggactacagcagtgtctcaccatgtctggctaattttttaattttttttgtagagttgaggcctgtgttg
cccaggctggtctcaaactcctgggctcaagtgattctcacacctcagcctcccaaagagctgggattacaggtgtg
```

FIG. 2 (Continued)

```
agccaccgtgcctggctgttatttttatcaattcctcaaaattcaagcatgccctcaaatatttttgcagcctcatat
agctcttaatttggtttatattcatccagatggtaggatatgattcatgttccacctggttttcttcagaaatactt
agacagtgtctatggaaaaaaacattgaaccagatttagcttttaggtaaataatataatcacctgggaataatatg
aagaatgaaatgaaagaaagaaaaatataatcaagtgtaacttagactctgaatgctggtaactaagatttggatga
aggaaggatctcaggggaataacattaaaataagattttttttaaatggaaatacatgattttaagaaggataact
taagacattccaactttatactacatgaaagtaaaaagatcaaggatcagttttctctttggagcaaggctcagttt
cgctttctgttgagagttagtagtgtgtataattaattttttttaacagtttattgatgaaatttattttagaagg
aaatctcccaccaccttcctgtcattctcagggcaagatagagggtaggagagggaagggagactcgggggaatggg
aggtgcaagccttaattagacatttgagtgtctaaaagattacttttcatttcaaatactttgtctcagtttactga
atagctttaatttaggacagggattgtattatctttgctttatcttttccaatattttggatcatctaagcatgata
gatgctggtttattcaaggcactaaaattgacttgcaaaagacatatttaatatggattctgtgttcaagtcctttc
ttctttgtttatcctggtacaaagatgtttgttttaaagtggtatgagttaattgtccaacttcagatttccctaaa
atgtgtaacagattacccagttggcaaatgatgatatatattttttaaacatgaatatttctgttaggccagatggt
gatttaacatgaattgtccaacatttgtgtttcttatcaaattgtcttcttttgtctaagccaagctagcaacataa
tttggaacacactcaggaatcactaaaggacaagagcaaaaaaaattcagacaccaagtggcagacggcatttgctc
catatgccatgcaaaggctcctggccagtgctcgcatggcccttgggaagctttctcacccgttgtaagaaagtatc
tgtgcagtgctgtgcaacccatctacctgctttcctctctacccaaaccctacttatctaacactttgtactgtg
gccttcctccatgggggacttgcacttcctcaaagccctggatttctgtgcagaagagcagtttagttcttcctta
ggcacttcccttcctcctgtccagtgtcatgttcttgtttgttatgggctccacccagacgattatttcctcttag
atgatgtgtgagccttgcagagagctgggtcatttgtggaataaatcatgtgcccagtcacacggctccttacagga
aatggttggtgcatattagcttagcacaaaatacagtagtgagcttgtggtccccaacagtgagtcttcagttaact
tctgctgttttttttttttttttttaacataaagctttgaatgtttcatacagtatcaaatctctgcaggattttg
cctgctgaaacagatgtgaaaatctgagtagcacagagtatgacattaaggccataacaataaacctattgttgctg
cattctaaatttgatcaagatgtctgttttgggaatccaaaatagttgcttcaaatttagctttttcttttatga
agcagttttgttttgttttgttttgagacctctcatagcaagaaaaaacattacataaacttttttttgagacaagg
tctcactttgttacccaggctggagtgcagtggcacgatcttggctcactgcagcctcgacctcctgggctcaagca
gtcctcccaccttagtcccccacgtagctgggactacaggcacatgccaccacgcccggctaattttgtattttta
gtagagacagggtttcaccatgttgcccaggctggtctcgaactcctgagcacaagcgatctgcccgcctcggcctc
ccaaagtgctaagattataggcgtgagccaccatgcctggccacataaatataaacttaaaaatacacaggaaaacc
tttcagaacactttgaaacctattttggtcctattacgattgcactgaatgtccccagcctaatgaagagcaatta
gatgtcatttggtggcattcttggtggagacagtaagctagggccgcaggagctgcttagtctcccagggtccagca
ttgtttcaggtaacgtgaacaggatgctcaagagctagtctaaataatgcttcatgtcttattttcctgtttgttg
ataaggattcataaagatgtctttttctggtcatgtcaaggaaattcaaataaaaaacattgaattggtttggagc
tgtccattgaagggtactcacagcaggaattgagtggcaattgatgtgtgtgtgtatgtttgtaaacatttata
ttagagtgtatgcaaatgtatatgggcgtgcccactgccatcaccattaccccaccaacagtaacaaaaccaccat
caagagcaatatccactaaaacttctaatttgcttattaatttgctttattatttgtaaataattcagaatctctga
gatcaaaatcctttttattacaacatgttaatagtagtctaattcagacctgccctgaggaagaaccaagcaatga
agctgtccatgattttagaagttaattggctcattctttctgaccatctaggtagtcccaacattatttaggctcc
ccctagttaggtccacaacctcattattatccattggcctggactttggtctcgcttatacagcaagtagtagagcc
tatcactgtcaacatgtaaacatttgcatattttacatttatagagagatacttttcacgtgcctcatttgatccac
taacatctgtatgcttgggtaggatggaataattaaacaatgtatagctaaagccatccaaacccctcaaatattat
catctgatgggaaggaaaagggggggaaaggaaattaaatagttatttcaattcttggcatgattgacactgacaat
tataaaattccattcaatattttcttccagctcatgagggttggttgtaaggatactttgcaagtcagatttatgagc
agaagatgtttgcaacctaaattgcttcagttgcatgaaaaagtcacaaccttttactgattttatcctgggatct
ccttaacaagaaaaacctcaggcccaggaagtctagggtgaggcagggatgtgtcaaagtacacttttccccacgt
acagggacaagtatttgagtttctttgattgactttgcaaagagctttgcacactttgcacatcacttcttgagatg
ggtgggaacatggactgcctattttacagagttcaattaagatcgcaggatcatgcattcctttcattttggtgct
```

FIG. 2 (Continued)

```
agtacctagaagatgggaacatattgaacacttaataccttgcttgggcagatagctccagtttgcagaaagtctag
acaggataccctgctatgtatctagatttactgagaagaagcggcccaagctaatcagaattttaaagtaggtttct
cagctgggcgtggtggctcacacctgtaatcccagcactttgggaggccgaggcaggcagatcacttgaggtcaggg
gttcgagaccagcctggccaacatggcgaaatcctgtctctactaaaaatagaaaaattagccgggcatggtggcac
gcacctgtaatcccagctattcaggaggctgaggtgagagaactgcttgaaccctggaggcggaagttgcagtgagc
tgagattgtgccactgcactccagcctgggcgacagagcgagactccgtctcaaaaaaaataaaataaagtaggtt
tctctatacctttgaattttctgtctcccatgataaacctttgggtaaacatgtccatcagaatggaaacaaatcatt
ttttaaaatagaaattattctcatacctattttagtgggaatcccctgagaagatagccatgtatagtcgactgaa
tgctctgtggttgctattttgttgctcttggccaggaaactgatctaggtgacctacagacttaatctgacctgcag
actggccgcttcatactaccaagattccaaagccaagtgtatatacagtcggcccatgcagcctctggttccatgat
gcaaccaatggcagattggttcaaaaatatttggaaaaaggccaagcacagtggagtggttcatgcctgtaatccta
gcactttgggaagctgaggcaggaaaatcaatggagcccgggaattcaagaccagcctgggcaaaatggcaagacgc
catctctacaaaaagtaattagctgggcttggtggcatgtgcctgtagtcccagctacttgggaggctgaggtggga
ggatcacttgagcccaggtgaaggctgcagtgagccatgattgcatcaccacactccagcctgggtgacagagtgag
accctatctcaaaatgagtaaataaataataaaatttcaaaaggaaaaaagtggaaaaaaaacccgaaaaaataaca
atacacacataaaatacagtataacaactatttacacagcatttacactttactaggtattgtaagtaatccaggga
tgagttaaagtatataaagggatatgcataggttatttgcagcaaatgccatgccatttataatagtgtaggctca
tggctaataaagcatgaacccgactgaagctgcctgggtatgtgtcttgttcagccactttctggtagtatctttt
ttcttaacctcagtattcttatactgtataacaggaatgttttctctgtataaggctgttttgaggaatagtttcta
tatgtaaagtacttagaacagtgcatagcataggaagcccttaatagatactggcttaaagataattaggtatgt
cctagtgaggtatacctaactacaagtgctactttaactatgcctactttgtgtgctttacaatatatattgttcaa
ggctagaataatgagccccatgagcagggtttcatagcatttaagattccaacgccaaccttcaatcatggacacag
gtggcctgtgccatctagctagctgcgctgcctccaggctgggtggcctgctcctctgttggataaaaatagcctga
ctcctcactgaaacaaccaccatgttatttgcgtccttgggaagctgaaagtaatagaactctaagtctggcgttgc
cagctgtcagcagaatgaaatgcaaagtgtgacgtgtctacactgtacccactggccttcaagtcccaactcccgtt
ccccatcttgattttttttccattctcaaattaattatttcccctataggtgatttgtggaatggaaacagatttag
atttcctacctatttagattttttccaaagactaaaattacaaatcagaaaaactgctattgacacattttttggttag
gaaaatctggatgtggttcctatgcctagcctagtcatataaattctctcccatgtatctttttgtgtgtgtgaaa
cagggtcttgtcacccaagctggagtgcagtggtacaatcacagctcaccatggccttgacttcctgggctcaagca
atcctctcacttcagtctccctaatagttgggactacaggctcgtatcaccacgtgcaactaatttgttttgattttt
gggtagaaacaggtgtcactatggtgcccaggctagtaactcctgtgctccagcaatcctcctgccttggcctccca
aactcctgggattacaggcctgagtcaccaagctcagcctctcctcatcaaaaccattccctctttgtaagattctt
cctatgtcttaaaacttaataccttaatccttccctggagccatagttttatttatttatttatttattatgaga
cagggtctcactttgttgcccgggctggagtgcagtgacacgatcatagctcactgctgccatgacctcctggactg
aagtgatcctcctacctcagcctcctgagtagctgggaccacaggtgtgcgccaccacaccagttgttgttgttgtt
gtttgtttttgttttggtagaaacagggtctctccatgttgcccaggctggtcgcgaactcctgggctcaagcaatc
cacctgcctcagcctcccaaagtgctgggcttgtaggcgtgagccaccgcacctgtccctgtctgcttttatttat
ttttttttgagatggagtcttgctctgttgcccaggctggagtgcagtggtgcgatctcagctgactgcaacctctg
cctcccaggttcaagccgattctcctgcctcagcctcctgagtagctgggattacaggcacgtaccaccacacccgg
ctgattttttgtatttttagtagagacgtggtttcaccatgttggccaggctgatctcgaactccagacctcaggtga
tccacccaccttggcctcccaaagtgctgggattacaggcatataggtaagccacagagataagagtagcaagcagt
gatggggagaagataatctagtgtaggaaagatggaaagaatggtgatatttcacaactgctagattgacactttaa
cttgagagttatccctctataaactggatatttgctgagcaaagtttaaagaaaactccatgtattcagtaatgttt
tccagaccccacttctcttatataagccagtggcttagagtgcttgctctaatttctatattccattaaacaagggt
gggatttcttctcattcaaaccatttgtgactttgccctttagtgacctctaccatcacctatcattaatgatcca
agtgattagaatggatggctatgtgtttgtaggttgtttgttgtctttaatgaatagattcattgaatggaattaac
tgtgctcttctagaacattggatctgtgttctcatttagattgtatttgtaatctccccacttcccaccatcaacag
```

FIG. 2 (Continued)

```
tggcataatgtgaattaatttatgtggtatctgtcatttaaaaaacatgagctctctccttccttttttttgtcttaa
acatagGACATGGATTTGATTGACATACTTTGGAGGCAAGATATAGATCTTGGAGTAAGTCGAGAAGTATTTGACTT
CAGTCAGCGACGGAAAGAGTATGAGCTGGAAAAACAGAAAAAACTTGAAAAGGAAAGACAAGAACAACTCCAAAAGG
AGCAAGAGAAAGCCTTTTTCGCTCAGTTACAACTAGATGAAGAGACAGGTGAATTTCTCCCAATTCAGCCAGCCCAG
CACATCCAGTCAGAAACCAGTGGATCTGCCAACTACTCCCAGgtacagagtactcagttcttgggaaagttatggca
ggtttaaggaaacactgagcaaggaattaaaatatctggatttgagttccagctttgcctttcttttacttaaccott
gtcaaatctactttccaacctcagcctcctgatgagttcagtacctaacctgagttcagtacccaacctattgatct
taacagtgttattgtgaggattgggaagacttaagttacaccaaagagttttgtaaagtatagaaacatcctgtaag
gatcaagtagcagcaacagaagtagtagcaggagaaccaagtagcagggattactggcgttactgtgtgtggcaagc
actgttttaagaacatatactgactgatttaattaacacaactatattaattagttaccattatcctgttttatct
acgatgagcaactgaagctcacaaaggttaaataatttgcccagatcactcagaaaattggaggagctaagatctga
acccatgtggtctagttcaaattgtgcatcaaagtgatctctgaaataagataaatatttacttaacttgattataa
atattttatgaacatcaattattgaatatttagcttggcaatggaatatttaaccattttttgttttcctttgtgtca
ttcccttttatcagGTTGCCCACATTCCCAAATCAGATGCTTTGTACTTTGATGACTGCATGCAGCTTTTGGCGCAG
ACATTCCCGTTTGTAGATGACAATGAGGTGAGGTATAAAATAACCTGGTTAATAGAAAAACTCCATCATAACTATAA
AATAACAATCTATTCTATGTAAGTCCCGTCAATGAATCTCCATTTAAAAGAATAAAAACATTTTTAGGAGGAAATTT
TTTAACCAAGGAAATACTCTTGTCAAGGAAACCTTAGCCTATAAATAACTTTACAATTAAGAAAAAAAAAAACCCTT
CACACAATACAAAACCAAAACCATTGACTATTGCATAGCCAGAAACATGGACAGCATAACCATGGAAACAAATAACC
CATTTGCTGCAAGTATCTAAGAGGTTTGGTGAGTAAAGAGCCAGCTGGGCAATAAACGAAGACTTGTTCAGTTAACA
ATTTTAATAAATCTGTTTTATCTAGTACCACTGTGCTAGATATTATATAAACTAAATCCTAAAGATTGTACTTACGC
ATTTTAAAGTTTACTTTCAAATGCTTAAGCTGAAACAGACCAGCAAATTATAAATTTGAGTCAGTGGGGTAGGAAAA
AAAGATTTGTTATTTACAAACGGGGTCATGACTGGTTAGTAAGTAGAGAGACACAGAACTGCAGCTGATTCCATTTT
GTTTTGTAGTGGTGCCTTAGAGCTTACTCATCCCCTGTTGGTGGAAGACTCATAAATCAATGCCTTATCAATTTTAG
GTTTCTTCGGCTACGTTTCAGTCACTTGTTCCTGATATTCCCGGTCACATCGAGAGCCCAGTCTTCATTGCTACTAA
TCAGGCTCAGTCACCTGAAACTTCTGTTGCTCAGGTAGCCCCTGTTGATTTAGACGGTATGCAACAGGACATTGAGC
AAGTTTGGGAGGAGCTATTATCCATTCCTGAGTTACAGGTAACTAAAATAGAATGTAATACTGGAGATTTTTTTTAT
ATTCAGTGCCTTTAGTCATTCTGATTATTTATATACCACCTATTTATAGGAAGGATTGGAGGGTGCTATTAACTTA
```

FIG. 3

Natural antisense sequence (BU656954.1): SEQ ID NO: 3

```
AACAGACTGGCGGCGCGCGGAAAACGCGTCACGTGACGACTGGCCCCGCCTCTTCCTCTCGGTCCCATATTGAACT
CGAGTTGGAAGAGGCGAGTCCGGTCTCAAAATGGAGGTAAAACCGCCGCCCGGTCGCCCCCAGCCCGACTCCGG
CCGTCGCCGTCGCCGCCGGGGGGAGGAGGGCCATGATCCAAAGGAACCAGAGCAGTTGAGAAAACTGTTTATTG
GTGGTCTGAGCTTTGAAACTACAGATGATAGTTTACGAGAACATTTTGAGAAATGGGGCACACTCACAGATTGTGT
GGTAATGAGAGACCCCCAAACAAAACGTTCCAGGGGCTTTGGTTTTGTGACTTATTCTTGTGTTGAAGAGGTGGAT
GCAGCAATGTGTGCTCGACCACACAAGGTTGATGGGCGTGTAGTGGAACCAAAGAGAGCTGTTTCTAGAGAGGA
TTCTGTAAAGCCTGGTGCCCATCTAACAGTGAAGAAAATTTTTGTTGGTGGTATTAAAGAAGATACAGAAGAATAT
AATTTGAGAGACTACTTTGAAAAGTATGGCAAGATTGAAACCATAGAAGTTATGGAAGACAGGCAGAGTGGAAA
AAAGAGAGGATTTGCTTTTGTAACTTTTGATGATCATGATACAGTTGATAAAATTGTTGTTCAGAAATACCACACTA
TTAATGGGCATAATTGTGAAGTGAAAAAGGCCCTTTCTAAACAAGAGATGCAGTCTGCTGGATCACAGAGAGGTC
GTGGAGGTGGATCTGGCAATTTTATGGGTCGCGGAGGGAACTTTGGAGGTGGTGGAGGTAATTTTGGCCGTGGT
GGAAACTTTGGTGGAAGAGGAGGCTATGGTGGTGGAGGTGGTGGCAGCAGAGGTAGTTATGGAGGAGGTGATG
GTGGATATAATGGATTTGGAGGTGATGGTGGCAACTATGGCGGTGGTCCTGGTTATAGTAGTAGAGGGGGCTAT
```

FIG. 3 (Continued)

```
GGTGGTGGTGGACCAGGATATGGAAACCAAGGTGGTGGATATGGTGGAGGTGGAGGATATGATGGTTACAATG
AAGGAGGAAATTTTGGCGGTGGTAACTATGGTGGTGGTGGGAACTATAATGATTTTGGAAATTATAGTGGACAAC
AGCAATCAAATTATGGACCCATGAAAGGGGGCAGTTTTGGTGGAAGAAGCTCGGGCAGTCCCTATGGTGGTGGT
TATGGATCTGGTGGTGGAAGTGGTGGATATGGTAGCAGAAGGTTCTAAAAACAGCAGAAAAGGGCTACAGTTCT
TAGCAGGAGAGAGAGCGAGGAGTTGTCAGGAAAGCTGCAGGTTACTTTGAGACAGTCGTCCCAAATGCATTAGA
GGAACTGTAAAAATCTGCCACAGAAGGAACGATGATCCATAGTCAGAAAAGTTACTGCAGCTTAAACAGGAAACC
CTTCTTGTTCAGGACTGTCATAGCCACAGTTTGCAAAAAGTGCAGCTATTGATTAATGCAATGTAGTGTCAATTAGA
TGTACATTCCTGAGGTCTTTTATCTGTTGTAGCTTTGTCTTTTTCTTTTTCTTTTCATTACATCAGGTATATTGCCCTGT
AAATTGTGGTAGTGGTACCAGGAATAAAAAATTAAGGAATTTTTAACTTTTCAATATTTGTGTAGTTCAGTTTTTCT
ACATTTTAGTACAGAAACTTTAACAAAATGCAGTTTCGAAGGTGTTTCCTTGTGAGTTAACAAGTAAAGAAGATCA
TTGTTAATTACTATTTTGTATGAATTTTGCTAAAGTTAACTGTAAAGAAACACCTGCTGACTTGCAGTTTAAGGGGA
ATCTATTCTCCCCATTTCCAAACCATGATATGAATGGGCGCTGACATGTGGAGAGAATAGATAATTTGTGTGTTTGC
AATGTGTGTTTTAGATAAATAGGATTGGGTATTTAAATTAGCATTTGTGAATTTAATAGCATTAAGATTACCTTCAA
ATGAAAAAAAATCTCAAAATTTCTATTTGGTTTTTGTGCATTTTCTTTTAAAATGTAATCATATGATTTTAGTGTGTT
AGACTTGCTGAGTCCTAGCTGTGTTTAGAACATCTCTATTCTACATTTACCTTGGTCAAATTTGAACTGCTGCCATAG
GTTTTGGGTGTAAAGAATGTTTACTGCCCTCCATTTAAATTCTGAAAAGGGATGGTGGATGTTTTCCCTCTCCTACG
TTAGAAACCATTCTTAAAAACTTTTGAAAATATAGAACCATTAAGCCTGCTATATCTGAGCAAATTAGTGGGTACCT
TTTTTTTCTTATTTAAAGCACAAGAGGCCCATAAATCTTGAGTTACTTTAAATTCTTTTTTTTGATACAAGTTTTCAGA
GCAAGAGAATAAAAATCATGTGTTATTAAACCCCTAACTGGCTGGCATGCTTTCCTGTTTGTATTCTATACATTTTG
CTGGATGAAACCAAGGATAGTTCAGGTATAATTGTCCAAAATAACCTAACTGCAGCAGAAATGTAGCACAGTTGCT
TAGTACAGGCTTCTCACTTCCTACAGACCTGAATTCAAATTTGGATAGTCTGAGTTCTTAAATTCCCAAAGAACACA
CTGTTATTTCTTGTGTATATTTCAACATAAATCATGTTGTTACCAATTTGTTTGGAAGGCCCTGGTTGAGAAGAGTTT
TAGTTAATAAGGTCATATATACATATATTAATATAAACCAATGTCTACTGTTTTGCTCCAGCTAGTGCTTACAGTTTC
ATTCGAGCCCTGAGTATGTGCCCTGCTGTTACTCTCTTTGGTAGTTGAACGTTGAATTCAAGTCTTTTGTTTTAAGA
AGTACTAAGCAAACAAGCAATAAAAAGGGGAATGGGGTGTGCTAGTGTTTGAATATGCTCTCTTGTTGCTCTAATT
CTGTGCCTCTGTGCATTAATATTTGGATGCATGCAATGCCAGCATGGAAATTGGTCTTCACACATACTGCAGTTTTC
CAGAAACATTCACAAACCAATAAATGTAACAGACATTCCATTTGTTAATGGGCATATATGTGAAAAGCAGTGTAGA
AAATAGGCTAATATTAGAAAATGGTTAAGTCCTAAATAACTTCAAGTGTGGTTATATAATGGACACTGTCAATGTT
CATAACTTAAACCTGGGTACCTGGTCAAAATAATGCTTGGGAAACATTAAAATTGAGCTAAATTGTCTCAAGTTCTT
TTATTCATATAAATAAAGTTTAAAGGAATGGGGGAGATTAACATTTCCTGTTTTATGTTTGTGAAATTGTTTGACAC
AACCTTGACAGTATCCTTTAATGGCATGAGGTTAATTGTACTGTTAACCAACTTTCTATGTTCTGGAACTAGTATTAT
AGTGAAAACATTTACAGTAAGTTGATGTTTACAACCTATAAGCAGGTGAAATCTGTGTATGTGACCTGTTTATAAG
TTGTATTAGCTTAGCTCTTGTGAACAGTGTGGAAAAGTAAGCCATGAGGAGAGCGATTTAACCACCTTTAAAGGAC
CTAAGATGTGCTTTTTAAGCACAGTGTGGATCACAGAAACTCACTAAGACAGGACTTCAGCAGCCTTTTGTGTTTG
GACAAGTCAGCATAAATAAAGAATGACAAGGCAGCAGCAAGAGCTTCAACTACAGAGAAGTGAAGGCATAAGAT
ACTATGATGATAGTGAGCAACTTTCCAAAAGCTAGTTAAATCTGCTTATTACAACTGAAATATCGAAGAAAGTCTA
GCAGGAAGGAGCTCTTCGCCTTTTGGAACATCAATGAGAGATAGTTGCCACAGTCACTAGGTCTAGCATTTAGACC
TGCAAGGAAGGGCAATAAGCATTAGGTAAGGCTTGAATTTGAATTTTTTCACTAATTAAAGAGTAATTTTTTGTAA
AGCAAGGTAAGAGTAATCTTTTTGATTTGCAGGTTGAATGAGAACCCTACTTGCCTAAATGAGGAATGTCTTTCCT
ACCATCTAAAATACGAAGGTTTCTGGCTGGGTAAGGTTTGTAGTTGACAGTAAAACCTGATGACACCATTTGTTTC
```

FIG. 3 (Continued)

CCTGCAAGTCTACATTACATATTTCACAACTTTGTCCCTCTCTAGTAGGCACATTGGAAAAATTCTTCAACTGAAAAC
TACCTTGGTACCATGTCCTACACGTTTTAAACCTTAGTTTTAAAAATTCCCCTGCGAAATAGCCATAAGTATTCATAT
CAAGTCAGTTGTGACTCCTTGTGTATACAATTCATTTTTTGTGTCTTCAGGGTAAACTCAATTTTTGGTAAAGTGGTT
TCAGCTTTTGTGAAAACCGTTTTGGTGTGTAAGCATGACACACAACAGACTCAGTAAGCTGCCCATCCTCATACTA
GGAAAACACCTTCAAAGGAACATTAAAAGTTACCAGGGCCAGGCACAGTGGCTCACGCCTGTAATCCCAGCACTT
TGGGAGGCTGAGGCAGATGGATCCCAAGTCCAGGAATTTGAGACGAGCCTGGGCAACATAGTGAGAGCCTGTCA
ACAAAAAATAGAAAAATTAGTTGGGCTTGGTGATACACATCTGTAGTCCCAGCTATTTGGGAGGCTGCCTTGATAT
CAGGCAGTCGAGGCTGCAGTGAGCTGACTGCCCCACTGTATTCCAGCCTGGGTGACCCCATCTCAAAGAAGAAAA
GTTACCAGATGTCATGGGTAAAGGTTGGTCTTCAAGTGGCCTCATAAGTTGTCTTGCATTTAAATTCAGGGAATTC
ATTGGACCAATAGGTTACATTTTCGTTCCTTTTTTGTTTTGGTTCATCTGTTAAGCAGTGGGGGCCTAATTACTGCTC
CTTTGTAAAAACACATTTTCCCAAAGAACACTGAATTACCGTTCAAACTGGTTGTTGATGGGTAATAAGGGCTGTTT
TTGCTGCCCCAAAAGGGCTTAACAATTTAGTCGGATAGTTTACTTAAAAAAAAAAATCCTTTGGAGACATACTGAA
AATGCAAACTAGTTTCTAAATTATCAATTCCCTACATGAAGAAGCAGTTTGCCAGAGTTTAGTCTCAGAAAATGACT
GGTTGGCTCTATTTAAATCAGAACCCAATTTCTACGCGTGTTGAATAAGGTAACAGCCTTTGATGAATTTCCTTCAC
AACATGGTTTTAGTGAAGCAAACATTTTTTTTTTAAGGGCATTGTTCTTTCTAGTTTATTTCTTTTTATGAAATAAAAT
TATTTTATTTAAACAGTTCCATTGTCGTTTCTGAAAACTACAGTATTCTCAGAAGTTGTAGCAGCAGTAAAAAAAAA
AAAGTTGTTATATAAGTGATTGGGGCAGATTTAACTGATTTTGTTAAACCAATTTGTAAGTTACTGCTTCTAATATT
ACACTTCTAAAAAGCTGAATTTATACTCATGTCCTAAAGGAGAATATGTGGTAATAAAGTATATTTGTTAAGTAACT
AATTGAAATAGGCTTGGTTTTAAGAGTTCCAGTATATAATAATCACAAATTGAAACCTGACAGTATCTTGGGAGTT
CCAGTAATGTCACAAATTAGTGAATAAGCATGCCAGTGTGCAAGGGTAATGTAAGGATTGTTAGCCTATCTAAATA
TTCAAAATTACTTTAAAACTTAAGTATGTTTTCTGATTTTTAAGAATTCAGAAGTGTTCTGTAATGGATTCAGATGTT
TCATTTGTAGTATAATGAAATGTTTACAGAAAGATAACTTTTTCATTAAAATATTTTTAGAAATGTGTGTGTTGTTTT
GTCACTTCACAATGTTCATGTGACTTAAACACTATAGGTGAATATTTTGACTTATTTTACCAGTAAGTAATAAAACA
ACAGGAAACTTG

FIG. 4

| Sequence ID | Sequence |
|---|---|
| SEQ ID NO:4 | UAGGAAAGACAUUCCUCAUUCCUCAUUUAGGCAA |
| SEQ ID NO:5 | UUCUGCUACCAUAUCCACCACUUCCAC |
| SEQ ID NO:6 | T*A*G*G*A*A*A*G*A*C*A*T*T*C*C*T*C*A*T |

FIG. 5

| Sequence ID | Sequence |
|---|---|
| SEQ ID NO:7 | GCCUAAAUGAGGAAUGUCUUUCCTA |
| SEQ ID NO:8 | GGAAGUGGUGGAUAUGGUAGCAGAA |

SEQUENCE LISTING

```
<160> NUMBER OF SEQ ID NOS: 9

<210> SEQ ID NO 1
<211> LENGTH: 2884
<212> TYPE: DNA
<213> ORGANISM: Homo sapiens
<300> PUBLICATION INFORMATION:
<308> DATABASE ACCESSION NUMBER: NM_006164
<309> DATABASE ENTRY DATE: 2010-08-04
<313> RELEVANT RESIDUES IN SEQ ID NO: (1)..(2884)

<400> SEQUENCE: 1
aaatcaggga ggcgcagctc ctacaccaac gcctttccgg ggctccgggt gtgtttgttc      60
caactgttta aactgtttca aagcgtccga actccagcga ccttcgcaaa caactcttta     120
tctcgcgggc gagagcgctg cccttatttg cgggggaggg caaactgaac gccggcaccg     180
gggagctaac ggagacctcc tctaggtccc ccgcctgctg ggaccccagc tggcagtccc     240
ttcccgcccc cggaccgcga gcttcttgcg tcagccccgc cgcgggtggg ggattttcgg     300
aagctcagcc cgcgcggccg gcggggaag gaagggcccg gactcttgcc ccgcccttgt      360
ggggcgggag gcggagcggg gcaggggccc gccgcgtgt agccgattac cgagtgccgg      420
ggagcccgga ggagccgccg acgcagccgc caccgccgcc gccgccgcca ccagagccgc     480
cctgtccgcg ccgcgcctcg gcagccggaa cagggccgcc gtcggggagc cccaacacac     540
ggtccacagc tcatcatgat ggacttggag ctgccgccgc cgggactccc gtcccagcag     600
gacatggatt tgattgacat actttggagg caagatatag atcttggagt aagtcgagaa      660
gtatttgact tcagtcagcg acggaaagag tatgagctgg aaaaacagaa aaaacttgaa     720
aaggaaagac aagaacaact ccaaaaggag caagagaaag ccttttttcgc tcagttacaa     780 ctagatgaag agacaggtga attttctccca attcagccag cccagcacat ccagtcagaa      840
accagtggat ctgccaacta ctcccaggtt gcccacattc ccaaatcaga tgctttgtac      900
```

```
tttgatgact gcatgcagct tttggcgcag acattcccgt tgtagatga caatgaggtt    960 tcttcggcta cgtttcagtc acttgttcct gatattcccg gtcacatcga gagcccagtc   1020
ttcattgcta ctaatcaggc tcagtcacct gaaacttctg ttgctcaggt agcccctgtt   1080
gatttagacg gtatgcaaca ggacattgag caagtttggg aggagctatt atccattcct   1140
gagttacagt gtcttaatat tgaaaatgac aagctggttg agactaccat ggttccaagt   1200
ccagaagcca aactgacaga agttgacaat tatcattttt actcatctat accctcaatg   1260 gaaaagaag taggtaactg tagtccacat tttcttaatg cttttgagga ttccttcagc    1320
agcatcctct ccacagaaga ccccaaccag ttgacagtga actcattaaa ttcagatgcc   1380
acagtcaaca cagattttgg tgatgaattt tattctgctt tcatagctga gcccagtatc   1440
agcaacagca tgccctcacc tgctacttta agccattcac tctctgaact tctaaatggg   1500
cccattgatg tttctgatct atcactttgc aaagctttca accaaaacca ccctgaaagc   1560
acagcagaat tcaatgattc tgactccggc atttcactaa acacaagtcc cagtgtggca   1620
tcaccagaac actcagtgga atcttccagc tatggagaca cactacttgg cctcagtgat   1680
tctgaagtgg aagagctaga tagtgcccct ggaagtgtca acagaatgg tcctaaaaca    1740 ccagtacatt cttctgggga tatggtacaa cccttgtcac catctcaggg gcagagcact   1800
cacgtgcatg atgcccaatg tgagaacaca ccagagaaag aattgcctgt aagtcctggt   1860
catcggaaaa ccccattcac aaaagacaaa cattcaagcc gcttggaggc tcatctcaca   1920
agagatgaac ttagggcaaa agctctccat atcccattcc ctgtagaaaa aatcattaac   1980
ctccctgttg ttgacttcaa cgaaatgatg tccaagagc agttcaatga agctcaactt    2040
gcattaattc gggatatacg taggaggggt aagaataaag tggctgctca gaattgcaga   2100 aaagaaaac tggaaaatat agtagaacta gagcaagatt tagatcattt gaaagatgaa     2160
aaagaaaaat tgctcaaaga aaaaggagaa aatgacaaaa gccttcacct actgaaaaaa   2220
caactcagca ccttatatct cgaagttttc agcatgctac gtgatgaaga tggaaaacct   2280
tattctccta gtgaatactc cctgcagcaa acaagagatg gcaatgtttt ccttgttccc   2340
aaaagtaaga agccagatgt taagaaaaac tagatttagg aggatttgac cttttctgag   2400 ctagttttt tgtactatta tactaaaagc tcctactgtg atgtgaaatg ctcatacttt    2460
ataagtaatt ctatgcaaaa tcatagccaa aactagtata gaaaataata cgaaacttta   2520
aaaagcattg gagtgtcagt atgttgaatc agtagtttca ctttaactgt aaacaatttc   2580
ttaggacacc atttgggcta gtttctgtgt aagtgtaaat actacaaaaa cttatttata   2640
ctgttcttat gtcatttgtt atattcatag atttatatga tgatatgaca tctggctaaa   2700
aagaaattat tgcaaaacta accactatgt acttttttat aaatactgta tggacaaaaa   2760
atggcatttt ttatattaaa ttgtttagct ctggcaaaaa aaaaaatttt taagagctgg   2820
tactaataaa ggattattat gactgttaaa ttaaaaaaaa aaaaaaaaaa aaaaaaaaa    2880 aaaa                                                                2884

<210> SEQ ID NO 2
<211> LENGTH: 31261
<212> TYPE: DNA
<213> ORGANISM: Homo sapiens

<400> SEQUENCE: 2
aagggacagg ttggagctgt tgatctgttg cgcaattgct attttccca gagcggcttt      60
```

```
gtctttggat ttagcgtttc agaattgcaa ttccaaaatg tgtaagacgg gatattctct    120
tctgtgctgt caagggtaag agttgcgagt gtagattaga atttctgttg cttttagtct    180
gttagtaatt ttttgctttc agctattatt tctcccctga gtactttata tatgtttcct    240
tttcagttga gaatttgcct caatttctta acatgttccc cctcttctgc aggggcagag    300
agtggaacgc ttgcgtttca aaacacttgc taatttctgt gaattgttat aaaagtgaaa    360
agaagtttct gctcatcctt tgtagaaact ttaaaagtag atatttatat ttctaacttc    420
ttttgtaaat gaatttagg aaaaaaattg gaattcaagg aaatgtgtac ttgatgtaca    480
gtaaatacgt ttatgctgtt aaatgtaaag ttttcggtta attccaaaga tctattgtaa    540
agttttaagt tatggacaat gtattaattg tgcttttttc cccctttaaa gttgtttgtc    600
ttgaactttt ccccagtctt cattgggatt gtattcttct ggttccaact agtgaagaat    660
taaattgtac cttccgattt atttaatagc tgctgttcaa gagttatcta taggaatgct    720
tgtttgactg aaggatatat gataaaaatg aactttagtt tttctgattt ccggaattgt    780
ctacagccct ctattatttt tgaattttc tttctttgct gtgtaatata acattcctta    840
tacaaaaatg cgtgaaacat atgtaccgca ttaagtgtgt attttccaat tacgtttgat    900
aaaaataact gcttttctac ctttgtaatc agacatcgat ttgcatattt gaaaacagaa    960
aaagaacaag aaaatttaga attgattttg tttatgattc atattagatt gttgtcatcc    1020
ataaagattt gaacagagtc aaacattttc ttgacctttt gtcaaaaaaa actctccagg    1080
tgtgaagtgg tagtaggata tagttttca ccttctgtgc agaggatgtg ttgataaaca    1140
gggcagtaag gagagcctta gattcagtat ctccattagg tggaaggaac catccattac    1200
tcttttcaag ggtgtcttgg agagataaag cactttccta gatgagggat gaagttgata    1260
ttgaaataga ccgatgagat tattttaag tcaaacaaaa gaaaaatagg acaggcctct    1320
catctcctga atgaatgtta agcaaagaac aacttgactt tttagatatg tgaaaaatct    1380
cttgagaggt tgtggaagca gcatgtagga ggataaatgc ataactcaca tcagtctttt    1440
acgcattaaa aataacttgg gccattttga atctttctt tcttgccctg ggttcttata    1500
agcaatgttg gggggaaaac tgactctgtc tttaggatta ccaggaaaag ttgaaagcca    1560
aatgcatcat ttttcttaat atttgttttt attgaggata aatcatgttt aacaaagctg    1620
catgaaaaaa aggaacccaa caagtacatt ttttttctg ggaatttcct ctgtcctgac    1680
tgaagacatt taagggggt tttgtgtcaa tatttcctcc ttaactgttc ctcaagcctg    1740
ggttaacttt tcagtatgca ggaagaattt ggcactaaga taataataga taagttactg    1800
ggcacgtccc tgggtgccag acataattgc ttcacatgca taattttaca gtaacctcac    1860
gggaaatatt attatccctg gtttccaggt tgggaaaacc aggcataata gttagatcag    1920
gcattaggtt aggaaaggtt aggagagagg catagagaaa ggccaggacc tgctaaggtg    1980
accatactat tgagtggcca aggtagcatt caaacaggtt tgactcctgg ggcttctaa    2040 tcaccacttc cagactgtac caaaactcct taaactctaa ataggaagaa aagctcacac    2100
tttaaaaagt gggtaagttg agatttgcct attctggggg aaggagaggc cggaatataa    2160
aagattaatg tctgcagctt ttccatttag caagacattt aatcactgta tgtgacgtgg    2220
ggaggtggac cttgttaaat acagggagag tgaatacaat ccatcaatgg tacccactgt    2280 ggtccttta aggaagacac agaggcctcg gtggattcaa tttagaaagg caggactgtt    2340
ttttgttttt tgttttttt tttttttgag atgaagtctt gttctgttgc ccaggctgga    2400
atgcagtggc ctgatcttgg ctcactgcag cctctacttc ccgggttcaa gtgattctcc    2460
```

```
tgcttcagcc tcccgagtag ctgggattat aggcacccac tgcccggcta attttgtat   2520 tttagtaga  gatggggttt taccatgttg gccaggctgg gctggtctcg aactcctgac   2580
ctcaggtgat ccacccgcct cggcctccca agtgttggg  attacaggtg tgagccactg   2640
cgccagtctg tttcttaata taataatagt tttaaaaatt tctgatgttt ggcaatgtcc   2700
aagattctgc ctcacatttt tcagaaactg cctttttct  taattaaatc tcttagctac   2760
tggagtcttt gcctttgttt gccttgctac ttggtacatt tcttctgttc cattggctct   2820
ttttgttttg aagtagtgct caaaaataag tttggtagta agaatatggt gaagagtgtg   2880
acagacaggg ttaaaccagg ctgaaggaaa gagagcagaa tggggaaaat ttgagttgaa   2940
aacagctagc agaaagctga tggcgcaaat tcaaccctaa tctcatgttt tggcacttct   3000
gaactatagc aagcataagg gctcaactct tatctagttg aagcttactt gggtctttga   3060
gaatagtaca tctcaaaatt aaacactttc ttagtcctta ttgttaagtt gttttggaa    3120 ttattgtctt atttgtctga attaagtgtg ctgcaggact tataggatct gatggatgat   3180
ttgcctaaaa gttggtccag gtcaacctca gggcatttaa atgcttggtc cagccacttt   3240
ctgaaagttg actgaaatat gttgcacagc agggtagagg aggacaagtt tactagatgt   3300 cattttttaac ctgcttgtct tcatctctga ctgtagaaat gtatattcat tataagtttg   3360
ccacaaatag agaatagagt ttattctttg atcatctaat ttctaggagc tattgaaatt   3420
tcactgctac ctgcttttaa ataagcgcca acaaacattt attaaaaggg ctttaaggta   3480
taggccaaga tttattcaat tgctaatggt atgttttctg taaatgaaag caaaaatatg   3540
ttcaagtgta taatattaaa tattaacatt cagaaacttg gagaaataca gatggctttt   3600
ttttttgaga cgcagtcttg ctctgtcgcc caggctggag tgcagtggca tgatctccgc   3660
tcactgcaag ctccacctcc cgggttcacg ccattctcct gccccagcct cccgagtagc   3720
tggtactaca ggcaccccgcc accacgcctg gctaattttt tgtattttta gtagagatgg   3780
ggtttcactg tgttagccag gatgatctcg atctcctgac ctcatgatcc gcctgcctca   3840
gcctcccaaa gtgctgggat tacaagctta agccaccgcg cctggcctag atggatttct   3900
tgtaccagac tataccctag acatgaaaac aagactgtta aacaaaatcc tgtgctacct   3960
aaagtttgag ccttctgtgt gtcagttct  gccataataa ataactctta actatgatta   4020
ttaagtatat taagaacttt gagtaggga  ggcacgttta atcattcgtt tttacggcat   4080
atgtactata atacctgtgt gttgcaaatc ctggtattta aaagtctttt tgtgtatttg   4140
agcatgtaag tttatttggt ccaaactgct ggtactagta aagacaagtc cagggcataa   4200
gtaggactta cagcaccaag ttcgtctttt tttttgaga  cagagtctca gtcggtcacc   4260
caggctggag tgcattggta cagtctgggc tcactgcacc ctccacctcc cgagttcaag   4320
cgattctcct gcctcagcct cccaagtagc tgggattaca agtgtgtgcc gccacgcccg   4380
gttaattttt gtatttttag tagagatgga gtttcactat gttggccagg ctgatcccga   4440
cctcaggtga tgtgcccacc ttggtctccg aaagtgctgg gattataggc gtgagccact   4500
gcgcctgacc tccaagtcca tctttcaaag gctctgttga taattgactc ttgagagtca   4560
ttacagtcca tcaacagcct gtattctgaa tatttgtttt taattctaag acaatgctaa   4620
atagccattc caaataaggt gagaactgag actttagggc ctgtattatc agctgtacac   4680
tgacaagctc tgaactctat tgcttttca  aatcagagaa gaaaaatgag taagaaaaga   4740
aaaatatgga tcacttaggc tttgatgcct cctctgagtt tatagtgttt accttctgta   4800
```

```
ttacttaggt gatcctctct aatggcattt taaatctctg ttgatacttg tcttacttat    4860
gtatctgttt ttttttcctc tatagtagat agaatttata gatatatatg tattttaaag    4920
taagatacaa tttacgtacc ttacaattta cccatttaat ctaattcagg gttatgcaac    4980
cctatgaatt tagtagttta ttcatagagt tatgcaacca tcactgtaat caattttcaa    5040
caccctcaaa agaaacccca tatccattag cagtcacttc ccatttcccc tcaactctcc    5100
tggcccctgg taactactca gttatttct gtacctatgg atttgcctat tctggacata    5160
tcatgtaaat ggaatagcat gtaaatggaa tcatacagta tttatccttc tgttgctggc    5220
ttctttcaca gcaatatgtt ttcaaggttt aaaaatgttg caacgtatat caatagcgtc    5280
attccttttt atggctgcat actattccat tgtatggcta taccacattt tatttatcca    5340
gttgatgatc atttgagttg tttccacttt ttatgtttct gtttgtttct tacagcagtg    5400
gttctcaaac tgttgtatat tagactcacc atcagtattt aaaaaactaa tgcccaggcc    5460
atatccctca tgaaatcaaa atctctgggg gtggggccca ggcatcacta tttttttaaag   5520
attctgaggg gattctaacg agcagtcagg tttgagagcc agtgccctag gcagcagtc    5580
cacaaccttt ttagcaccag ggactagttt tgtggaagac agttttttcca tagaaggagg   5640
tagaggatgg tttcaggatg aaactgttcc acctcagatc atcaggcatt agattgtcct    5700
aaggagctgg caacctacat cccttgcata ctcagtttac aacagggttc cggcttctct    5760
gataaactaa tgctgctgct aatctgacag gaggtggagc tcaggcggga atgctcgcct    5820
actgctcacc tcctgctgtg cggcctggtt cctaatgggc cactgacccc tccgcagcca    5880
gcaggtgggg acccctgccc taggggaccc acctcagtgc ttggtatcca ttgaagtata    5940
tagtgattta gaaaatctgg ttaggatgtc ttatttaaat catgaaagca agtgcttttg    6000
tctttgatca ttgcccttca cagccttaca gttaacacct acattcagga actgtgtttc    6060
aaagtgcctg gcgagtgttt gaaactcact aaatatatat aacctgggct cattaaaccc    6120
ctccagaaga tttgggtaac tttgttatga aagggcttcc ctgaagtggg tcagcaggat    6180
tgctctgtgt ttttttcagga atgtggcctg tgataacttg caatctagat tatttggaaa    6240
tagcactgag agaagccagt gaggacagaa tgctcagaag cttgggatag gtgttgaaca    6300
tcctggaggc caggacggaa cactgtctta ctctaggaag ctgtgttcct gggcctcatt    6360
atcttcctcc gttaaaaaca aaagacttaa atctccacag cagctttcag caacttcatt    6420
ttttggttct ctgtatctgc ctgataaagt cccactttgt agtggctccc acttatattt    6480
acctgaatgg cttttgggtt gacatatttg gaaactgggg ctaacttcca aactgttggc    6540
aacttgtgtg tgggtgtgcg tgccacagca cagcagtccc acttgagaga cttgatggtg    6600
tggtggtggt tgggggcttt ctgaagctgg cttagcccca gccctataca cccaccccac    6660
agatggtggg aacaagccca aagagagtg ggtaactctg tccactgtgg cctccacagc    6720
caaggttgcc aggcagagct cgcaaggccc aattccagtc ttgtctttga ccgttgcccc    6780
tttgtgttgg gggggtgtat ttagtcacct ttctggaagc atgctttct aattctagtc     6840
atcagtagtt tgttgcttta agattttgaa aatggtatcc tgttatttta cttaggagtt    6900
tcgtattgaa tggtgtacat aatgtgatc aagtacctca aaacagaagg acttcagtta    6960
agatttaggc tctatgcaac atacacttct tgcatttct cattcaatgt cctttccttt     7020
tttttttttt tttttttgc aagaatgtag ctgacattca gagtagatta gtaccttcaa    7080
tgtctgtgtg aaagaaatga ccttaatatg aggacaatat tgactgtgta tttagggggc    7140
ccactgttaa ggcatataga attttgcttt atttcagacc tgacaatctc ttgtctgctc    7200
```

```
tgcttccgca taaaattata atactgcaca tggatgtaaa acccaaccta ttccctgcct    7260
gagggactag aatagaggga agaatgacta tagttctttg ttgccttttg tgaaggtaac    7320
aggcacagag gtatgatgca tgatggaatt atatacctct tcttgaggtg tttgagggct    7380
gactaaggac ctgtactttt tttttggttt gttttgcagt actggggcca gggagccttg    7440
ctgttgtgtc tagagagtgt tgaagaacca tgaatatttc gcaaaagaa aataattttt      7500 ttaaccatta aaattcctgg tagtgacttc ctctggcaag taaaaaactc tcattttcct    7560
taaaaaatga gagttttta cttgcaatag gaaaacttgc caattttca agttatttt       7620 attcttgatg attctcaatg agacataatt aaaatacaca tagaaaaaac aaccgtaggc    7680
caggtgcagt ggctcacacc agtaatccca cactttggg aagtcaaggt gggaggatca     7740
ctagagacca ggagtttgag atgagcctgg gcaacatatt gagacactgt ctcctcaaaa    7800
aattaaaaaa attagctgga tccagtggtg cacacctgca attgtagcta tttgggaggc    7860
taaggtggaa gaatagcttg agcccaggag tttgaaggtg cagtgagcca taatcatgcc    7920
actgtactcc agcccaggca acagagtaag atcatgtctc aatgaaaaaa agaaaaatca    7980
accctagtgg actggaacag ggctggttta cttgtgtca gctgcagtgc ccccactcgc     8040
caacccacat gttcttctcc tgctggttcc caagcagaga ccagaaccaa gaatgagaat    8100
catcctgtgg gtgcaggttg tatcttatcc tccagacaca gcacttcacc ctctgttaga    8160
aacttcttta ccacactgcc tgtttggtga atccttagg gcagtgactt ccaaactgtg     8220
atccaggggc caccccttggt gggaggatca ggaaggaggg ggaatgtatc ttaagaaaag   8280 ttggggaag ctcatatctc ttctcgttga tcctgagaag taaagtcttt cctcctcaga    8340
gagatgcggg tagacatgac tcgcctagat agaagctcat tcatctccct cccttctgcc    8400
tctgcaggac tcttggaagt ctgggtcccc gggagtatgc ggctcttgct ctgtgctaca    8460
ggtttccaaa gttcacttga taacagtaca attgtgctgt aaattgtgca gtaatggaga    8520
ctgaggaaac aattagtctt tcatcttcat tcatgttacc agctcacttc ctatggtgtg    8580
aaaagagcca gactttggag ttaggagaca tctgaataca gacagaactg gcaagattat    8640
ggggaagaaa agggaaaagt aatgaatatt ttcaaagagg ttaagccatt tggccaggac    8700
aacactgctt gcaggtagca gaactgggat tttgactgtc cataatccct attctctgct    8760
tgttttactc cttccctctc ttcttttcttt tttcattgtc taatgaccta cagacattct    8820
gtcagctgct aaagaatgag ggactccttt ataagattg ataggacagt gtcgctactt    8880
aaggagttcc ttccatgtgg accagtgggg gcgctgttga cgcatgggc tggacttctc    8940 tttggagcag agtcctgttc cacggatcgc tgtgacaagc agaaagtgcc cacccacc     9000 tccatacaat tcctaatgct cctgggtgat acaaccgccc cagtggaagc acggtggtgc    9060
atggacttct agagaccatt tgaagccagg acattgctgc ttgttcttag gaaatggcag    9120
aatattactt tcttgttttt tgtagggaag cctgccatct caccaggtgg cagcttgttt    9180 ataccttta tcctaacctg aagcaggtga tgggacagag gtcatcgaat ataatgaaag     9240
tgccacaaag gtagagtctg ggtatatttt atttatgcag gtagagtgac ttgtccagat    9300
cccttcacac agagcaacat ttaatatggt aattgttact gctgaagttg gccatttctc    9360
ggacctacag ctgcaaggaa ttggtaacaa aaggataaac taaacattgt tactatttta    9420 atttcaagg agatgaagtt aaaatcatat atgtcatatc tctctgggc ttagccacct     9480 tttctgctgg gcacttttg aagaagtctg aatactgaga taggagagta aagggggaa     9540
```

```
agtaagtttg cccacttctc atccttttc tgaccatcag cctgagggaa gtaactagaa    9600
tccgctaaga aaattcactt aatcagcagt tgattgattg ttatattgtc cacattgcaa    9660
aattctttaa aggatatttg aagatattat cacatttgtt ctcttacaat ctattgtatt    9720
gtttatttga aggggtgagt gttaatagtt cttaagatat cgtactttat ttccggtagc    9780
atatccaaga aataatttag aagtattgtt aatgggaatg atgttaaata attttctat    9840
gactagtagt tgggacatat atgatataaa acatggtatc tttgttactt aagtaatttg    9900
aactctaacc ccatatatct taggtagaca atgaaaatac tgaattgtta gtctaaataa    9960
tatacacgta ctcattccgc aaatatttat taggtatcta cacaccctag gaatctttca   10020
gggcatgaag ctgtttttaat cttccaagat aatgcagcac gtatccccct tgagggacat   10080
ttgttttttca aattgctcct ctgtgtctcc tctgcttagg atatgagttc ctctaagact   10140
gtatttttaat cttttgtgta attctgatgt ctagcgccat gcctggtgct tacgtaatag   10200
ttgctcagtc agtttgaggg tgagtccatt aactgccctc taggagcttg atatttaata   10260
taaactagtc tgtgatacat gacaatgctg tgacagtgca gatgagaaaa tgtgacttct   10320
aactggggtg ctcagagagg atatcctgga ggaactgcca ttttaactag acttttcttt   10380
taagcaggta gattttgttt ggttcaggct tcagctggaa gcccaagcaa tggtgcagat   10440
atgagctgga ctatgacaga ctattgggcc agtggggctg acaaggttaa cttgggggtt   10500
gccatagagg gccttcagtg ctcatgtgca ctgtttcaag tttgtacagg gcatctggaa   10560
accatggaag aagattctgg aaagggcagg gcaggtaaac tggatgtgga taggaagtta   10620
ctgtggcagg tgaattggaa gatggacagg ttggaggcag ggagatggtg agcgggctcc   10680
tgccaaggtg taggtctgag cattgttgtg acggcttagt tggtttgaca tcagcacaca   10740
gattgaggat ctgtcattgt aactctaaat tgtatccttg ttagacatgt aaaaataact   10800
ttttagagcc tccgttttta aggagggaag tggattgtgc tcaagcttgc atgctccgct   10860
gttcctgtgc tttaaaaata ctcatccacc agtgtggtca ctgatgaaag gggaggaaaa   10920
actagccaga agttgccatt tgcttaaag aatggattca tttcttcctc aaggtggcac   10980
agagagagtt tctctcttt tgcccctctc ttagattgat ttactatttt tagtaaattc   11040
taacagtctg atccttgctt ccaattacaa tgattagcaa tatttgccca agacaagaaa   11100
aaacaatttc ctctcttttc tctcctatga gcttttcctg tgagcccaa gcagacagat    11160
gtggacatct agcaatgctg ttaacaacag ctgcagtccg ttggactctc tgcaacactg   11220
ggcacggtac aaagtgctct gacaaactct tctgcccttt gcaatcctta ctacgccctg   11280
tgaggtgagg agtattcttc ctgttttgta ggtgaagaac tgaggcaaag agaggttatg   11340
tcattagatt tcacaatagg gtgtgttcc gtttcatcat ctttagattg atgttactgt   11400
gacatcatct tcctagaatt aacaaagtga actgggcaca ggaaatagca catggcacac   11460
cttcagcaaa tggtggttgt gatcatttc atcattccat ttcttcttga aaaaaatccc   11520
ttttttttt tttttttgag acagagtctc actctgtcgc ccaggctgga ctggtgtgat   11580
ctcggctcac tgcaagctcc gcctcccggg ttcacgccat tcttctgcct cagcctcctg   11640
agtagctggg actacaggca cgggccacca cgcctggcta atttttttgt attttttagta   11700
gagacggagt ttcaccgtgt tagccaggat ggtctcgaac tcctgacctc gtgatccgcc   11760
cacctcggcc tcccaaagtg ctgggattac aggcatgagc caccgcct ggcaaaaatc   11820
cctcgagttc cagtgtaaac actcacgccc ttttttgctg tttgctataa acctctcatt   11880
ctccttggtc ttcttgtcct tgtgtgaggt cctggttgtt gtggagactg aggtcttctg   11940
```

```
agacagaaaa ccaaccccat agcaggcctg gtgtgtgccc tagaatggca gaggccccac   12000
acgttgcccc ggctcctctg gaagaccctc cagcctgtct gctggattcc ttgtacttat   12060
gaggattgtt aaaccatctc ataggattcc tttccagact cagcccttca cttgtggcag   12120
catttcttac tctgaggttc tgggcctaga aacccagtgt ccataggcaa ggtctaggga   12180
cagagagagt ttgtagaaag tgggaatgca tcagtggaag gctaaatcca aacaggaact   12240
gagctggcct gggtggcttt gtccttttgc catcttcgta acccttttaaa ggctttaaga   12300 cacttctttt gtaataacta ccccaactaa atttggccag agctgtgaag ggaaagaaaa   12360
tctaagaccc ttgagggaga tgacagccga acgttttaca ttttaccac ctttgttgtt    12420 gccatgcaca gctgatacat aaacaagtaa tggcctcatc ttctattctt ttatttactg   12480
gttagaccca gaaccctaaa aggtagatgc ttctcatggt catttggcat ttgcaacagg   12540
agctgaattt attaatagta ctaatacctc atccttggac atccttgggt tgtccgatat   12600
ttttaagggg catttacatc ctttgttttt catatgaaaa acttttccgt aagggctggt   12660
atcatcttgg ccttccattg caggaacagc acagggaggt tcggtggcta ggccacagtt   12720
acccacgcag ctaggtagca gcagaggccc cacctggcac cccctggctt cctaagcaca   12780
tcgcactgtg cagcctccct gaggaagcct cgagtggata ggaactctgg ttctttaaga   12840
taaacctgag ttggatctca ctgtcaccat ttatcagatg gggcgatgtc ttcaggcaaa   12900
agtacttaac ctctctgttt ttgtttcctt actccaaaat ggtaatgatc atactactac   12960
ccacctgggt ggattggtgt gcatatgaag gaggtcatgg ggacaagtgg ttggaagagt   13020
gttgagcaca tagaaagtac aagataaatg gtggccatta tgttactact tagactatat   13080
catacttgtc tttatctggg cttagaatct tgacactgag atctttcatt ctcagatctt   13140
aatatgaaag cttaccaggt aaacactacc ccaacataat tatttagtgg gttcatacat   13200
gtgaaagcag ttgaaataca atttctgaac tccgggttaa tttatatcct tagttggaac   13260
aggtagtacc ctcccagcac ctaaggcctc tcacttctat ccattcttca gatgaccttt   13320
gcaataatca tggtaattga atagcatctg caccataaca ttgttgaata acatcaaaat   13380
gatccattta gccatcatga gccttcctag taattcagac tcacaccagt tctttcaggt   13440
tattgagtag cttttacaaa taattgctaa cagtacaaat actgtctcag gtattttgga   13500
agggtgaatt ttcccattga tttcagtgta tctttaggag gtaatttgca aaaccgaaga   13560
gtttggttcc gtcaaagtca cccctaagga gtgtggagga ccacattgta ggtttatact   13620
gcactgtccc tcatgcttga aatttggctc atgcaaccaa ggaactgaat ttttaatttc   13680
gttaaatttt gatttaaatt ttaaaacaga aatagtataa aatattttc tgttaaatat    13740 accttgtagt gttggcaaga ctacatttcg tgttaccatg ctgggtaaga tttcttgtag   13800
tgtgtattgt gttttgtcac ctcgttaata attttcttat tttggttgca tgttaaaata   13860
attttggata tattgggtta aataaatata ttgttaaaat taaattcact tgtttatttt   13920
tttgttggtg aggctaggct actaaaaaat ttaaaattac ccatgtggat tgcattatat   13980
ttctattagt gctgctttag ctgcaagtag cctatttaaa aaaaatcatt attttcagac   14040
ttatggactt catagaatca gaggtattta gaggaaagga tcttgggggt cacctaatcc   14100
agctccaaca ttttgcaagt gataagacca aggccagagg ctacaataaa atgactgacc   14160
tcctcccaga tggggactgg atcccagtgg ctttatagcc tttgccttgg atcctggttt   14220
tacttggaaa catagcagac atcagagctg cagagaactt ctaccagatc cggagtgaag   14280
```

```
aaaatgcctt atttatttat ttatttattt atttatttat ggagaccggg tattgctgtg    14340
gcctaggctg tagtatagtg gcagaaacat ggttcactgc agcctcaacc tcctgggctc    14400
caggatcctc atgcctcaac cttctgagta gccggggcca caggtacgcg ccaccacgcc    14460
tggctatttt ttttttttctc ttttgtagag actgcgtctt ccatgttggc caggctgata    14520
tcaaaactcc tgggctcaag tggtcctcct accttggtcc cccaaagtgc tgggataaca    14580
ggtgtgagcc atcatgcctg ttttggcagt ttttaggggc ccacgctaat ttgagccag     14640 gtttgcgctt gataatgtaa tgctggaggc tgggcagggg acatgatctg cctgaaaggg    14700
ctgagaactg ggaggctctt attcctatag tattgagagc aaaggcacag tcttacagaa    14760
ccacacaata ttcagagctt gtgggttgga aaggaaagt cctctgaaaa ataaaaaaaa    14820
gagtacagag gccagaggcg gtggctcatg cctgtaatgc cagcactttg ggaggcccag    14880
gcaggcggat cacctaaggt gaggagatcg agaccagcct gaccaacatg gagaaaccct    14940
gtctctacta aaaatgcaaa attggccagg catggtggcg catgcctgta atccaagcta    15000
cttgggaggc tgaggcaaga gaatcgcttg aacccgggag gcggcggttg cggtgagctg    15060
agatcacgcc attgcactcc agcctgggca acaagagtga aactctgtct caaaaaaaaa    15120
agaaacagag tacaggtcag acattgggca atttctcat aacaatttca taggccatta    15180
atttggttac agacttgaat agcacacaac agttctctaa gggtcagttt ccaaagtaat    15240
tcctaatatt taatgaattt ttaagtgata gaaattgcag taggaaagtc tagcttgaaa    15300
tctaatttgt gttaggttga ccaggtgaca accacccacc cctggattct gctcagttag    15360
gtcagacctg gggccagttg cccatttagc atctcaggcc tcaggatcct catttataaa    15420
cctggggttt gaactgcggt ctccacgatc actgtcagct ctccttagtc agttggttgt    15480
tctaaatgta gtttagtggc cagtaaacac ctgttcctga gtgatacatc tttaaggagc    15540
cggtagatgg gtcaacctgg ctggacttgc ttttttcaagt ctgccttgtc tattagaaag    15600
gctgagctta ctgattttgc ctgtcacgtt tgagtgttcc tgagactttg cccagcctcg    15660
gtcttatctg cgggtacccc agcctctgca ttccttgccc ctacaaaatg tgctgccagt    15720
tccaaaggca caaatgaaaa ttagcttggc tggagcatgg ctaggcacac accagtggtt    15780
aaagaaatgc tgtttgctgg ctgacacttc tggagtggaa gtttattctt ttttctttt     15840 tttttttttt tttgcggggt ggggcagagt tttgctcttg ttgcccaggt tggagtgcaa    15900
tggcacgatc tcggcttgga gcgatcttgg gtcaccataa cctccgcctc ctgggttcaa    15960
gcgattctct tgcctcagcc tctggagtag ctgagattat aggctcccgc taccacgccc    16020
ggctaatttt ttgtattttt agtagagaca gggtttcacc atgttggcca ggctggtctt    16080
gaactcctga ccttcgatcc cacctgcctc ggcctcccaa agtgctggga ttacaggctt    16140
gagccacggc gcccggcctt tattcctttc tttggcctca tttttattgt taagagatag    16200
tgggaagggc ccaattttga aatgatcctg gaattaatgt aggaggcctt gtataagcag    16260
ttaatgtgta tttattgagt gggtaccctg tgccaatatg atacaaggtg tgaaggacac    16320
atgagttggg aaaggcatgg ggaaatgcac gctcacactg ctggtgcgag tgtaaaaggt    16380
acagtctcta tgtagggcta tttggcagta tatactcttt gacccagcaa ctccactttt    16440
aagtatttat cttagggata ccctcacaca tttatgaaat gatttatata caaggatatt    16500
cattatagca atatttgtaa tgcaaaaag aaacaaagt cagatggggg actgattaaa     16560
taattatgtt attaagtaat actgtttcag tacatctgtg taatgaaata atgtccagtc    16620
attaaaaata gtgaggcaaa gtctgggtgc agtggctcac gcctgtaatc ccagcacctt    16680
```

```
gggaggctga agccggagga ttgcttgaga ccagcctggg caacatagtg agaccctgtc    16740
tgtacaaaaa aaaaaaaaaa aaagtaaaat attagccagg catagtggca catgcctgta    16800
atctcagcta ttcaggaggc tgaggtggga agattgcttg agcccaggag gttgaggctg    16860
cagtgagctg tgattctgcc actgcactcc agcctgggca acagaacaag accctatctt    16920
agaaaaaaag aaaaaaaaga aaagggaca acttacaact ctgtgccctg atgtagaacc    16980
atctccaaaa tatattaaat gagtgtggga tactatgctt atatgcgatt gtgtgtattt    17040
aatggcttcc taagaaaaca aaaaaaaacc tgatactagt gattgccttg gaggagggta    17100
actgggaaat tacttttgca acttttaaat cttataccat gtacacctgg tatctatttt    17160
taaaaagcca ttttcatgcc ctaaatgagt ttagtcagac catagtaaga aaatcctgta    17220
agacatacaa agtatggggt aattactggc tttatgggaa gactgatttc aatgcaaaac    17280
tctccctatg caagggagtt gtcctgattt caatgctaag ctctctttag gcaagttacg    17340
ttggcctgat ttgcctgtta agtcgtatgg ggcaggcaag tctgagtgtc cagagggcag    17400
acctttaact cttagtttcc tgccttggga gaaggcacag ggctaaagtg gtttccagaa    17460
cgtgtctgtt gtggtgtgaa caccaaggag cagtggacaa gcttcccagg ctcaaggtca    17520
gaaggtctgg actggagtcc tgcctctgct acttggtgaa tatgtgattt ggggcaggtt    17580
gcttaatccc cgaagcctca acgtgttcat ctagaaatga agattacagg ctggacgcag    17640
tggctcatgc ctgtaatccc agcactttgg gaggctgagg caggcagatc atctgaggtc    17700
aggagttcga gaccagcttg gccaacatgg caaaacccca tccctactaa aaatacaaaa    17760
attagctggg catggtggca ggtgcctgta atcccaacta ctcgggaggc tgaggcagga    17820
gaatcacttc aacccaggag gtggaggttg cagtgagctg agattgtgcc actgcactcc    17880
agcctaggca acagagtgag actctgtctc aaaaaaaaaa aagactacaa tacctggccc    17940
aactccctca tgctactgta gtgaggctca aatgagatag cacccatgaa cactcctgta    18000
aaccatgaag tatgcaaaca ccaggtgtaa tagaagctgt taggtacctg tgaggccagc    18060
agacaagagc aagagatgct aatttaaaaa gaattaaggt gaagcaaaga tcttttccct    18120
ctgccaaata acttggcaag agttgtaaaa ttagaaaagt agacccttag tagtttgata    18180
atcctttgac ctctgaccct gcacaaatga tctcacccct tagacctgtt cccttatttg    18240
caaaacaaga ggggctgtct gggtgattcc tgtggtccct tccagttgta gcgttccgtg    18300
acagtgtggc attaacagta attcccatct tggctgagat ggatgagtca tactaactga    18360
aaagtcaaaa tacgaggaag aagtctcttt atgtatgaga atttccttg agctagagac    18420 tcagagcctc ttggggagga gatgagggaa acattgcca ccaccaagaa gggagacgaa    18480
ggatgtataa agagaatgga gatgtattta ctttttttt tttttttttt ttttgagac    18540 agagtctcac tctgtccttc tggctggagt gcagtggcac gatcttgggt tactgcaatc    18600
tccacctccc aggttcacgc cattctcctg cctcagcctc ccaagtagct gggacacagg    18660
cgcccaccac cacgcccagc taattttttg tgttttagt agagatgggg tttcaccgtt    18720
agccaggatg gtctccatct cctgacctcg tgatccgccc gcctcggcct cccaaagtgc    18780
tgggattaca ggcgtgtgcc accgcaccca gccgagatta tttacttctt gtgtgttctt    18840
gccatctcca tagcctcctt tgctttcaaa tgcccacttg ggctgggcct ttggaaaata    18900
gatttaaccc ttgtttattg gaaggatatt cacacagtag gccagttata cactttgtgg    18960
cagtcgttac ctcttctgtg aggtcttcct gtgcagattt agtggcacct cctccatgct    19020
```

```
gcctgggctt ctacttgctt ctcatcactt tgtctcataa ctcagatcag agactgtgtc   19080
ttactcatct ttgtatccct ggcatctgag ggggtggtat ctgatgggta gatggattag   19140
tgatccactt agggtattta cactaatctt gttgatcttg actactacct ttataaccac   19200
caccattcta caagttttaa cttttttttt tttttgagac agagttttgc tcttgtcacc   19260
caggctggag tgcaatggcg cgatcttggc tcactgcaac ctctgcctcc ccgggttcaa   19320
gcgattctcc tgcctcagcc tcccgagtag ctgggactac aggcacccgc caccatgcct   19380
ggctaatttt tttgtatttt tagtagagac ggggtttcac cgtgttagcc aggatggtct   19440
caatctcctg atcctgtgat ccacctacct cagcctccta aagtgctggg attacaggcg   19500
tgagccaccg cacccagcaa ggatcttttt tttttttttt aaagctaagt gttttataca   19560
tataataata ttgttaataa aatgtatcta aaattcatac caccagcaca caaggtctcc   19620
ggctagcagc agtaaatggc atttagtact tacttagccc ccaagcctgg atgactgact   19680
atactgactt attattactt ttagctattt gtaggtagtt acatctgaaa attgaccagg   19740
cacagtggtt catgcctgta atctcagcac tttgggagac caaggcagga ggatcagttg   19800
gggccaagaa tttgagacca gcatgagtaa catagcaaga accatctcta caaaaaataa   19860
aaattaacca ggcatggtga tgcatgctac ttgggaggcc aaggtgggag gatcacttga   19920
gcctgggaat tagaagctgc agtgagctag aaggtgcca ctgcactcca gcctgggcaa   19980
cagagcaaga ctcttaatct cttttaaaaa aaaatctga aaaggacccc aaggattgaa   20040
ctttatcttt acatttatct ttacaaatcc aggatcaaaa gagagggtaa aggatcactt   20100
ggggagttta gaagtggcag aagtatctgt agaagcctta cggtgtgaat gtgctggatt   20160
gtgtgtgccc accctcatgg gggacttcct tggaggatga gggtacacca gcatgggcag   20220
caaagctgtt tgacctcaag gtggagatct gagccacctg gtcagtccat gcccagttaa   20280
tttctatgga ggtttggtaa agtaggttag ggagttggat ccaatgttcc tgaagtttct   20340
gttggtaata tggcaggggt cgggtcgggt gtggggaggg ttggatcatt ctaagggcag   20400
tacaagacct aatcccaaag gtgagaagtt cctctctgtg gaggacagca tttagaactc   20460
aatacataca tggcttgttc aaaaatgggg aagagattag aaaaatttat cctaatgttt   20520
gcttgtcaaa ccaagccatt ctctcagcaa agtagtgaaa cccttacata agtcctttga   20580
agcctagcag cagtatccta ctcaaacaca aaccaccaaa aaaaaaacaa aaaaaaaaca   20640
aaacctcctt ggggactcag atgtgaacct ctcatggaaa attcagtacc atgtgctttt   20700
tgtagcaggt aggatcacct gctgttttgg aaattaactt ttttttctgac atcttttga   20760 ccgaactctg catgtgcctc ttgagaaaat aatccaaatt cttgctttct tcactttcca   20820
gttttgcttt atctttgcat catgctctgc agtttacaga caagcataat gggtgagagt   20880
tccagtaaat tggctggatc atatttctta gattgagtca tgactgagga acttgtttgg   20940
gaacaggaag cagcccatga aaatggctgc acatagtaac ctgccagatt gaagaaaccg   21000
gaccactttc tagtggaaag ataaaagggc agaaaaatgg ttctataact cagggaatgg   21060
taaatttgtg aactagggtt ttaacttgtt gaataatacg tctttgtgtg tatttgggct   21120
tttttatgct gttaaaagtc tctagttatt caagataagg gaaaggaaaa cttggattcg   21180
tggtaactgt tgctacctct taaatgtctc tgctgatgta tacaacatgt tgctaggcca   21240
gttatttttt ttaaggcact gtagttacat agaaataaac ctgcaacat ttacacttgg   21300 cctcgatagg ctgtaaggcc ccttttgtct ccagtattct gtgtttctgt attttaatca   21360
cctactttac acttactgta gcaacacaat caagatagca aatcagtcta ataaaaccaa   21420
```

```
aagtactgga atgtgggaaa tagaaagaat gacctagaat tcttgctgag aaaacaattg   21480
gtattgctat attcttgtaa tgcagtgtga gagaagccag agaagtaaat aggcagatac   21540
atatctatga aatgtaatta gtcatcagca agatgtattt taaaaacaca tctgcttggt   21600
gtcattttgc tttatctaat aaggattacg actgcaaggc agagatttgt aaatgaagga   21660
gatctctgtt gttttttgttt tgttttttgct tttgttttgt tttaagacag ggctggaggg   21720
cagtacatga tcatggctca ctgcaacctt catctcctgg gctcaagtga tcctcccaca   21780
tcagtttccc aagtagctgg gactacagca gtgtctcacc atgtctggct aattttttaaa   21840 ttttttttgta gagttgaggc ctgtgttgcc caggctggtc tcaaactcct gggctcaagt   21900
gattctcaca cctcagcctc ccaaagagct gggattacag gtgtgagcca ccgtgcctgg   21960
ctgttatttt atcaattcct caaaattcaa gcatgccctc aaatattttt gcagcctcat   22020
atagctctta atttggttta tattcatcca gatggtagga tatgattcat gttccacctg   22080
gttttcttca gaaatactta gacagtgtct atggaaaaaa acattgaacc agatttagct   22140
tttaggtaaa taatataatc acctgggaat aatatgaaga atgaaatgaa agaaagaaaa   22200
atataatcaa gtgtaactta gactctgaat gctggtaact aagatttgga tgaaggaagg   22260
atctcagggg aataacatta aaataagatt tttttttaaat ggaaatacat gattttaaga   22320
aggaataact taagacattc caactttata ctacatgaaa gtaaaaagat caaggatcag   22380
ttttctcttt ggagcaaggc tcagtttcgc tttctgttga gagttagtag tgtgtataat   22440
taattttttt taacagttta ttgatgaaat ttattttttag aaggaaatct cccaccacct   22500
tcctgtcatt ctcagggcaa gatagagggt aggagaggga agggagactc ggggaatgg   22560 gaggtgcaag ccttaattag acatttgagt gtctaaaaga ttactttttca tttcaaatac   22620 tttgtctcag tttactgaat agcttttaatt taggacaggg attgtattat ctttgctta   22680 tcttttccaa tatttttggat catctaagca tgatagatgc tggtttattc aaggcactaa   22740
aattgacttg caaaagacat atttaatatg gattctgtgt tcaagtcctt tcttctttgt   22800
ttatcctggt acaaagatgt ttgttttaaa gtggtatgag ttaattgtcc aacttcagat   22860
ttccctaaaa tgtgtaacag attacccagt tggcaaatga tgatatatat ttttttaaaca   22920 tgaatatttc tgttaggcca gatggtgatt taacatgaat tgtccaacat ttgtgtttct   22980
tatcaaattg tcttctttttg tctaagccaa gctagcaaca taatttggaa cacactcagg   23040
aatcactaaa ggacaagagc aaaaaaaatt cagacaccaa gtggcagacg gcatttgctc   23100
catatgccat gcaaaggctc ctggccagtg ctcgcatggc ccttgggaag ctttctcacc   23160
cgttgtaaga aagtatctgt gcagtgctgt gcaacccatc tacctgcttt cctctctcta   23220
cccaaaccct acttatctaa cactttgtac tgtggcctttc ctccatgggg gacttgcact   23280
tcctcaaagc cctggatttc tgtgcagaag agcagtttta gttcttcctt aggcacttcc   23340
ctttcctcct gtccagtgtc atgttcttgt ttgttatggg ctccacccag acgattattt   23400
cctcttagat gatgtgtgag ccttgcagag agctgggtca tttgtggaat aaatcatgtg   23460
cccagtcaca cggctcctta caggaaatgg ttggtgcata ttagcttagc acaaaataca   23520
gtagtgagct tgtggtcccc aacagtgagt cttcagttaa cttctgctgt tttttttttt   23580
ttttttttaa cataaagctt tgaatgtttc atacagtatc aaatctctgc aggattttgc   23640
ctgctgaaac agatgtgaaa atctgagtag cacagagtat gacattaagg ccataacaat   23700
aaacctattg ttgctgcatt ctaaatttga tcaagatgtc tgttttttggg aatccaaaat   23760
```

```
agttgcttca aatttagctt ttttcttttta tgaagcagtt ttgttttgtt ttgttttgag    23820
acctctcata gcaagaaaaa acattacata aacttttttt tgagacaagg tctcactttg    23880
ttacccaggc tggagtgcag tggcacgatc ttggctcact gcagcctcga cctcctgggc    23940
tcaagcagtc ctcccacctt agtccccac gtagctggga ctacaggcac atgccaccac     24000
gcccggctaa ttttttgtatt tttagtagag acagggtttc accatgttgc ccaggctggt   24060
ctcgaactcc tgagcacaag cgatctgccc gcctcggcct cccaaagtgc taagattata    24120
ggcgtgagcc accatgcctg gccacataaa tataaactta aaaatacaca ggaaaacctt    24180
tcagaacact ttgaaaccta ttttggtcct attacgattg cactgaatgt cccccagcct    24240
aatgaagagc aattagatgt catttggtgg cattcttggt ggagacagta agctagggcc    24300
gcaggagctg cttagtctcc cagggtccag cattgtttca ggtaacgtga acaggatgct    24360
caagagctag tctaaataat gcttcatgtc ttattttttcc tgtttgttga taaggattca   24420
taaagatgtc tttttctggt catgtcaagg gaaattcaaa taaaaaacat tgaattggtt    24480
tggagctgtc cattgaaggg tactcacagc aggaattgag tggcaattga atgtgtgtgt    24540
gtgtatgttt gtaaacattt atattagagt gtatgcaaat gtatatgggc gtgcccactg    24600
ccatcaccat taccccccacc aacagtaaca aaaccaccat caagagcaat atccactaaa   24660
acttctaatt tgcttattaa tttgctttat tatttgtaaa taattcagaa tctctgagat    24720
caaaatcctt ttttattaca acatgttaat agtagtctaa ttcagacctg ccctgaggaa    24780
gaaccaagca atgaagctgt ccatgatttt agaagttaat tggctcattc tttctgacca    24840
tctaggtagt cccaacatta ttttaggctc cccctagtta ggtccacaac ctcattatta    24900
tccattggcc tggactttgg tctcgcttat acagcaagta gtagagccta tcactgtcaa    24960
catgtaaaca tttgcatatt ttacatttat agagagatac ttttcacgtg cctcatttga    25020
tccactaaca tctgtatgct tgggtaggat ggaataatta aacaatgtat agctaaagcc    25080
atccaaaccc ctcaaatatt atcatctgat gggaaggaaa aggggggaa aggaaattaa     25140 atagttattt caattcttgg catgattgac actgacaatt ataaattcca ttcaatattt    25200
tcttccagct catgagggtt ggttgtaagg atactttgca agtcagattt atgagcagaa    25260
gatgtttgca acctaaattg cttcagttgc atgaaaaagt cacaacccttt tactgatttt   25320 tatcctggga tctccttaac aagaaaaaac ctcaggccca ggaagtctag ggtgaggcag    25380
ggatgtgtca aagtacactt ttccccacgt acagggacaa gtatttgagt ttcttttgatt   25440 gactttgcaa agagctttgc acactttgca catcacttct tgagatgggt gggaacatgg    25500
actgcctatt ttacagagtt caattaagat cgcaggatca tgcattcctt tcattttttgg   25560 tgctagtacc tagaagatgg gaacatattg aacacttaat accttgcttg ggcagatagc    25620
tccagtttgc agaaagtcta gacaggatac cctgctatgt atctagattt actgagaaga    25680
agcggcccaa gctaatcaga atttttaaagt aggtttctca gctgggcgtg gtggctcaca   25740
cctgtaatcc cagcactttg ggaggccgag gcaggcagat cacttgaggt cagggggttcg   25800 agaccagcct ggccaacatg gcgaaatcct gtctctacta aaaatagaaa aattagccgg    25860
gcatggtggc acgcacctgt aatcccagct attcaggagg ctgaggtgag agaactgctt    25920
gaaccctgga ggcggaagtt gcagtgagct gagattgtgc cactgcactc cagcctgggc    25980
gacagagcga gactccgtct caaaaaaaaa taaaataaag taggtttctc tatacctttg    26040 aatttttctgt ctcccatgat aacctttggg taaacatgtc catcagaatg gaaacaaatc   26100
attttttaaa atagaaatta ttctcatacc tattttagtg ggaatccccc tgagaagata   26160
```

```
gccatgtata gtcgactgaa tgctctgtgg ttgctatttt gttgctcttg gccaggaaac   26220
tgatctaggt gacctacaga cttaatctga cctgcagact ggccgcttca tactaccaag   26280
attccaaagc caagtgtata tacagtcggc ccatgcagcc tctggttcca tgatgcaacc   26340
aatggcagat tggttcaaaa atatttggaa aaaggccaag cacagtggag tggttcatgc   26400
ctgtaatcct agcactttgg gaagctgagg caggaaaatc aatggagccc gggaattcaa   26460
gaccagcctg ggcaaaatgg caagacgcca tctctacaaa aagtaattag ctgggcttgg   26520
tggcatgtgc ctgtagtccc agctacttgg gaggctgagg tgggaggatc acttgagccc   26580
aggtgaaggc tgcagtgagc catgattgca tcaccacact ccagcctggg tgacagagtg   26640
agaccctatc tcaaaatgag taaataaata ataaatttc aaaggaaaa aagtggaaaa    26700 aaacccgaa aaaataacaa tacacacata aaatacagta taacaactat ttacacagca    26760
tttacacttt actaggtatt gtaagtaatc cagggatgag ttaaagtata taagggata    26820 tgcataggtt atttgcagca aatgccatgc cattttataa tagtgtaggc tcatggctaa   26880
taaagcatga acccgactga agctgcctgg gtatgtgtct ttgttcagcc actttctggt   26940
agtatctttt ttcttaacct cagtattctt tatactgtata acaggaatgt tttctctgta   27000
taaggctgtt ttgaggaata gtttctatat gtaaagtact tagaacagtg catagcatat   27060
aggaagccct taatagatac tggcttaaag ataattaggt atgtcctagt gaggtatacc   27120
taactacaag tgctacttta actatgccta ctttgtgtgc tttacaatat atattgttca   27180
aggctagaat aatgagcccc atgagcaggg tttcatagca tttaagattc caacgccaac   27240
cttcaatcat ggacacaggt ggcctgtgcc atctagctag ctgcgctgcc tccaggctgg   27300
gtggcctgct cctctgttgg ataaaaatag cctgactcct cactgaaaca accaccatgt   27360
tatttgcgtc cttgggaagc tgaaagtaat agaactctaa gtctggcgtt gccagctgtc   27420
agcagaatga aatgcaaagt gtgacgtgtc tacactgtac ccactggcct tcaagtccca   27480
actcccgttc ccccatcttg attttttcc attctcaaat taattatttc ccctataggt    27540
gatttgtgga atgaaacag atttagattt cctacctatt tagattttc caaagactaa    27600 aattacaaat cagaaaaact gctattgaca cattttggt taggaaaatc tggatgtggt    27660
tcctatgcct agcctagtca tataaattct ctccccatgt atctttttgt gtgtgtgaaa   27720
cagggtcttg tcacccaagc tggagtgcag tggtacaatc acagctcacc atggccttga   27780
cttcctgggc tcaagcaatc ctctcacttc agtctcccta atagttggga ctacaggctc   27840
gtatcaccac gtgcaactaa tttgttttga ttttgggtag aaacaggtgt cactatggtg   27900
cccaggctag taactcctgt gctccagcaa tcctcctgcc ttggcctccc aaactcctgg   27960
gattacaggc ctgagtcacc aagctcagcc tctcctcatc aaaaccattc cctctttgta   28020
agattcttcc tatgtcttaa aacttaatac ctttaatcct tccctggagc catagtttta   28080 tttattttatt tatttattta tgagacaggg tctcactttg ttgcccggc tggagtgcag    28140 tgacacgatc atagctcact gctgccatga cctcctggac tgaagtgatc ctcctacctc   28200
agcctcctga gtagctggga ccacaggtgt gcgccaccac accagttgtt gttgttgttg   28260
tttgtttttg ttttggtaga aacagggtct ctccatgttg cccaggctgg tcgcgaactc   28320
ctgggctcaa gcaatccacc tgcctcagcc tcccaaagtg ctgggcttgt aggcgtgagc   28380
caccgcacct gtccctgtct gcttttattt tattttttt tgagatggag tcttgctctg     28440
ttgcccaggc tggagtgcag tggtgcgatc tcagctgact gcaacctctg cctcccaggt   28500
```

```
tcaagccgat tctcctgcct cagcctcctg agtagctggg attacaggca cgtaccacca   28560
cacccggctg atttttgtat ttttagtaga gacgtggttt caccatgttg gccaggctga   28620
tctcgaactc cagacctcag gtgatccacc caccttggcc tcccaaagtg ctgggattac   28680
aggcatatag gtaagccaca gagataagag tagcaagcag tgatggggag aagataatct   28740
agtgtaggaa agatggaaag aatggtgata tttcacaact gctagattga cactttaact   28800
tgagagttat ccctctataa actggatatt tgctgagcaa agtttaaaga aaactccatg   28860
tattcagtaa tgttttccag accccacttc tcttatataa gccagtggct tagagtgctt   28920
gctctaattt ctatattcca ttaaacaagg gtgggatttc ttctcattca aaccatttgt   28980
gactttgccc tttagtgacc tctaccatca ccctatcatt aatgatccaa gtgattagaa   29040
tggatggcta tgtgtttgta ggttgtttgt tgtctttaat gaatagattc attgaatgga   29100
attaactgtg ctcttctaga acattggatc tgtgttctca tttagattgt atttgtaatc   29160
tccccacttc ccaccatcaa cagtggcata atgtgaatta atttatgtgg tatctgtcat   29220
ttaaaaaaca tgagctctct ccttcctttt tttgtcttaa acataggaca tggatttgat   29280
tgacatactt tggaggcaag atatagatct tggagtaagt cgagaagtat ttgacttcag   29340
tcagcgacgg aaagagtatg agctggaaaa acagaaaaaa cttgaaaagg aaagacaaga   29400
acaactccaa aaggagcaag agaaagcctt tttcgctcag ttacaactag atgaagagac   29460
aggtgaattt ctcccaattc agccagccca gcacatccag tcagaaacca gtggatctgc   29520
caactactcc caggtacaga gtactcagtt cttgggaaag ttatggcagg tttaaggaaa   29580
cactgagcaa ggaattaaaa tatctggatt tgagttccag ctttgccttt cttttactta   29640
accttgtcaa atctactttc caacctcagc ctcctgatga gttcagtacc taacctgagt   29700
tcagtaccca acctattgat cttaacagtg ttattgtgag gattgggaag acttaagtta   29760
caccaaagag ttttgtaaag tatagaaaca tcctgtaagg atcaagtagc agcaacagaa   29820
gtagtagcag gagaaccaag tagcagggat tactggcgtt actgtgtgtg gcaagcactg   29880
ttttaagaac atatactgac tgatttaatt aacacaacta tattaattag ttaccattat   29940
ccctgtttta tctacgatga gcaactgaag ctcacaaagg ttaaataatt tgcccagatc   30000
actcagaaaa ttggaggagc taagatctga acccatgtgg tctagttcaa attgtgcatc   30060
aaagtgatct ctgaaataag ataaatattt acttaacttg attataaata ttttatgaac   30120
atcaattatt gaatatttag cttggcaatg gaatatttaa ccattttgt tttcctttgt    30180 gtcattccct tttatcaggt tgcccacatt cccaaatcag atgctttgta ctttgatgac   30240
tgcatgcagc ttttggcgca gacattcccg tttgtagatg acaatgaggt gaggtataaa   30300
ataacctggt taatagaaaa actccatcat aactataaaa taacaatcta ttctatgtaa   30360
gtcccgtcaa tgaatctcca tttaaaagaa taaaaacatt tttaggagga aattttttaa   30420
ccaaggaaat actcttgtca aggaaaacctt agcctataaa taactttaca attaagaaaa   30480 aaaaaaccc ttcacacaat acaaaaccaa aaccattgac tattgcatag ccagaaacat    30540
ggacagcata accatggaaa caaataaccc atttgctgca agtatctaag aggtttggtg   30600
agtaaagagc cagctgggca ataaacgaag acttgttcag ttaacaattt taataaatct   30660
gttttatcta gtaccactgt gctagatatt atataaacta aatcctaaag attgtactta   30720
cgcattttaa agtttacttt caaatgctta agctgaaaca gaccagcaaa ttataaattt   30780
gagtcagtgg ggtaggaaaa aaagattgt tatttacaaa cggggtcatg actggttagt    30840
aagtagagag acacagaact gcagctgatt ccatttttgtt ttgtagtggt gccttagagc   30900
```

| | |
|---|---|
| ttactcatcc cctgttggtg gaagactcat aaatcaatgc cttatcaatt ttaggtttct | 30960 |
| tcggctacgt ttcagtcact tgttcctgat attcccggtc acatcgagag cccagtcttc | 31020 |
| attgctacta atcaggctca gtcacctgaa acttctgttg ctcaggtagc ccctgttgat | 31080 |
| ttagacggta tgcaacagga cattgagcaa gtttgggagg agctattatc cattcctgag | 31140 |
| ttacaggtaa ctaaaataga atgtaatact ggagattttt tttatattca gtgcctttag | 31200 |
| tcattctgat tatttatata ccacctattt ataggaagga ttggagggtg ctattaactt | 31260 |
| a | 31261 |

<210> SEQ ID NO 3
<211> LENGTH: 5808
<212> TYPE: DNA
<213> ORGANISM: Homo sapiens

<400> SEQUENCE: 3

| | |
|---|---|
| aacagactgg cggcgcgcgg aaaacgcgtc acgtgacgac tggccccgcc tcttcctctc | 60 |
| ggtcccatat tgaactcgag ttggaagagg cgagtccggt ctcaaaatgg aggtaaaacc | 120 |
| gccgcccggt cgcccccagc ccgactccgg ccgtcgccgt cgccgccggg gggaggaggg | 180 |
| ccatgatcca aaggaaccag agcagttgag aaaactgttt attggtggtc tgagctttga | 240 |
| aactacagat gatagtttac gagaacattt tgagaaatgg ggcacactca cagattgtgt | 300 |
| ggtaatgaga gaccccccaaa caaaacgttc caggggcttt ggttttgtga cttattcttg | 360 |
| tgttgaagag gtggatgcag caatgtgtgc tcgaccacac aaggttgatg ggcgtgtagt | 420 |
| ggaaccaaag agagctgttt ctagagagga ttctgtaaag cctggtgccc atctaacagt | 480 |
| gaagaaaatt tttgttggtg gtattaaaga agatacagaa gaatataatt tgagagacta | 540 |
| ctttgaaaag tatggcaaga ttgaaaccat agaagttatg gaagacaggc agagtggaaa | 600 |
| aaagagagga tttgcttttg taacttttga tgatcatgat acagttgata aaattgttgt | 660 |
| tcagaaatac cacactatta atgggcataa ttgtgaagtg aaaaaggccc tttctaaaca | 720 |
| agagatgcag tctgctggat cacagagagg tcgtggaggt ggatctggca attttatggg | 780 |
| tcgcggaggg aactttggag gtggtggagg taattttggc cgtggtggaa actttggtgg | 840 |
| aagaggaggc tatggtggtg gaggtggtgg cagcagaggt agttatggag gaggtgatgg | 900 |
| tggatataat ggatttggag gtgatggtgg caactatggc ggtggtcctg gttatagtag | 960 |
| tagagggggc tatggtggtg gtggaccagg atatggaaac caaggtggtg gatatggtgg | 1020 |
| aggtggagga tatgatggtt acaatgaagg aggaaatttt ggcggtggta actatggtgg | 1080 |
| tggtgggaac tataatgatt ttggaaatta gtggacaa cagcaatcaa attatggacc | 1140 |
| catgaaaggg ggcagttttg gtggaagaag ctcgggcagt ccctatggtg gtggttatgg | 1200 |
| atctggtggt ggaagtggtg gatatggtag cagaaggttc taaaaacagc agaaaagggc | 1260 |
| tacagttctt agcaggagag agagcgagga gttgtcagga aagctgcagg ttactttgag | 1320 |
| acagtcgtcc caaatgcatt agaggaactg taaaaatctg ccacagaagg aacgatgatc | 1380 |
| catagtcaga aaagttactg cagcttaaac aggaaaccct tcttgttcag gactgtcata | 1440 |
| gccacagttt gcaaaagtg cagctattga ttaatgcaat gtagtgtcaa ttagatgtac | 1500 |
| attcctgagg tcttttatct gttgtagctt tgtcttttc ttttctttt cattacatca | 1560 |
| ggtatattgc cctgtaaatt gtggtagtgg taccaggaat aaaaaattaa ggaattttta | 1620 |
| acttttcaat atttgtgtag ttcagttttt ctacattta gtacagaaac tttaacaaaa | 1680 |

```
tgcagtttcg aaggtgtttc cttgtgagtt aacaagtaaa gaagatcatt gttaattact   1740
attttgtatg aattttgcta aagttaactg taaagaaaca cctgctgact tgcagtttaa   1800
ggggaatcta ttctccccat ttccaaacca tgatatgaat gggcgctgac atgtggagag   1860
aatagataat ttgtgtgttt gcaatgtgtg ttttagataa ataggattgg gtatttaaat   1920
tagcatttgt gaatttaata gcattaagat taccttcaaa tgaaaaaaaa tctcaaaatt   1980
tctatttggt ttttgtgcat tttcttttaa aatgtaatca tatgatttta gtgtgttaga   2040
cttgctgagt cctagctgtg tttagaacat ctctattcta catttacctt ggtcaaattt   2100
gaactgctgc cataggtttt gggtgtaaag aatgtttact gccctccatt taaattctga   2160
aaagggatgg tggatgtttt ccctctccta cgttagaaac cattcttaaa aacttttgaa   2220
aatatagaac cattaagcct gctatatctg agcaaattag tgggtacctt tttttcttaa   2280
tttaaagcac aagaggccca taaatcttga gttactttaa attcttttttt ttgatacaag   2340 ttttcagagc aagagaataa aaatcatgtg ttattaaacc cctaactggc tggcatgctt   2400
tcctgtttgt attctataca ttttgctgga tgaaaccaag gatagttcag gtataattgt   2460
ccaaaataac ctaactgcag cagaaatgta gcacagttgc ttagtacagg cttctcactt   2520
cctacagacc tgaattcaaa tttggatagt ctgagttctt aaattcccaa agaacacact   2580
gttattcttt gtgtatattt caacataaat catgttgtta ccaatttgtt tggaaggccc   2640
tggttgagaa gagtttagt taataaggtc atatatacat atattaatat aaaccaatgt   2700
ctactgtttt gctccagcta gtgcttacag tttcattcga gccctgagta tgtgccctgc   2760
tgttactctc tttggtagtt gaacgttgaa ttcaagtctt ttgtttttaag aagtactaag   2820 caaacaagca ataaaagggg gaatggggtg tgctagtgtt tgaatatgct ctcttgttgc   2880
tctaattctg tgcctctgtg cattaatatt tggatgcatg caatgccagc atggaaattg   2940
gtcttcacac atactgcagt tttccagaaa cattcacaaa ccaataaatg taacagacat   3000
tccatttgtt aatgggcata tatgtgaaaa gcagtagaga aaataggcta atattagaaa   3060
atggttaagt cctaaataac ttcaagtgtg gttatataat ggacactgtc aatgttcata   3120
acttaaacct gggtacctgg tcaaaataat gcttgggaaa cattaaaatt gagctaaatt   3180
gtctcaagtt cttttattca tataaataaa gtttaaagga atgggggaga ttaacatttc   3240
ctgttttatg tttgtgaaat tgtttgacac aaccttgaca gtatccttta atggcatgag   3300
gttaattgta ctgttaacca actttctatg ttctggaact agtattatag tgaaaacatt   3360
tacagtaagt tgatgtttac aacctataag caggtgaaat ctgtgtatgt gacctgttta   3420
taagttgtat tagcttagct cttgtgaaca gtgtggaaaa gtaagccatg aggagagcga   3480
tttaaccacc tttaaaggac ctaagatgtg ctttttaagc acagtgtgga tcacagaaac   3540
tcactaagac aggacttcag cagccttttg tgtttggaca agtcagcata aataaagaat   3600
gacaaggcag cagcaagagc ttcaactaca gagaagtgaa ggcataagat actatgatga   3660
tagtgagcaa ctttccaaaa gctagttaaa tctgcttatt acaactgaaa tatcgaagaa   3720
agtctagcag gaaggagctc ttcgcctttt ggaacatcaa tgagagatag ttgccacagt   3780
cactaggtct agcatttaga cctgcaagga agggcaataa gcattaggta aggcttgaat   3840
ttgaattttt tcactaatta aagagtaatt ttttgtaaag caaggtaaga gtaatctttt   3900
tgatttgcag gttgaatgag aaccctactt gcctaaatga ggaatgtctt tcctaccatc   3960
taaaatacga aggtttctgg ctgggtaagg tttgtagttg acagtaaaac ctgatgcacc   4020
catttgtttc cctgcaagtc tacattacat atttcacaac tttgtccctc tctagtaggc   4080
```

-continued

```
acattggaaa aattcttcaa ctgaaaacta ccttggtacc atgtcctaca cgttttaaac    4140 cttagttttta aaaattcccc tgcgaaatag ccataagtat tcatatcaag tcagttgtga   4200
ctccttgtgt atacaattca tttttttgtgt cttcagggta aactcaattt ttggtaaagt   4260
ggtttcagct tttgtgaaaa ccgttttggt gtgtaagcat gacacacaac agactcagta   4320
agctgcccat cctcatacta ggaaaacacc ttcaaaggaa cattaaaagt taccagggcc   4380
aggcacagtg gctcacgcct gtaatcccag cactttggga ggctgaggca gatggatccc   4440
aagtccagga atttgagacg agcctgggca acatagtgag agcctgtcaa caaaaaatag   4500
aaaaattagt tgggcttggt gatacacatc tgtagtccca gctatttggg aggctgcctt   4560
gatatcaggc agtcgaggct gcagtgagct gactgcccca ctgtattcca gcctgggtga   4620
ccccatctca aagaagaaaa gttaccagat gtcatgggta aaggttggtc ttcaagtggc   4680
ctcataagtt gtcttgcatt taaattcagg gaattcattg gaccaatagg ttacattttc   4740 gttcctttt tgttttggtt catctgttaa gcagtgggg cctaattact gctcctttgt    4800
aaaaacacat tttcccaaag aacactgaat taccgttcaa actggttgtt gatgggtaat   4860
aagggctgtt tttgctgccc caaaagggct taacaattta gtcggatagt ttacttaaaa   4920
aaaaaaatcc tttggagaca tactgaaaat gcaaactagt ttctaaatta tcaattccct   4980
acatgaagaa gcagtttgcc agagtttagt ctcagaaaat gactggttgg ctctatttaa   5040
atcagaaccc aatttctacg cgtgttgaat aaggtaacag cctttgatga atttccttca   5100
caacatggtt ttagtgaagc aaacattttt tttttaaggg cattgttctt tctagtttat   5160 ttcttttttat gaaataaaat tattttattt aaacagttcc attgtcgttt ctgaaaacta  5220
cagtattctc agaagttgta gcagcagtaa aaaaaaaaaa gttgttatat aagtgattgg   5280
ggcagattta actgattttg ttaaaccaat ttgtaagtta ctgcttctaa tattacactt   5340
ctaaaaagct gaatttatac tcatgtccta aaggagaata tgtggtaata agtatatttt   5400
gttaagtaac taattgaaat aggcttggtt ttaagagttc cagtatataa taatcacaaa   5460
ttgaaacctg acagtatctt gggagttcca gtaatgtcac aaattagtga ataagcatgc   5520
cagtgtgcaa gggtaatgta aggattgtta gcctatctaa atattcaaaa ttactttaaa   5580
acttaagtat gttttctgat ttttaagaat tcagaagtgt tctgtaatgg attcagatgt   5640
ttcatttgta gtataatgaa atgtttacag aaagataact ttttcattaa aatattttta   5700
gaaatgtgtg tgttgttttg tcacttcaca atgttcatgt gacttaaaca ctataggtga   5760
atattttgac ttatttttacc agtaagtaat aaaacaacag gaaacttg               5808
```

<210> SEQ ID NO 4
<211> LENGTH: 34
<212> TYPE: DNA
<213> ORGANISM: Artificial Sequence
<220> FEATURE:
<223> OTHER INFORMATION: Antisense oligonucleotide

<400> SEQUENCE: 4

```
uaggaaagac auuccucauu ccucauuuag gcaa                                34
```

<210> SEQ ID NO 5
<211> LENGTH: 27
<212> TYPE: DNA
<213> ORGANISM: Artificial Sequence
<220> FEATURE:
<223> OTHER INFORMATION: Antisense oligonucleotide

```
<400> SEQUENCE: 5
uucugcuacc auauccacca cuuccac                                              27

<210> SEQ ID NO 6
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 6
taggaaagac attcctcat                                                       19

<210> SEQ ID NO 7
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 4

<400> SEQUENCE: 7
gccuaaauga ggaaugucuu uccta                                                25

<210> SEQ ID NO 8
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 5

<400> SEQUENCE: 8
ggaaguggug gauaugguag cagaa                                                25

<210> SEQ ID NO 9
<211> LENGTH: 412
<212> TYPE: DNA
<213> ORGANISM: Artificial Sequence
<220> FEATURE:
<223> OTHER INFORMATION: Antisense oligonucleotide

<400> SEQUENCE: 9
aaattttggc ggtggtaact atggtggtgg tgggaactat aatgattttg gaaattatag          60
tggacaacag caatcaaatt atggacccat gaaaggggc agttttggtg gaagaagctc          120
gggcagtccc tatggtggtg gttatggatc tggtggtgga agtggtggat atggtagcag         180
aaggttctaa aaacagcaga aaagggttga atgagaaccc tacttgccta aatgaggaat         240
gtctttccta ccatctaaaa tacgaaggtt tctggctgga gattctgtga ggagctggaa         300
ggcaagcttg gttcatgcag acatgaggca ctaatgtttt caactgggtt gctctccact        360
ggatgcctat taaatgctca gcactttgga gtataccaga gaagtaaaga ca                412
```

TREATMENT OF NUCLEAR FACTOR (ERYTHROID-DERIVED 2)-LIKE 2 (NRF2) RELATED DISEASES BY INHIBITION OF NATURAL ANTISENSE TRANSCRIPT TO NRF2

REFERENCE TO PRIOR APPLICATIONS

The present application is a divisional of U.S. Ser. No. 13/256,720 filed on Sep. 15, 2011, which is a National Stage Entry of International Application No. PCT/US2010/027394 filed on Mar. 16, 2010, which claims priority to U.S. Provisional Application No. 61/160,369, entitled "Antisense Compounds for Nuclear Factors," filed Mar. 16, 2009 and U.S. Provisional Application No. 61/181,062, entitled "Nuclear Factor (Erythroid-Derived 2)-Like 2 Antisense Oligonucleotides," filed May 26, 2009, which are all incorporated herein by reference in their entireties.

FIELD OF THE INVENTION

Embodiments of the invention comprise oligonucleotides modulating expression and/or function of NRF2 and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an NRF2 polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 5808 of SEQ ID NO: 3 (FIG. 3) thereby modulating function and/or expression of the NRF2 polynucleotide in patient cells or tissues in vivo or in vitro.

In another preferred embodiment, an oligonucleotide targets a natural antisense sequence of NRF2 polynucleotides, for example, nucleotides set forth in SEQ ID NO: 3, and any variants, alleles, homologs, mutants, derivatives, fragments and complementary sequences thereto. Examples of antisense oligonucleotides are set forth as SEQ ID NOS: 4 to 6 (FIG. 4).

Another embodiment provides a method of modulating function and/or expression of an NRF2 polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the NRF2 polynucleotide; thereby modulating function and/or expression of the NRF2 polynucleotide in patient cells or tissues in vivo or in vitro.

Another embodiment provides a method of modulating function and/or expression of an NRF2 polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an NRF2 antisense polynucleotide; thereby modulating function and/or expression of the NRF2 polynucleotide in patient cells or tissues in vivo or in vitro.

In a preferred embodiment, a composition comprises one or more antisense oligonucleotides which bind to sense and/or antisense NRF2 polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 2 shows
SEQ ID NO: 1: *Homo sapiens* nuclear factor (erythroid-derived 2)-like 2 (NFE2L2), transcript variant 1, mRNA. (NCBI Accession No.: NM_006164)
SEQ ID NO: 2: Genomic sequence of NRF2 (exons are shown in capital letters, introns small).

FIG. 3 shows SEQ ID NO: 3: Natural NRF2 antisense sequence (BU656954.1).

FIG. 4 shows the antisense oligonucleotides, SEQ ID NOs: 4 to 6. * indicates phosphothioate bond.

FIG. 5 shows the sense oligonucleotides, SEQ ID NOs: 7 and 8. The sense oligonucleotides SEQ ID NO: 7 and 8 are the reverse complements of the antisense oligonucleotides SEQ ID NO: 4 and 5 respectively.

DETAILED DESCRIPTION

Figure 1A:
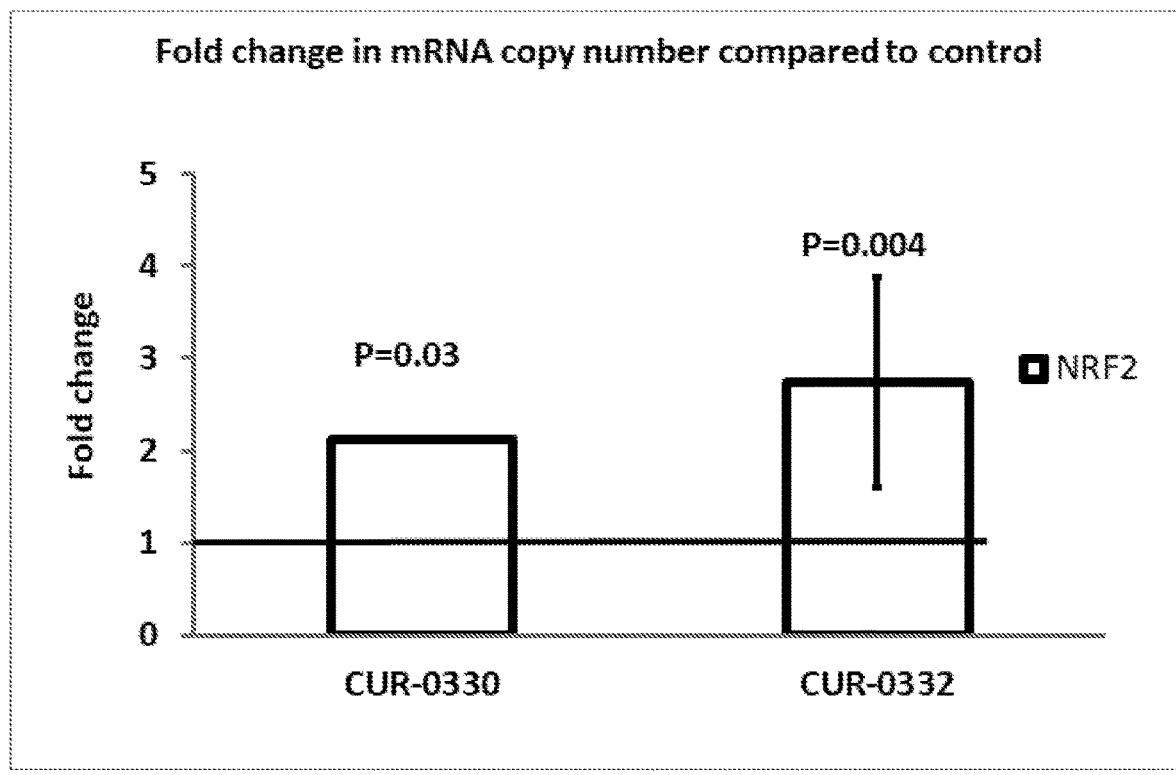
FIG. 1A is a graph of real time PCR results showing the fold change+standard deviation in NRF2 mRNA after treatment of HepG2 cells with phosphorothioate oligonucleotides introduced using Lipofectamine 2000, as compared to control. Real time PCR results show that the levels of NRF2 mRNA in HepG2 cells are significantly increased 48 h after treatment with two of the oligonucleotides designed to NRF2 antisense BU656954.1. Bars denoted as CUR-0330 and CUR-0332 correspond to samples treated with SEQ ID NOS: 4 and 5 respectively.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different order and/or concurrently with other acts or events. Furthermore, not all illustrated acts or events are required to implement a methodology in accordance with the present invention.

Oxygen is essential for humans but reactive oxygen species generated in the body as its by-product is highly toxic. It is known that cellular damages due to oxidative stress caused by reactive oxygen species are deeply involved in onset or progress of various age-related chronic diseases (e.g., arteriosclerosis, hypertension, diabetes, cerebral nerve degenerative disease, skin disease, eye disease, asthma, and cancer). Enhancing the capability in protecting from oxidative stress is useful in preventing these diseases or delaying their progress (*Biomed Pharmacother.* 57, 251-60 (2003)).

A series of proteins called phase II enzymes collaborate in undertaking protection of the body from oxidative stress or detoxification of xenobiotic substances. Examples of known phase II enzymes include glutathione S-transferase (GST), NAD(P)H: quinine oxidoreductase 1 (NQO1), glutanyl-cysteinyl ligase (GCL), heme oxygenase 1 (HO1), and thioredoxin reductase 1 (TXNRD1). A common sequence called antioxidant responsive element (ARE) is present in a promoter of each gene of these phase II enzymes, and its expression is induced by the transcription factor NRF2 (NF-E2 related factor 2) (*Annu Rev Pharmacol Toxicol.* 43:233-60 (2003)). It is generally believed that NRF2 is present in the cytoplasm as a Keap1-NRF2 complex and when an activator acts therein, it moves into the nucleus and forms a heterodimer with a small Maf protein to bind ARE, thereby augmenting the expression of phase II enzymes.

Since the brain has a relatively high metabolic rate and a low cell regenerative capacity, it is an organ vulnerable to damages due to oxidative stress as compared to the other organs. Further, since the amount of reactive oxidative species in the brain increases with age, it is suggested that the capability in protecting the brain with oxidative stress may decrease with age. The increase in oxidative stress is believed to be closely related to the onset of cerebral nerve diseases such as Alzheimer's disease, Parkinson's disease, and amyotrophic lateral sclerosis. For e.g., accumulation of 4-hydroxynonenal or malondialdehyde, which is marker for lipid peroxides, has been observed in the cerebral cortex or hippocampus of Alzheimer's disease patients, the substantia nigra of Parkinson's disease patients, and the spinal fluid of amyotrophic lateral sclerosis patients. Further, in Alzheimer's disease, β-amyloid, which is believed to be a causative substance, increases the amount of intracellular hydrogen peroxide and that in Parkinson's disease, increasing dopamine is known to increase the amount of multiple reactive oxygen species molecular species including hydrogen peroxide. In Parkinson's disease, it has also been reported that the amount of glutathione in the substantia nigra makes a biochemical index for the disease and the amount of glutathione decreases with the aggravation of the disease (*Nat Med.* 10 Suppl. S18-25 (2004)). Accordingly, augmentation of the capability in the protection from reactive oxygen species, for e.g., in preventing cellular lesions due to hydrogen peroxide and in increasing the amount of intracellular glutathione is considered to be effective in preventing or ameliorating these cerebral neurodegenerative diseases. It has also been reported that dimethyl fumarate and tert-butylhydroquinone which induce phase II enzymes suppress cell death due to dopamine and hydrogen peroxide (*J. Biol Chem.* 277, 388-94 (2002); *J Neurochem.* 71, 69-77 (1998); *Neurosci Lett.;* 273, 109-12 (1999)).

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) Ann. Rev. Biochem. 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "NRF2" and "Nuclear factor (erythroid-derived 2)-like 2" are inclusive of all family members, mutants, alleles, fragments, species, coding and noncoding sequences, sense and antisense polynucleotide strands, etc.

As used herein, the words 'Nuclear factor (erythroid-derived 2)-like 2', Nuclear factor erythroid 2-related factor 2, NFE2-related factor 2, NF-E2-related factor 2, HEBP1, NRF2, Nrf2, NFE2L2, are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N. J., et al. (2001) Proc. Natl. Acad. Sci. USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) Nature 409:363-365). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) *Nature* 409:363-366; Boutla, A., et al. (2001) *Curr. Biol.* 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 in, about 15 to about 25 nt or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) *J. American. Med. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al. (1990) *Cell*, 63, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.*, 25(22), 4429-4443, Toulmé, J. J., (2001) *Nature* Biotechnology 19:17-18; Manoharan M., (1999) *Biochemica et Biophysica Acta* 1489: 117-139; Freier S. M., (1997) *Nucleic Acid Research*, 25:4429-4443, Uhlman, E., (2000) *Drug Discovery & Development*, 3: 203-213, Herdewin P., (2000) *Antisense & Nucleic Acid Drug Dev.*, 10:297-310); 2'-O, 3'-C-linked [3.2.0] bicycloarabinonucleosides (see e.g. N. K Christiensen, et al, (1998) *J. Am. Chem. Soc.*, 120: 5458-5463; Prakash T P, Bhat B. (2007) *Curr Top Med Chem.* 7(7):641-9; Cho E J, et al. (2009) *Annual Review of Analytical Chemistry*, 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) *J. Mol. Biol.*, 215, 403-410; Zhang and Madden, (1997) *Genome Res.*, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radio-isotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is readied. Treating also includes the amelioration of a symptom of a disease (e.g., lessen the pain or discomfort), wherein such amelioration may or may not be directly affecting the disease (e.g., cause, transmission, expression, etc.).

As used herein, the term "cancer" refers to any malignant tumor, particularly arising in the lung, kidney, or thyroid. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). A Neurological disease or disorder includes but is not limited to acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; DandyWalker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIV associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease;

infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; mild-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; a neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive mutifocalleukoencephalopathy; progressive sclerosing poliodystrophy; progressive supranuclear palsy; pseudotumor cerebri; Ramsay-Hunt syndrome (types I and 11); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildcat's disease; and Zellweger syndrome.

Polynucleotide and Oligonucleotide Compositions and Molecules

Targets: In one embodiment, the targets comprise nucleic acid sequences of Nuclear factor (erythroid-derived 2)-like 2 (NRF2), including without limitation sense and/or antisense noncoding and/or coding sequences associated with NRF2.

Transcription factor NF-E2-related factor 2 (NRF2) belongs to the basic region-leucine zipper family and is activated in response to electrophiles and reactive oxygen species. NRF2 coordinately regulates the constitutive and inducible transcription of a wide array of genes to involved in drug metabolism, detoxification, and antioxidant defenses. During periods of oxidative stress, NRF2 is released from sequestration in the cytoplasm and translocates to the nucleus. NRF2 binds antioxidant response elements (AREs) in the regulatory regions of the target genes and activates transcription.

Chronic obstructive pulmonary disease (COPD), which comprises emphysema and chronic bronchitis resulting from prolonged exposure to cigarette smoke (CS), is a major public health burden with no effective treatment. Emphysema is also associated with pulmonary hypertension, which can progress to right ventricular failure, an important cause of morbidity and mortality among patients with COPD. Recently, it has been shown that patients with advanced COPD have a decline in expression of the Nrf2 pathway in lungs, indicating that loss of this antioxidative protective response is a key factor in the pathophysiological progression of emphysema. Furthermore, genetic disruption of Nrf2 in mice causes early-onset and severe emphysema.

The liver is frequently exposed to insults, including toxic chemicals and alcohol, viral infection or metabolic overload. Although it can fully regenerate after acute injury, chronic liver damage causes liver fibrosis and cirrhosis, which can result in complete liver failure.

In preferred embodiments, antisense oligonucleotides are used to prevent or treat diseases or disorders associated with abnormal nuclear factor (erythroid-derived 2)-like 2 (NRF2) expression and/or function. This includes all forms of nuclear factor (erythroid-derived 2)-like 2 (NRF2) molecules, including mutants and aberrant expression or function of normal or abnormal nuclear factor (erythroid-derived 2)-like 2 (NRF2) molecules.

In a preferred embodiment, modulation of NF-E2-related factor (Nrf2) transcription factor protects the liver from acute and chronic toxin-mediated damage.

In another preferred embodiment, up-regulation or activation of Nrf2 prevents orameliorate toxin-induced liver injury and fibrosis.

In another preferred embodiment, modulation of NF-E2-related factor 2 (Nrf2) transcription factor prevents or treats gastrointestinal diseases or disorders in patients.

Brain tumors are associated with genetic alterations of oncogenes and tumor suppressor genes. Accumulation of reactive oxygen species (ROS) in cells leads to oxidative stress-induced damage, resulting in tumorigenesis.

Nuclear factor erythroid 2-related factor 2 (Nrf2) is a redox-sensitive transcription factor that up-regulates a battery of antioxidative genes and cytoprotective enzymes that constitute the defense against oxidative stress. Modulation of this polynucleotide is important in treatment of diseases or disorders that are associated with oxidative stress. Exemplary Nuclear factor (erythroid-derived 2)-like 2 (NRF2) mediated diseases and disorders which can be treated with cell/tissues regenerated from stem cells obtained using the antisense compounds comprise: chronic obstructive pulmonary disease (COPD), multiple sclerosis, a hepatic disease or disorder, a gastrointestinal disease or disorder, diabetes, autoimmunity, an immune related disease or disorder, an immunodeficiency (e.g., AIDS), a neurological disease or disorder, a neurodegenerative disease or disorder, a disease or disorder or condition associated with oxidative stress, an eye disease (e.g., age-related macular degeneration, cataracts, light retinopathy, retinopathy of prematurity etc.), a skin disease, asthma, arteriosclerosis, a chronic inflammatory diseases or condition (e.g., vasculitis, pulmonary bronchitis, rheumatoid arthritis, osteoarthritis, hepatitis, pancreatitis, dermatitis, esophagitis, ulcerative colitis, Crohn's disease, conjunctivitis etc.), nerve repair and paralysis, neuroendocrine differentiation, an inflammatory disease, a muscular disease or disorder, diseases or disorders associated with infectious organisms, senile plaques, cerebral amyloid angiopathy, atherosclerosis, glioblastoma, amyloid deposition, neurofibrillary tangles, dementia, choriocarcinoma, astrocytoma, amyloidosis, hyperlipidemia, neoplastic transformation, an atherosclerotic plaque, an atherosclerotic obstruction, metastasis, myocardial infarction, pulmonary fibrosis, necrosis, shock, melanoma, colorectal carcinoma, genetic susceptibility, psoriasis, a disease or disorder associated with abnormal cell proliferation ((e.g., cancer, psoriasis etc.), cancer (e.g., prostate cancer, lung cancer, breast cancer, Non-small cell lung carcinomas (NSCLCs), leukemia etc.), inflammation, glioma, carcinoma, neuropathology, tumors, vascular diseases, cell damage, brain tumors, hypercholesterolemia, liposarcoma, coronary heart disease, coronary artery disease, glomerulonephritis, venous thrombosis and a pathological process.

In another preferred embodiment, the antisense oligonucleotides modulate the expression and/or function of NRF2 in patients suffering from or at risk of developing diseases or disorders associated with NRF2. Examples of such diseases or disorders associated with NRF2 comprise: Alzheimer's disease, multiple sclerosis, senile plaques, cerebral amyloid angiopathy, atherosclerosis, glioblastoma, amyloid deposition, neurodegenerative diseases, neurofibrillary tangles, dementia, choriocarcinoma, astrocytoma, amyloidosis, hyperlipidemia, neurodegeneration, neoplastic transformation, prostate cancer, atherosclerotic plaque, obstruction, AIDS, metastasis, myocardial infarction, pulmonary fibrosis, necrosis, shock, melanoma, colorectal carcinoma, genetic susceptibility, psoriasis, cancer, inflammation, glioma, carcinoma, breast cancer, neuropathology, tumors, prostate carcinoma, vascular diseases, cell damage, brain tumors, Nonsmall cell lung carcinomas (NSCLCs), hypercholesterolemia, liposarcoma, coronary heart disease, immunodeficiency, coronary artery disease, glomeralonephritis, venous thrombosis, pathological processes or leukemia.

In a preferred embodiment, the oligonucleotides are specific for polynucleotides of NRF2, which includes, without limitation noncoding regions. The NRF2 targets comprise variants of NRF2; mutants of NRF2, including SNPs; noncoding sequences of NRF2; alleles, fragments and the like. Preferably the oligonucleotide is an antisense RNA molecule.

In accordance with embodiments of the invention, the target nucleic acid molecule is not limited to NRF2 polynucleotides alone but extends to any of the isoforms, receptors, homologs, non-coding regions and the like of NRF2.

In another preferred embodiment, an oligonucleotide targets a natural antisense sequence (natural antisense to the coding and non-coding regions) of NRF2 targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc. is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of NRF2 including without limitation, antisense sequences which are identified and expanded, using for example, PCR, hybridization etc., one or more of the sequences set forth as SEQ ID NO: 3, and the like, modulate the expression or function of NRF2. In one embodiment, expression or function is up-regulated as compared to a control. In another preferred embodiment, expression or function is down-regulated as compared to a control.

In another preferred embodiment, oligonucleotides comprise nucleic acid sequences set forth as SEQ ID NOS: 4 to 6 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes Nuclear factor (erythroid-derived 2)-like 2 (NRF2).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of Nuclear factor (erythroid-derived 2)-like 2 (NRF2) (SEQ ID NO: 1). Examples of antisense sequences include SEQ ID NOS: 4 to 6.

In another preferred embodiment, the antisense oligonucleotides bind to one or more segments of Nuclear factor (erythroid-derived 2)-like 2 (NRF2) polynucleotides and modulate the expression and/or function of Nuclear factor (erythroid-derived 2)-like 2 (NRF2). The segments comprise at least five consecutive nucleotides of the Nuclear factor (erythroid-derived 2)-like 2 (NRF2) sense or antisense polynucleotides.

In another preferred embodiment, the antisense oligonucleotides are specific for natural antisense sequences of Nuclear factor (erythroid-derived 2)-like 2 (NRF2) wherein binding of the oligonucleotides to the natural antisense sequences of Nuclear factor (erythroid-derived 2)-like 2 (NRF2) modulate expression and/or function of Nuclear factor (erythroid-derived 2)-like 2 (NRF2).

In another preferred embodiment, oligonucleotide compounds comprise sequences set forth as SEQ ID NOS: 4 to 6, antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Nuclear factor (erythroid-derived 2)-like 2 (NRF2), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation colon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., citron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from so-called intergenic regions (Cheng, J. et al. (2005) *Science* 308 (5725), 1149-1154; Kapranov, P. et al. (2005), *Genome Res* 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping pans of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally, U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Nuclear factor (erythroid-derived 2)-like 2 (NRF2) polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Nuclear factor (erythroid-derived 2)-like 2 (NRF2) polynucleotides. "Modulators" are those compounds that decrease or increase the expression of a nucleic acid molecule encoding Nuclear factor (erythroid-derived 2)-like 2 (NRF2) and which comprise at least a 5-nucleotide portion that is complementary to a preferred target segment. The screening method comprises the steps of contacting a preferred target segment of a nucleic acid molecule encoding sense or natural antisense polynucleotides of Nuclear factor (erythroid-derived 2)-like 2 (NRF2) with one or more candidate modulators, and selecting for one or more candidate modulators which decrease or increase the expression of a nucleic acid molecule encoding Nuclear factor (erythroid-derived 2)-like 2 (NRF2) polynucleotides, e.g. SEQ ID NOS: 4 to 6. Once it is shown that the candidate modulator or modulators are capable of modulating (e.g. either decreasing or increasing) the expression of a nucleic acid molecule encoding Nuclear factor (erythroid-derived 2)-like 2 (NRF2) polynucleotides, the modulator may then be employed in further investigative studies of the function of Nuclear factor (erythroid-derived 2)-like 2 (NRF2) polynucleotides, or for use as a research, diagnostic, or therapeutic agent in accordance with the present invention.

Targeting the natural antisense sequence preferably modulates the function of the target gene. For example, the NRF2 gene (e.g. accession number NM_06164, FIG. 2). In a preferred embodiment, the target is an antisense polynucleotide of the NRF2 gene. In a preferred embodiment, an antisense oligonucleotide targets sense and/or natural antisense sequences of Nuclear factor (erythroid-derived 2)-like 2 (NRF2) polynucleotides (e.g. accession number NM_006164, FIG. 2), variants, alleles, isoforms, homologs, mutants, derivatives, fragments and complementary sequences thereto. Preferably the oligonucleotide is an antisense molecule and die targets include coding and noncoding regions of antisense and/or sense NRF2 polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., (1998) Nature, 391, 806-811; Timmons and Fire, (1998) Nature, 395, 854; Timmons et al., (2001) Gene, 263, 103-112; Tabara et al., (1998) Science, 282, 430-431; Montgomery et al., (1998) Proc. Natl. Acad. Sci. USA, 95, 15502-15507, Tuschl et al., (1999) Genes Dev., 13, 3191-3197; Elbashir et al., (2001) Nature, 411, 494-498; Elbashir et al., (2001) Genes Dev. 15, 188-200). For example, such double-stranded moieties have been shown to inhibit the target by the classical hybridization of antisense strand of the duplex to the target, thereby triggering enzymatic degradation of the target (Tijsterman et al., (2002) Science, 295, 694-697).

In a preferred embodiment, an antisense oligonucleotide targets Nuclear factor (erythroid-derived 2)-like 2 (NRF2) polynucleotides (e.g. accession number NM_006164), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Nuclear factor (erythroid-derived 2)-like 2 (NRF2) alone but extends to any of the isoforms, receptors, homologs and the like of Nuclear factor (erythroid-derived 2)-like 2 (NRF2) molecules.

In another preferred embodiment, an oligonucleotide targets a natural antisense sequence of NRF2 polynucleotides, for example, polynucleotides set forth as SEQ ID NO: 3, and any variants, alleles, homologs, mutants, derivatives, fragments and complementary sequences thereto. Examples of antisense oligonucleotides are set forth as SEQ ID NOS: 4 to 6.

In one embodiment, the oligonucleotides are complementary to or bind to nucleic acid sequences of Nuclear factor (erythroid-derived 2)-like 2 (NRF2) antisense, including without limitation noncoding sense and/or antisense sequences associated with Nuclear factor (erythroid-derived 2)-like 2 (NRF2) polynucleotides and modulate expression and/or function of Nuclear factor (erythroid-derived 2)-like 2 (NRF2) molecules.

In another preferred embodiment, the oligonucleotides are complementary to or bind to nucleic acid sequences of NRF2 natural antisense, set forth as SEQ ID NO: 3 and modulate expression and/or function of NRF2 molecules.

In a preferred embodiment, oligonucleotides comprise sequences of at least 5 consecutive nucleotides of SEQ ID NOS: 4 to 6 and modulate expression and/or function of Nuclear factor (erythroid-derived 2)-like 2 (NRF2) molecules.

The polynucleotide targets comprise NRF2, including family members thereof, variants of NRF2; mutants of NRF2, including SNPs; noncoding sequences of NRF2; alleles of NRF2; species variants, fragments and the like. Preferably the oligonucleotide is an antisense molecule.

In another preferred embodiment, the oligonucleotide targeting Nuclear factor (erythroid-derived 2)-like 2 (NRF2) polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of Nuclear factor (erythroid-derived 2)-like 2 (NRF2) polynucleotides, e.g. SEQ ID NO: 3, modulates the expression or function of these targets. In one embodiment, expression or function is up-regulated as compared to a control. In another preferred embodiment, expression or function is down-regulated as compared to a control.

In another preferred embodiment, antisense compounds comprise sequences set forth as SEQ ID NOS: 4 to 6. These oligonucleotides can comprise one or more modified nucleotides, shorter or longer fragments, modified bonds and the like.

In another preferred embodiment, SEQ ID NOS: 4 to 6 comprise one or more LNA nucleotides.

Table I shows exemplary antisense oligonucleotides useful in the methods of the invention.

| Sequence ID | Oligo Name | Sequence |
| --- | --- | --- |
| SEQ ID NO: 4 | CUR-0030 | UAGGAAAGACAUUCCUCAUU CCAUCAUUUAGGCAA |
| SEQ ID NO: 5 | CUR-0032 | UUCUGCUACCAUAUCCACCA CUUCCAC |
| SEQ ID NO: 6 | CUR-0509 | T*A*G*G*A*A*A*G*A*C* A*T*T*C*C*T*C*A*T |

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, Nature 429 1986; Cech, 260 JAMA 3030, 1988; and Jefferies et al., 17 Nucleic Acids Research 1371, 1989).

Because of their sequence-specificity, trans-cleaving enzymatic nucleic acid molecules show promise as therapeutic agents for human disease (Usman & McSwiggen, (1995) Ann. Rep. Med. Chem. 30, 285-294; Christoffersen and Marr, (1995) J. Med. Chem. 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) Proc. R. Soc. London, B 205, 435) have been used to evolve new nucleic acid catalysts capable of catalyzing a variety of reactions, such as cleavage and ligation of phosphodiester linkages and amide linkages, (Joyce, (1989) Gene, 82, 83-87; Beaudry et al., (1992) Science 257, 635-641; Joyce, (1992) Scientific American 267, 90-97; Breaker et al., (1994) TIBTECH 12, 268; Bartel et al., (1993) Science 261:1411-1418; Szostak, (1993) TIBS 17, 89-93; Kumar et al., (1995) FASEB J. 9, 1183; Breaker, (1996) Curr. Op. Biotech., 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987 (Uhlenbeck, O. C. (1987) Nature, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) Nature, 334, 585; Walbot and Bruening, (1988) Nature, 334, 196; Uhlenbeck, O. C. (1987) Nature, 328: 596-600; Koizumi, M., et al. (1988) FEBS Lett., 228: 228-230). This has allowed use of the catalytic RNA to cleave specific target sequences and indicates that catalytic RNAs designed according to the "hammerhead" model may possibly cleave specific substrate RNAs in vivo. (see Haseloff and Gerlach, (1988) Nature, 334, 585; Walbot and Bruening, (1988) Nature, 334, 196; Uhlenbeck, O. C. (1987) Nature, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) *Nat. Rev. Genet.*, 2, 110-119; Matzke et al., (2001) *Curr. Opin. Genet Dev.*, 11, 221-227; Sharp, (2001) *Genes Dev.*, 15, 485-490). When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another preferred embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another preferred embodiment, the antisense oligonucleotides, such as for example, nucleic acid molecules set forth in SEQ ID NOS: 3 to 6 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with NRF2 and the sequences set forth as SEQ ID NOS: 1, 3. The oligonucleotides are also targeted to overlapping regions of SEQ ID NOS: 1, 3.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target. The preferred target is a natural antisense polynucleotide having SEQ ID NO: 9 (BU656954.1).

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) *Acc. Chem. Res.*, 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [known as a methylene (methylimino) or MMI backbone], CH2-O—N (CH3)-CH2, CH2-N (CH3)-N (CH3)-CH2 and O—N (CH3)-(CH2CH2 backbones, wherein the native phosphodiester backbone is represented as O—P—O—CH,). The amide backbones disclosed by De Mesmaeker et al. (1995) *Acc. Chem. Res.* 28:366-374 are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone (Nielsen et al. (1991) *Science* 254, 1497). Oligonucleotides may also comprise one or more substituted sugar moieties. Preferred oligonucleotides comprise one of the following at the 2' position: OH, SH, SCH3, F, OCN, OCH3 OCH3, OCH3 O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2 CH2 OCH3, also known as 2'-O-(2-methoxyethyl)] (Martin et al., (1995) *Helv. Chim. Acta,* 78, 486). Other preferred modifications include 2'-methoxy (2'-OCH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp 75-77; Gebeyehu, G., (1987) et al. *Nucl. Acids Res.* 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., (1989) *Proc. Natl. Acad. Sci. USA* 86, 6553), cholic acid (Manoharan et al. (1994) *Bioorg. Med. Chem. Let.* 4, 1053), a thioether, hexyl-S-tritylthiol (Manoharan et al. (1992) *Ann. N.Y. Acad. Sci.* 660, 306; Manoharan et al. (1993) *Bioorg. Med. Chem. Let.* 3, 2765), a thiocholesterol (Oberhauser et al., (1992) *Nucl. Acids Res.* 20, 533), an aliphatic chain, e.g., dodecandiol or undecyl residues (Saison-Behmoaras et al. EMBO J. 1991, 10, 111; Kabanov et al. (1990) *FEBS Lett.* 259, 327; Svinarchuk et al. (1993) *Biochimie* 75, 49), a phospholipid, e.g., di-hexadecyl-rac-glycerol or triethylammonium 1,2-di-O-hexadecyl-rac-glycero-3-H-phosphonate (Manoharan et al. (1995) *Tetrahedron Lett.* 36, 3651; Shea et al. (1990) *Nucl. Acids Res.* 18, 3777), a polyamine or a polyethylene glycol chain (Manoharan et al. (1995) *Nucleosides & Nucleotides,* 14, 969), or adamantane acetic acid (Manoharan et al. (1995) *Tetrahedron Lett.* 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) *Current Opinions in Drug Discovery & Development* Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat Nos. 5,539,082; 5,714,331; and 5,719,262, each of which is herein incorporated by reference. Further teaching of PNA compounds can be found in Nielsen, et al. (1991) *Science* 254, 1497-1500.

In another preferred embodiment of the invention the oligonucleotides with phosphorothioate backbones and oligonucleosides with heteroatom backbones, and in particular —CH2-NH—O—CH2-, —CH2-N (CH3)-O—CH2- known as a methylene (methylimino) or MMI backbone, —CH2-O—N (CH3)-CH2, —CH2N(CH3)-N(CH3) (CH2- and —O—N(CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to C0 alkyl or C2 to C0 alkenyl and alkynyl. Particularly preferred are O (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other preferred oligonucleotides comprise one of the following at the 2' position: C to C0, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—CH2CH2OCH3, also known as 2'-O-(2-methoxyethyl) or 2'-MOE) (Martin et al., (1995) *Helv. Chim. Acta,* 78, 486-504) i.e., an alkoxyalkoxy group. A further preferred modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N (CH2)2.

Other preferred modifications comprise 2'-methoxy (2'-O CH3), 2'-aminopropoxy (2'-O CH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) Proc. Natl. Acad. Sci. USA, 86, 6553-6556), cholic acid (Manoharan et al., (1994) Bioorg. Med. Chem. Let., 4, 1053-1060), a thioether, e.g., hexyl-S-tritylthiol (Manoharan et al., (1992) Ann. N. Y. Acad. Sci., 660, 306-309; Manoharan et al., (1993) Bioorg. Med. Chem. Let., 3, 2765-2770), a thiocholesterol (Oberhauser et al., (1992) Nucl. Acids Res., 20, 533-538), an aliphatic chain, e.g., dodecandiol or undecyl residues (Kabanov et al., (1990) FEBS Lett., 259, 327-330; Svinarchuk et al., (1993) Biochimie 75, 49-54), a phospholipid, e.g. di-hexadecyl-rac-glycerol or triethylammonium 1,2-di-O-hexadecyl-rac-glycero-3-H-phosphonate (Manoharan et al., (1995) Tetrahedron Lett., 36, 3651-3654; Shea et al., (1990) Nucl. Acids Res., 18, 3777-3783), a polyamine or a polyethylene glycol chain (Manoharan et al., (1995) Nucleosides & Nucleotides, 14, 969-973), or adamantane acetic acid (Manoharan et al., (1995) Tetrahedron Lett., 36, 3651-3654), a palmityl moiety (Mishra et al., (1995) Biochim. Biophys. Acta, 1264, 229-237), or an octadecylamine or hexylamino-carbonyl-t oxycholesterol moiety (Crooke et al., (1996) J. Pharmacol. Exp. Ther., 277, 923-937).

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and preferred target segments identified herein in drug discovery efforts to elucidate relationships that exist between Nuclear factor (erythroid-derived 2)-like 2 (NRF2) polynucleotides and a disease state, phenotype, or condition. These methods include detecting or modulating Nuclear factor (erythroid-derived 2)-like 2 (NRF2) polynucleotides comprising contacting a sample, tissue, cell, or organism with the compounds of the present invention, measuring the nucleic acid or protein level of Nuclear factor (erythroid-derived 2)-like 2 (NRF2) polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNA target in the non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

NRF2 protein and mRNA expression can be assayed using methods known to those of skill in the art and described elsewhere herein. For example, immunoassays such as the ELISA can be used to measure protein levels. NRF2 antibodies for ELISAs are available commercially, e.g., from R&D Systems (Minneapolis, Minn.), Abcam, Cambridge, Mass.

In embodiments, NRF2 expression (e.g., mRNA or protein) in a sample (e.g., cells or tissues in vivo or in vitro) treated using an antisense oligonucleotide of the invention is evaluated by comparison with NRF2 expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the NRF2 protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of NRF2 mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of NRF2 mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Nuclear factor (erythroid-derived 2)-like 2 (NRF2) genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.,* 480, 17-24; Celis, et al., (2000) *FEBS Lett.,* 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) *Methods Enzymol.,* 303, 258-72), TOGA (total gene expression analysis) (Sutcliffe, et al., (2000) *Proc. Natl. Acad. Sci. U.S.A.,* 97, 1976-81), protein arrays and proteomics (Celis, et al., (2000) *FEBS Lett.,* 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol. 2000, 80, 143-57), subtractive RNA fingerprinting (SuRF) (Fuchs, et al., (2000) Anal. Biochem. 286, 91-98; Larson, et al., (2000) *Cytometry* 41, 203-208), subtractive cloning, differential display (DD) (Jurecic and Belmont, (2000) *Curr. Opin. Microbiol.* 3, 316-21), comparative genomic hybridization (Carulli, et al., (1998) *J. Cell Biochem. Suppl.,* 31, 286-96), FISH (fluorescent in situ hybridization) techniques (Going and Gusterson, (1999) *Eur. J. Cancer,* 35, 1895-904) and mass spectrometry methods (To, Comb. (2000) *Chem. High Throughput Screen,* 3, 235-41).

The compounds of the invention are useful for research and diagnostics, because these compounds hybridize to nucleic acids encoding Nuclear factor (erythroid-derived 2)-like 2 (NRF2). For example, oligonucleotides that hybridize with such efficiency and under such conditions as disclosed herein as to be effective Nuclear factor (erythroid-derived 2)-like 2 (NRF2) modulators are effective primers or probes under conditions favoring gene amplification or detection, respectively. These primers and probes are useful in methods requiring the specific detection of nucleic acid molecules encoding Nuclear factor (erythroid-derived 2)-like 2 (NRF2) and in the amplification of said nucleic acid molecules for detection or for use in further studies of Nuclear factor (erythroid-derived 2)-like 2 (NRF2). Hybridization of the antisense oligonucleotides, particularly the primers and probes, of the invention with a nucleic acid encoding Nuclear factor (erythroid-derived 2)-like 2 (NRF2) can be detected by means known in the art. Such means may include conjugation of an enzyme to the oligonucleotide, radiolabeling of the oligonucleotide, or any other suitable detection means. Kits using such detection means for detecting the level of Nuclear factor (erythroid-derived 2)-like 2 (NRF2) in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Nuclear factor (erythroid-derived 2)-like 2 (NRF2) polynucleotides is treated by administering antisense compounds in accordance with this invention. For example, in one non-limiting embodiment, the methods comprise the step of administering to the animal in need of treatment, a therapeutically effective amount of Nuclear factor (erythroid-derived 2)-like 2 (NRF2) modulator. The Nuclear factor erythroid-derived 2)-like 2 (NRF2) modulators of the present invention effectively modulate the activity of the Nuclear factor (erythroid-derived 2)-like 2 (NRF2) or modulate the expression of the Nuclear factor (erythroid-derived 2)-like 2 (NRF2) protein. In one embodiment, the activity or expression of Nuclear factor (erythroid-derived 2)-like 2 (NRF2) in an animal is inhibited by about 10% as compared to a control. Preferably, the activity or expression of Nuclear factor (erythroid-derived 2)-like 2 (NRF2) in an animal is inhibited by about 30%. More preferably, the activity or expression of Nuclear factor (erythroid-derived 2)-like 2 (NRF2) in an animal is inhibited by 50% or more. Thus, the oligomeric compounds modulate expression of Nuclear factor (erythroid-derived 2)-like 2 (NRF2) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Nuclear factor (erythroid-derived 2)-like 2 (NRF2) and/or in an animal is increased by about 10% as compared to a control. Preferably, the activity or expression of Nuclear factor (erythroid-derived 2)-like 2 (NRF2) in an animal is increased by about 30%. More preferably, the activity or expression of Nuclear factor (erythroid-derived 2)-like 2 (NRF2) in an animal is increased by 50% or more. Thus, the oligomeric compounds modulate expression of Nuclear factor (erythroid-derived 2)-like 2 (NRF2) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Nuclear factor (erythroid-derived 2)-like 2 (NRF2) may be measured in serum, blood, adipose tissue, liver or any other body fluid, tissue or organ of the animal. Preferably, the cells contained within said fluids, tissues or organs being analyzed contain a nucleic acid molecule encoding Nuclear factor (erythroid-derived 2)-like 2 (NRF2) peptides and/or the Nuclear factor (erythroid-derived 2)-like 2 (NRF2) protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, antiraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 4 to 6) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., (1995) *J. Neurochem,* 64: 487; Lim, F., et al., in DNA Cloning: Mammalian Systems, D. Glover, Ed. (Oxford Univ. Press, Oxford England) (1995); Geller, A. I. et al., (1993) *Proc Natl Acad. Sci.: U.S.A.:*90 7603; Geller, A. I., et al., (1990) *Proc Natl. Acad. Sci USA:* 87:1149], Adenovirus Vectors (LeGal LaSalle et al., Science, 259:988 (1993); Davidson, et al., (1993) *Nat. Genet.* 3: 219; Yang, et al., (1995) *J. Virol.* 69: 2004) and Adeno-associated Virus Vectors (Kaplitt, M. G., et al., (1994) *Nat. Genet.* 8:148).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936, 589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposome slacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohex-ylnitrosurea, nitrogen mustards, melphalan, cyclophosph-amide, 6-mercaptopurine, 6-thioguanine, cytarabine, 5-aza-cytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemo-therapeutic agents may be used individually (e.g., 5-FU and oligonucleotide), sequentially (e.g., 5-FU and oligonucle-otide for a period of time followed by MTX and oligonucle-otide), or in combination with one or more other such chemotherapeutic agents (e.g., 5-FU, MTX and oligonucle-otide, or 5-FU, radiotherapy and oligonucleotide). Anti-inflammatory drugs, including but not limited to nonsteroi-dal anti-inflammatory drugs and corticosteroids, and antiviral drugs, including but not limited to ribivirin, vid-arabine, acyclovir and ganciclovir, may also be combined in compositions of the invention. Combinations of antisense compounds and other non-antisense drugs are also within the scope of this invention. Two or more combined com-pounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Nuclear factor (erythroid-derived 2)-like 2 (NRF2), and the second target may be a region from another nucleotide sequence. Alter-natively, compositions of the invention may contain two or more antisense compounds targeted to different regions of the same Nuclear factor (erythroid-derived 2)-like 2 (NRF2) nucleic acid target. Numerous examples of antisense com-pounds are illustrated herein and others may be selected from among suitable compounds known in the art. Two or more combined compounds may be used together or sequen-tially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucle-otides are described, e.g., in U.S. Pat. No. 7,563,884, "Anti-sense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all pur-poses to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreci-ated that variations in proportions and alternatives in ele-ments of the components shown will be apparent to those skilled in the art and are within the scope of embodiments of the present invention.

Example 1: Design of Antisense Oligonucleotides Specific for a Nucleic Acid Molecule Antisense to a Nuclear Factor (Erythroid-Derived 2)-Like 2 (NRF2) and/or a Sense Strand of Nuclear Factor (Erythroid-Derived 2)-Like 2 (NRF2) Polynucle-otide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appro-priate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or Light-Typer instrument, Roche Diagnostics, Lewes, UK).

Melting peaks are constructed by plotting the negative derivative of fluorescence with respect to temperature (−d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2: Modulation of NRF2 Polynucleotides

Treatment of HepG2 Cells with Antisense Oligonucleotides

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of 1.5× $10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with HepG2 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00232352_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Results:

Real time PCR results show that the levels of NRF2 mRNA in HepG2 cells are significantly increased 48 h after treatment with two of the oligos designed to NRF2 antisense BU656954.1 (FIG. 1A).

Treatment of CHP212 Cells with Antisense Oligonucleotides

CHP212 cells from ATCC (cat #CRL-2273) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of 1.5× $10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with CHP212 cells. A Similar mixture including 2 µl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00232352_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 1B:
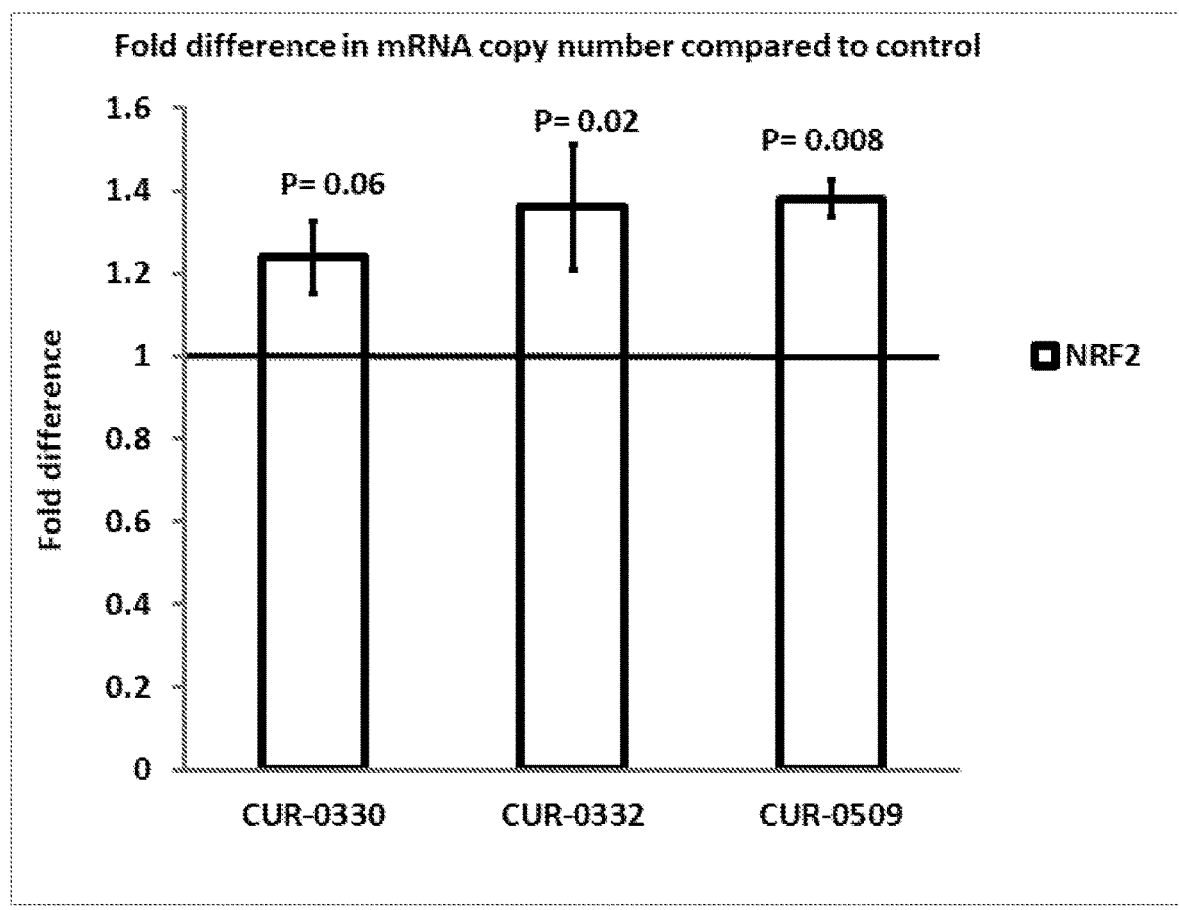
FIG. 1B is a graph of real time PCR results showing the fold change+standard deviation in NRF2 mRNA after treatment of CHP212 cells with phosphorothioate oligonucleotides introduced using Lipofectamine 2000, as compared to control. Real time PCR results show that the levels of NRF2 mRNA in CHP212 cells are significantly increased 48 h after treatment with two of the oligonucleotides designed to NRF2 antisense BU656954.1. Bars denoted as CUR-0330, CUR-0332 and CUR-0509 correspond to samples treated with SEQ ID NOS: 4, 5 and 6 respectively.

Results:

Real time PCR results show that the levels of NRF2 mRNA in CHP212 cells are significantly increased 48 h after treatment with two of the oligos designed to NRF2 antisense BU656954.1 (FIG. 1B).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A pharmaceutical composition comprising a synthetic, modified single-stranded oligonucleotide of 16 to 34 nucleotides in length comprising at least one modification wherein the at least one modification is selected from: at least one modified sugar moiety; at least one modified internucleotide linkage; at least one modified nucleotide, and combinations thereof; wherein said oligonucleotide is an antisense compound which is 100% complementary to and specifically hybridizes to a complementary target region of a natural antisense polynucleotide having SEQ ID NO: 3 of the NRF2 gene and wherein said target region is selected from nucleotides 1054-1259 and 3910-3984 of said SEQ ID NO: 3 and upregulates the function and/or expression of a Nuclear factor (erythroid-derived 2)-like 2 (NRF2) gene in vivo or in vitro as compared to a normal control and a pharmaceutically acceptable excipient.

2. The composition of claim 1, wherein the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

3. The composition of claim 1, wherein said oligonucleotide comprises at least one phosphorothioate internucleotide linkage.

4. The composition of claim 1, wherein said oligonucleotide comprises a backbone of phosphorothioate internucleotide linkages.

5. The composition of claim 1, wherein the oligonucleotide comprises at least one modified nucleotide, said modified nucleotide selected from: a peptide nucleic acid, a locked nucleic acid (LNA), analogue, derivative, and a combination thereof.

6. The composition of claim 1, wherein the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

7. The composition of claim 1, wherein the oligonucleotide comprises a plurality of modifications, wherein said modifications comprise modified nucleotides selected from: peptide nucleic acids, locked nucleic acids (LNA), analogues, derivatives, and a combination thereof.

8. The composition of claim 1, wherein the oligonucleotide comprises at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and a combination thereof.

9. The composition of claim 1, wherein the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

10. The composition of claim 1, wherein the oligonucleotide comprises the sequence set forth as SEQ ID NO: 6.

\* \* \* \* \*